United States Patent
Cullen et al.

(10) Patent No.: US 9,346,796 B2
(45) Date of Patent: May 24, 2016

(54) METHODS AND INTERMEDIATES FOR PREPARING PHARMACEUTICAL AGENTS

(71) Applicant: Gilead Sciences, Inc., Foster City, CA (US)

(72) Inventors: Aaron J. Cullen, Dublin, CA (US); Richard Hung Chiu Yu, San Francisco, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 14/372,995

(22) PCT Filed: Feb. 1, 2013

(86) PCT No.: PCT/US2013/024431
§ 371 (c)(1),
(2) Date: Jul. 17, 2014

(87) PCT Pub. No.: WO2013/116715
PCT Pub. Date: Aug. 8, 2013

(65) Prior Publication Data
US 2014/0364602 A1    Dec. 11, 2014

Related U.S. Application Data

(60) Provisional application No. 61/594,686, filed on Feb. 3, 2012.

(51) Int. Cl.
| | |
|---|---|
| C07D 417/12 | (2006.01) |
| C07C 271/12 | (2006.01) |
| C07C 271/16 | (2006.01) |
| C07C 271/20 | (2006.01) |
| C07D 233/60 | (2006.01) |
| C07C 309/73 | (2006.01) |
| C07C 329/16 | (2006.01) |
| C07D 203/20 | (2006.01) |
| C07D 277/24 | (2006.01) |
| C07D 277/28 | (2006.01) |

(52) U.S. Cl.
CPC ............ *C07D 417/12* (2013.01); *C07C 271/12* (2013.01); *C07C 271/16* (2013.01); *C07C 271/20* (2013.01); *C07C 309/73* (2013.01); *C07C 329/16* (2013.01); *C07D 203/20* (2013.01); *C07D 233/60* (2013.01); *C07D 277/24* (2013.01); *C07D 277/28* (2013.01)

(58) Field of Classification Search
None
See application file for complete search history.

(56) References Cited

U.S. PATENT DOCUMENTS

| | | | | |
|---|---|---|---|---|
| 5,763,464 | A * | 6/1998 | Randad | C07C 235/50 514/357 |
| 7,939,553 | B2 | 5/2011 | Desai et al. | |
| 8,148,374 | B2 | 4/2012 | Desai et al. | |
| 8,497,396 | B2 | 7/2013 | Polniaszek et al. | |
| 8,853,210 | B2 | 10/2014 | Polniaszek et al. | |
| 2003/0153771 | A1 | 8/2003 | Kolb et al. | |
| 2013/0280212 | A1 * | 10/2013 | Desai | A61K 31/426 424/85.4 |

FOREIGN PATENT DOCUMENTS

| | | |
|---|---|---|
| CN | 101967130 A | 2/2011 |
| EP | 402646 A1 | 12/1990 |
| IN | 02473MU2012 A | 11/2012 |
| WO | WO-94/14436 A1 | 7/1994 |
| WO | WO-97/19061 A1 | 5/1997 |
| WO | WO-03/106445 A1 | 12/2003 |
| WO | WO-2008/010921 A2 | 1/2008 |
| WO | WO-2008/027932 A2 * | 3/2008 |
| WO | WO-2008/103949 A1 | 8/2008 |
| WO | WO-2010/115000 A2 | 10/2010 |
| WO | WO-2010/115000 A3 | 9/2011 |
| WO | WO-2012/088153 A1 | 6/2012 |

OTHER PUBLICATIONS

Kempf et al., Bioorganic & Medicinal Chemistry Letters, 1995, 5(22), pp. 2725-2728.*

Duggan, M.E. et al. (1983). "Preparation of Optically Active 2-Aminoalkylphosphinic and Phosphonic Acids," Tetrahedron Letters 24(29):2935-2938.

Ghosh, A.K. et al. (1993) "Potent HIV-1 Protease Inhibitors: Stereoselective Synthesis of a Dipeptide Mimic" *Journal of Organic Chemistry* 58(5):1025-1029.

Gurjar, M.K. et al. (1997). "Synthesis of Novel C.sub.2-Symmetric and Pseudo C2-Symmetric Based Diols, Epoxides and Dideoxy Derivatives of HIV Protease Inhibitors," Tetrahedron 53(13):4769-4778.

Hannam, J. et al. (2006). "Rapid and Selective Synthesis of Substituted 1,2,5-Thiadiazolidine 1,1-Dioxides," Synlett. 6:833-836.

Hiebl, J. et al. (1999). "Large-Scale Synthesis of Hematoregulatory Nonapeptide SK&F 107647 by Fragment Coupling," J. Pept. Res. 54(1):54-65.

Hodgson, D.M. et al. (2006). "Dimerization of Lithiated Terminal Aziridines," Angew. Chem. Int. Ed. 45(6):935-938.

Hodgson, D.M. et al. (Nov. 2007). "Dimerization and Isomerization Reactions of .alpha.-Lithiated Terminal Aziridines," J. Org. Chem. 72(26):10009-10021.

(Continued)

*Primary Examiner* — Laura L. Stockton
(74) *Attorney, Agent, or Firm* — Joel B. Silver; Florence Jovic

(57) ABSTRACT

Methods and intermediates useful for preparing a compound of formula I:

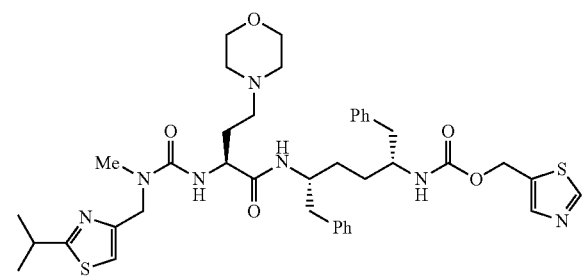

and salts thereof.

2 Claims, No Drawings

(56) References Cited

OTHER PUBLICATIONS

International Search Report and Written Opinion for PCT/US/2013/024431 mailed Jul. 3, 2013.

Mukai, T. et al. (Mar. 2008). "Synthesis of .beta.-Tetrapeptide Analog as a Mother Compound for the Development of Matrix Metalloproteinase-2-Imaging Agents," Chem. & Pharmaceutical Bulletin 56(3):260-265.

Natelson, S. et al. (1989). "Preparation of D-, DL-, and L-Homoserine Lactone from Methionine," Microchemical Journal 40(2):226-232.

Noe, M. et al. (2005). "Asymmetric Dihydroxylation of Alkenes" *Organic Reactions* 66(2):109-625.

Olah, G.A. et al. (1982). "Iodotrimethylsilane—A Versatile Synthetic Reagent," Tetrahedron 38(15):2225-2277.

Preliminary Amendment for U.S. Appl. No. 14/268,891, filed May 2, 2014.

Ramu, E. et al. (2009) "A Short approach to the synthesis of the ritonavir and lopinavir core and its C-3 epimer via cross metathesis" *Tetrahedron Asymetry* 20(19):2201-2204.

Rao, A.V. et al. (1995). "Synthesis of a Novel C2-Symmetrical (2S,5S)-2,5-Bis-[(1,1-dimethyl-ethoxy)carbonylamino]-1,6-diphenylhex-3-ene: Applications in the Synthesis of Potential HIV Protease Inhibitors" *Tetrahedron Letters* 36(14):2505-2508.

Spaltenstein, A. et al. (1987). "New Approaches to the Synthesis of tran-Alkene Isosteres of Dipeptides," J. Org. Chem. 52(17):3759-3766.

U.S. Appl. No. 14/268,891, filed May 2, 2014.

Wuts, P.G.M. et al. ( Dec. 2006) Greene's Protective Groups in Organic Synthesis, 4 sup. th Edition, John Wiley & Sons, Inc. pp. 851-852.

Wuts, P.G.M. et al. (Dec. 2006) Greene's Protective Groups in Organic Synthesis, 4.sup.th Edition, John Wiley & Sons, Inc., pp. 872-873.

Xu, L. et al. (Feb. 4, 2009). "A Novel and Efficient Synthesis of Chiral C.sub.2-Symmetric 1,4-Diamines," Tetrahedron Letters 50(5):552-554.

First Office Action Dated Jul. 16, 2015 for China Patent Application No. 201380007712X.

Ghosh, A. et al. (1999) "Asymmetric dihydroxylation route to a dipeptide isostere of a protease inhibitor: enantioselective synthesis of the core unit of ritonavir" *Chem. Commun.* 1025-1026.

Search Report and Written Opinion dated Apr. 14, 2015 for Singapore Patent Application No. 11201404527Q.

\* cited by examiner

METHODS AND INTERMEDIATES FOR PREPARING PHARMACEUTICAL AGENTS

CROSS-REFERENCE TO RELATED APPLICATIONS

This application claims the benefit of priority from U.S. Provisional Patent Application No. 61/594,686 filed Feb. 3, 2012, the content of which is hereby incorporated by reference herein in its entirety.

BACKGROUND

International Patent Application Publication Number WO 2008/010921 and International Patent Application Publication Number WO 2008/103949 disclose certain compounds that are reported to be useful to modify the pharmacokinetics of a co-administered drug, e.g. by inhibiting cytochrome P450 monooxygenase. One specific compound identified therein is a compound of formula I.

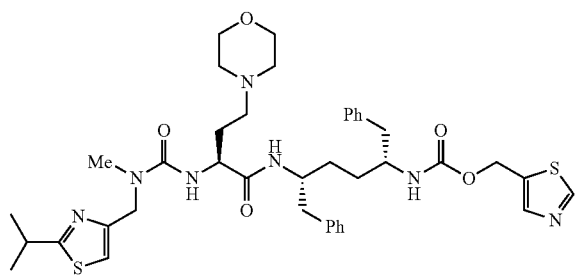

I

International Patent Application Publication Number WO 2010/115000 discloses methods for preparing the compound of formula I and salts thereof. Two intermediates discussed in these applications include the compound of formula II and the compound of formula III and salts thereof.

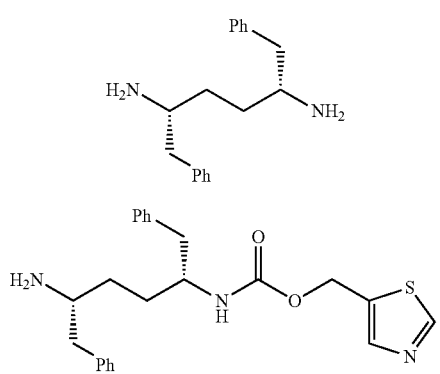

II

III

European Patent Application EP 486948 discloses a compound of formula IV' and International Patent Application Publication Number WO 1994/14436 discloses a compound of formula V'.

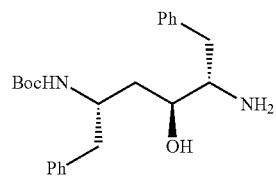

IV'

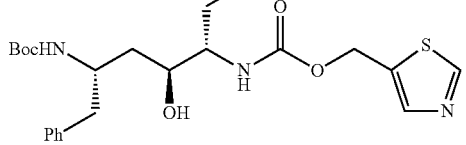

V'

There is currently a need for improved synthetic methods and intermediates that can be used to prepare the compound of formula I and salts thereof. There is also a need for improved methods and intermediates that can be used to prepare the compound of formula II and the compound of formula III which are useful for preparing the compound of formula I. The improved methods and intermediates may reduce the cost, time and/or the amount of waste or provide an increased yield associated with the existing methods for preparing the compounds of formula I or formula II or formula III or salts or protected derivatives thereof.

SUMMARY

A new synthetic processes and intermediates would be useful for preparing the compound of formula I. In particular, the new synthetic processes and intermediates are useful for preparing intermediates (e.g. the compounds of formula II and III) used to prepare the compound of formula I. Accordingly, in one embodiment a compound is selected from:

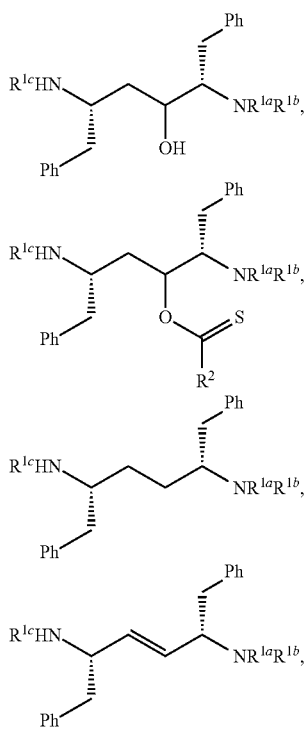

-continued

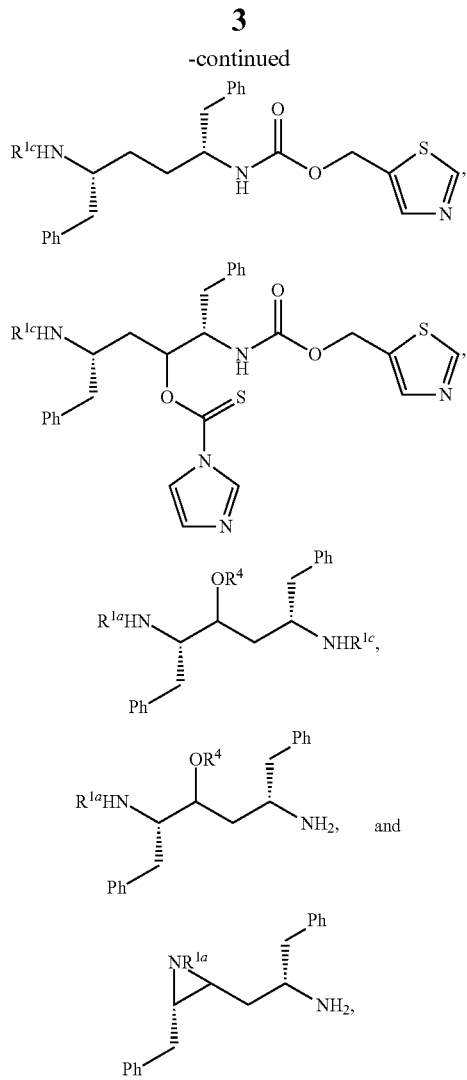

wherein:

$R^{1a}$ and $R^{1b}$ are each independently an amine protecting group; or $R^{1a}$ is an amine protecting group and $R^{1b}$ is H;

$R^{1c}$ is —C(O)O(C$_1$-C$_6$)alkyl wherein —C(O)O(C$_1$-C$_6$)alkyl is optionally substituted with one or more (e.g. 1, 2, 3, 4 or 5) halogen or (C$_1$-C$_6$)alkoxy;

$R^2$ is —SMe or imidazol-1-yl; and $R^4$ is —SO$_2$(C$_1$-C$_6$)alkyl or —SO$_2$aryl, wherein —SO$_2$(C$_1$-C$_6$)alkyl is optionally substituted with one or more (e.g. 1, 2, 3, 4 or 5) halogen, and wherein —SO$_2$aryl is optionally substituted with one or more (e.g. 1, 2, 3, 4 or 5) halogen, (C$_1$-C$_6$)alkyl or NO$_2$;

and salts thereof;

provided the compound is not:

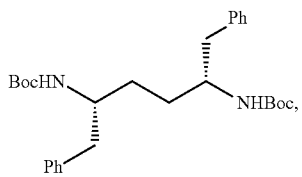

-continued

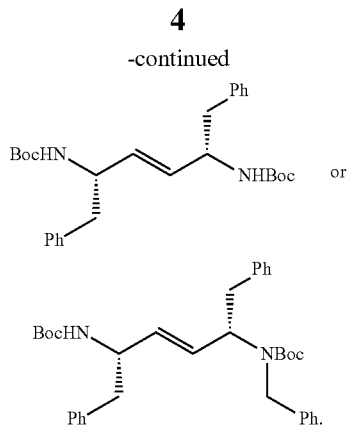

In another embodiment there is a method for preparing a compound of formula 1a or a salt thereof, comprising protecting a compound of formula IVa:

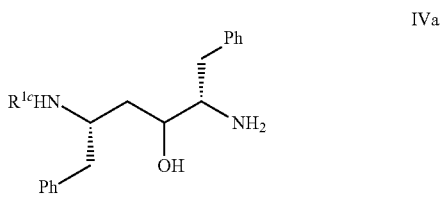

IVa or a salt thereof to provide the corresponding compound of formula 1a:

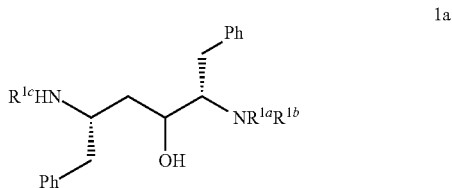

1a or the salt thereof, wherein $R^{1a}$ and $R^{1b}$ are each independently an amine protecting group; or $R^{1a}$ is an amine protecting group and $R^{1b}$ is H; and $R^{1c}$ is —C(O)O(C$_1$-C$_6$)alkyl wherein —C(O)O(C$_1$-C$_6$)alkyl is optionally substituted with one or more halogen or (C$_1$-C$_6$)alkoxy.

In another embodiment there is a method for preparing a compound of formula 2a or a salt thereof, comprising activating a compound of formula 1a:

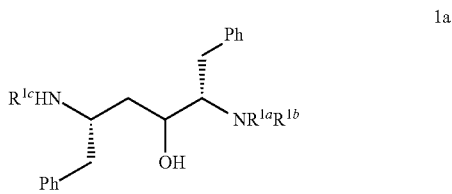

1a or a salt thereof, to provide the corresponding compound of formula 2a:

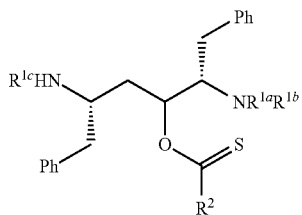

2a or the salt thereof, wherein $R^{1a}$ and $R^{1b}$ are each independently an amine protecting group; or $R^{1a}$ is an amine protecting group and $R^{1b}$ is H; $R^{1c}$ is —C(O)O($C_1$-$C_6$)alkyl wherein —C(O)O($C_1$-$C_6$)alkyl is optionally substituted with one or more halogen or ($C_1$-$C_6$)alkoxy and $R^2$ is SMe.

In another embodiment there is a method for preparing a compound of formula 4 or a salt thereof, comprising deoxygenating a compound of formula 2a:

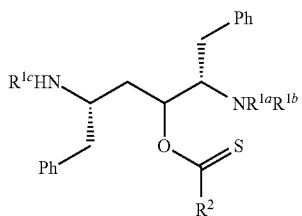

2a or a salt thereof, to provide the corresponding compound of formula 4:

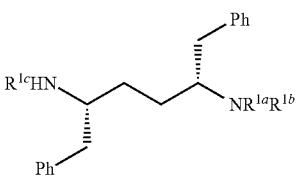

4 or the salt thereof wherein $R^{1a}$ and $R^{1b}$ are each independently an amine protecting group; or $R^{1a}$ is an amine protecting group and $R^{1b}$ is H, $R^{1c}$ is —C(O)O($C_1$-$C_6$)alkyl wherein —C(O)O($C_1$-$C_6$)alkyl is optionally substituted with one or more halogen or ($C_1$-$C_6$)alkoxy and $R^2$ is SMe.

In another embodiment there is a method for preparing a compound of formula 3a or a salt thereof comprising activating a compound of formula 1a:

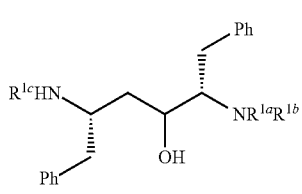

1a or a salt thereof, to provide the corresponding compound of formula 3a:

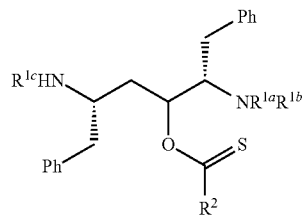

3a or the salt thereof wherein $R^{1a}$ and $R^{1b}$ are each independently an amine protecting group; or $R^{1a}$ is a protecting group and $R^{1b}$ is H; $R^{1c}$ is —C(O)O($C_1$-$C_6$)alkyl wherein —C(O)O($C_1$-$C_6$)alkyl is optionally substituted with one or more halogen or ($C_1$-$C_6$)alkoxy; and $R^2$ is imidazol-1-yl.

In another embodiment there is a method for preparing a compound of formula 4 or a salt thereof, comprising deoxygenating a compound of formula 3a:

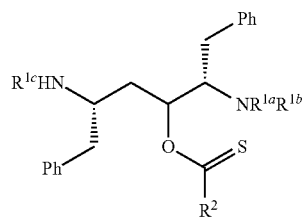

3a or a salt thereof, to provide the corresponding compound of formula 4:

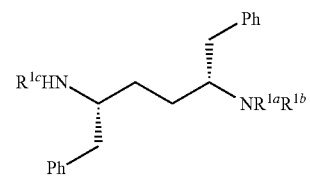

4 or the salt thereof, wherein $R^{1a}$ and $R^{1b}$ are each independently an amine protecting group; or $R^{1a}$ is an amine protecting group and $R^{1b}$ is H; $R^{1c}$ is —C(O)O($C_1$-$C_6$)alkyl wherein —C(O)O($C_1$-$C_6$)alkyl is optionally substituted with one or more halogen or ($C_1$-$C_6$)alkoxy; and $R^2$ is imidazol-1-yl.

In another embodiment there is a method for preparing a compound of formula 2a' or a salt thereof, comprising activating a compound of formula 1a:

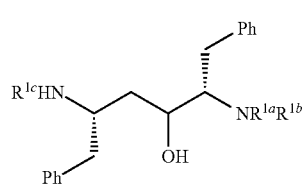

1a or a salt thereof, to provide the corresponding compound of formula 2a:

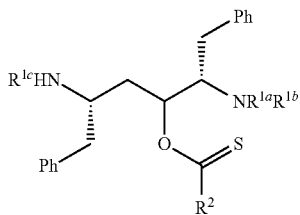

2a' or the salt thereof wherein $R^{1a}$ and $R^{1b}$ are each independently an amine protecting group; or $R^{1a}$ is an amine protecting group and $R^{1b}$ is H; $R^{1c}$ is —C(O)O(C$_1$-C$_6$)alkyl wherein —C(O)O(C$_1$-C$_6$)alkyl is optionally substituted with one or more halogen or (C$_1$-C$_6$)alkoxy and $R^2$ is SMe or imidazol-1-yl.

In another embodiment there is a method for preparing a compound of formula 4 or a salt thereof, comprising deoxygenating a compound of formula 2a':

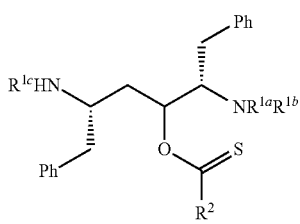

2a' or a salt thereof, to provide the corresponding compound of formula 4:

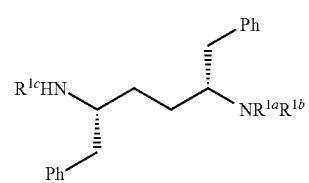

4 or the salt thereof, wherein $R^{1a}$ and $R^{1b}$ are each independently an amine protecting group; or $R^{1a}$ is an amine protecting group and $R^{1b}$ is H; $R^{1c}$ is —C(O)O(C$_1$-C$_6$)alkyl wherein —C(O)O(C$_1$-C$_6$)alkyl is optionally substituted with one or more halogen or (C$_1$-C$_6$)alkoxy; and $R^2$ is SMe or imidazol-1-yl.

In another embodiment there is a method for preparing a compound of formula II or a salt thereof; comprising deprotecting a compound of formula 4:

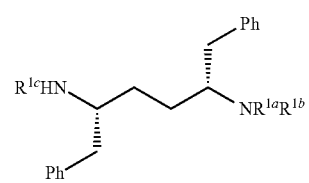

4 or a salt thereof; to provide the compound of formula II:

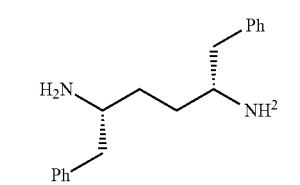

II or the salt thereof, wherein $R^{1a}$ and $R^{1b}$ are each independently an amine protecting group; or $R^{1a}$ is an amine protecting group and $R^{1b}$ is H; and $R^{1c}$ is —C(O)O(C$_1$-C$_6$)alkyl wherein —C(O)O(C$_1$-C$_6$)alkyl is optionally substituted with one or more halogen or (C$_1$-C$_6$)alkoxy; provided that $R^{1a}$ is not —C(=O)O(CH$_3$)$_3$ when $R^{1c}$ is —C(=O)O(CH$_3$)$_3$ and $R^{1b}$ is H.

In another embodiment there is a method for preparing a compound of formula 5 or a salt thereof, comprising deprotecting a compound of formula 4:

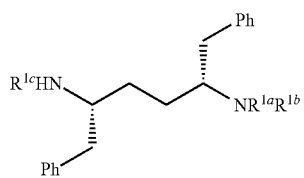

4

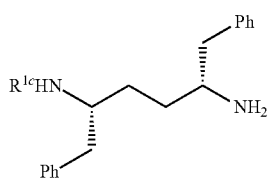

5 or a salt thereof to provide the corresponding compound of formula 5 or the salt thereof, wherein $R^{1a}$ and $R^{1b}$ are each independently an amine protecting group, or $R^{1a}$ is an amine protecting group and $R^{1b}$ is H; and $R^{1c}$ is —C(O)O(C$_1$-C$_6$)alkyl wherein —C(O)O(C$_1$-C$_6$)alkyl is optionally substituted with one or more halogen or (C$_1$-C$_6$)alkoxy.

In another embodiment there is a method for preparing a compound of formula II or a salt thereof, comprising deprotecting a compound of formula 5:

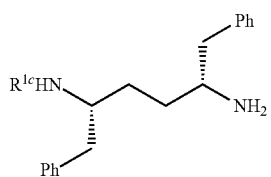

5 or a salt thereof, to provide the compound of formula II:

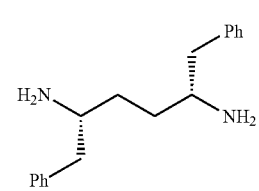

II or the salt thereof; wherein $R^{1c}$ is —C(O)O(C$_1$-C$_6$)alkyl wherein —C(O)O(C$_1$-C$_6$)alkyl is optionally substituted with one or more halogen or (C$_1$-C$_6$)alkoxy.

In another embodiment there is a method for preparing a compound of formula 6 or a salt thereof comprising acylating a compound of formula 5:

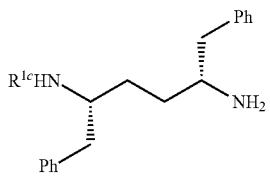

5 or a salt thereof, to provide the corresponding compound of formula 6

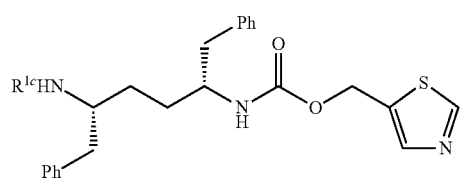

6 or the salt thereof, wherein $R^{1c}$ is —C(O)O($C_1$-$C_6$)alkyl wherein —C(O)O($C_1$-$C_6$)alkyl is optionally substituted with one or more halogen or ($C_1$-$C_6$)alkoxy.

In another embodiment there is a method for preparing a compound of formula 7a or a salt thereof, comprising activating a compound of formula Va:

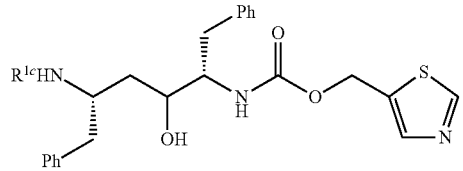

Va or a salt thereof, to provide the corresponding compound of formula 7a:

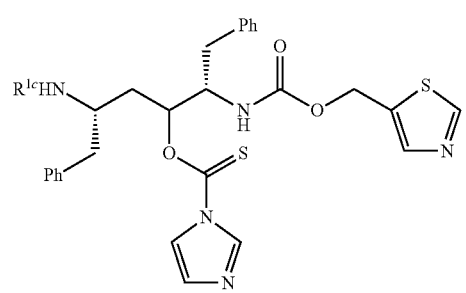

7a or the salt thereof wherein $R^{1c}$ is —C(O)O($C_1$-$C_6$)alkyl wherein —C(O)O($C_1$-$C_6$)alkyl is optionally substituted with one or more halogen or ($C_1$-$C_6$)alkoxy.

In another embodiment there is a method for preparing a compound of formula 6 or a salt thereof, comprising deoxygenating a compound of formula 7a:

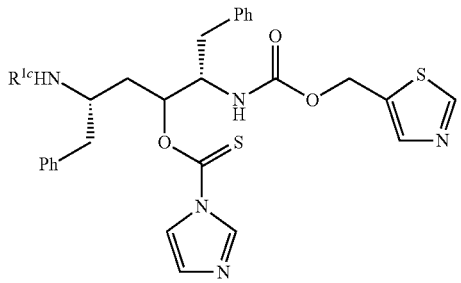

7a or a salt thereof, to provide the corresponding compound of formula 6:

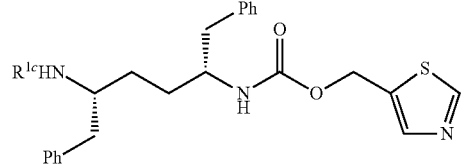

6 or the salt thereof, wherein $R^{1c}$ is —C(O)O($C_1$-$C_6$)alkyl wherein —C(O)O($C_1$-$C_6$)alkyl is optionally substituted with one or more halogen or ($C_1$-$C_6$)alkoxy.

In another embodiment there is a method for preparing a compound of formula III or a salt thereof, comprising deprotecting a compound of formula 6:

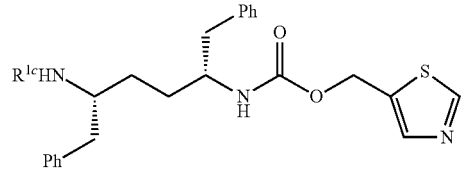

6 or a salt thereof, to provide the compound of formula III:

III or the salt thereof, wherein $R^{1c}$ is —C(O)O($C_1$-$C_6$)alkyl wherein —C(O)O($C_1$-$C_6$)alkyl is optionally substituted with one or more halogen or ($C_1$-$C_6$)alkoxy.

In another embodiment there is a method for preparing a compound of formula 9a, comprising activating a compound of formula 8a:

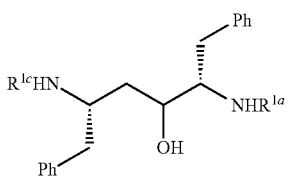

8a or a salt thereof, to provide the corresponding compound of formula 9a:

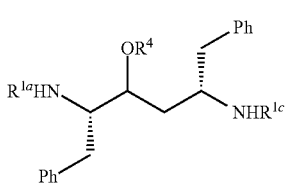

9a wherein $R^{1a}$ is —C(O)OCH$_2$Ph, wherein —C(O)OCH$_2$Ph is optionally substituted with one or more (C$_1$-C$_6$)alkyl or (C$_1$-C$_6$)alkoxy; $R^{1c}$ is —C(O)O(C$_1$-C$_6$)alkyl wherein —C(O)O(C$_1$-C$_6$)alkyl is optionally substituted with one or more halogen or (C$_1$-C$_6$)alkoxy; and $R^4$ is —SO$_2$(C$_1$-C$_6$)alkyl or —SO$_2$aryl, wherein —SO$_2$(C$_1$-C$_6$)alkyl is optionally substituted with one or more halogen, and wherein —SO$_2$aryl is optionally substituted with one or more halogen, (C$_1$-C$_6$) alkyl or NO$_2$.

In another embodiment there is a method for preparing a compound of formula 10a or a salt thereof, comprising deprotecting a compound of formula 9a:

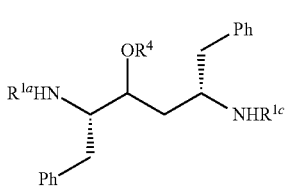

9a to provide the corresponding compound of formula 10a:

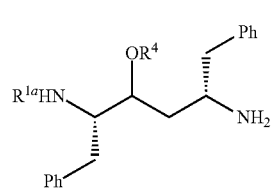

10a or the salt thereof, wherein $R^{1a}$ is —C(O)OCH$_2$Ph, wherein —C(O)OCH$_2$Ph is optionally substituted with one or more (C$_1$-C$_6$)alkyl or (C$_1$-C$_6$)alkoxy; $R^{1c}$ is —C(O)O(C$_1$-C$_6$)alkyl wherein —C(O)O(C$_1$-C$_6$)alkyl is optionally substituted with one or more halogen or (C$_1$-C$_6$)alkoxy; and $R^4$ is —SO$_2$(C$_1$-C$_6$)alkyl or —SO$_2$aryl, wherein —SO$_2$(C$_1$-C$_6$)alkyl is optionally substituted with one or more halogen, and wherein —SO$_2$aryl is optionally substituted with one or more halogen, (C$_1$-C$_6$)alkyl or NO$_2$.

In another embodiment there is a method for preparing a compound of formula 11a or a salt thereof, comprising cyclizing a compound of formula 10a:

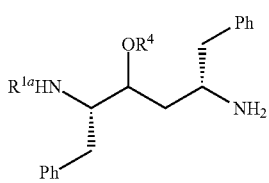

10a or a salt thereof to provide the corresponding compound of formula 11a:

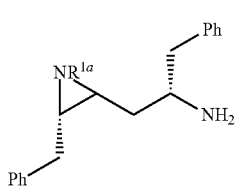

11a or the salt thereof, wherein $R^{1a}$ is —C(O)OCH$_2$Ph, wherein —C(O)OCH$_2$Ph is optionally substituted with one or more (C$_1$-C$_6$)alkyl or (C$_1$-C$_6$)alkoxy; and $R^4$ is —SO$_2$(C$_1$-C$_6$)alkyl or —SO$_2$aryl, wherein —SO$_2$(C$_1$-C$_6$)alkyl is optionally substituted with one or more halogen, and wherein —SO$_2$aryl is optionally substituted with one or more halogen, (C$_1$-C$_6$) alkyl or NO$_2$.

In another embodiment there is a method for preparing a compound of formula II or a salt thereof, comprising ring-opening a compound of formula 11a:

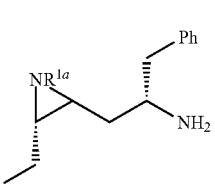

11a or a salt thereof, to a provide the compound of formula II:

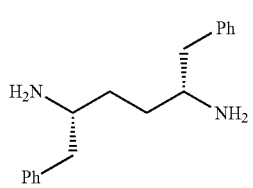

II or the salt thereof, wherein $R^{1a}$ is —C(O)OCH$_2$Ph, wherein —C(O)OCH$_2$Ph is optionally substituted with one or more (C$_1$-C$_6$)alkyl or (C$_1$-C$_6$)alkoxy.

In another embodiment there is a method for preparing a compound of formula I:

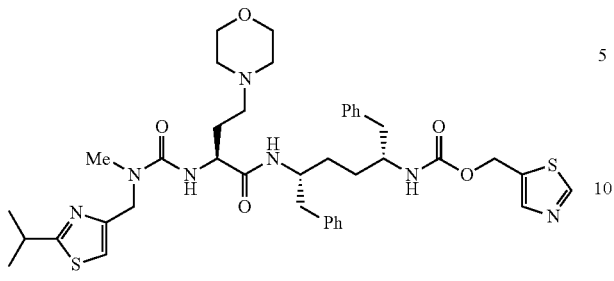

or a salt thereof, comprising converting a compound of formula IVa:

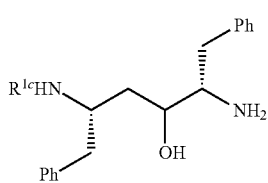

or a salt thereof; into the compound of formula I or the salt thereof, wherein $R^{1c}$ is —C(O)O($C_1$-$C_6$)alkyl wherein —C(O)O($C_1$-$C_6$)alkyl is optionally substituted with one or more halogen or ($C_1$-$C_6$)alkoxy, In another embodiment there is a method for preparing a compound of formula I:

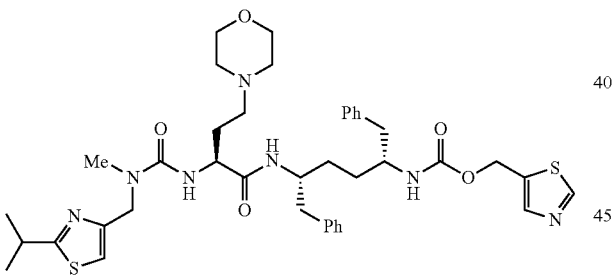

or a salt thereof, comprising converting a compound of formula 1a:

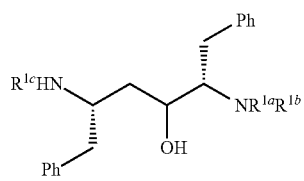

or a salt thereof, into the compound of formula I or the salt thereof, wherein $R^{1a}$ and $R^{1b}$ are each independently an amine protecting group, or $R^{1a}$ is an amine protecting group and $R^{1b}$ is H; and $R^{1c}$ is —C(O)O($C_1$-$C_6$)alkyl wherein —C(O)O($C_1$-$C_6$)alkyl is optionally substituted with one or more halogen or ($C_1$-$C_6$)alkoxy.

In another embodiment there is a method for preparing a compound of formula 1:

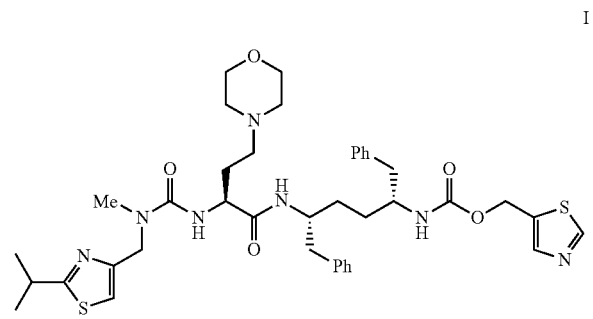 [SMILES: CC(C)c1nc(CN(C)C(=O)N[C@@H](CCN2CCOCC2)C(=O)N[C@H](CC[C@H](Cc2ccccc2)NC(=O)OCc2cncs2)Cc2ccccc2)cs1]

or a salt thereof, comprising converting a compound of formula 2a:

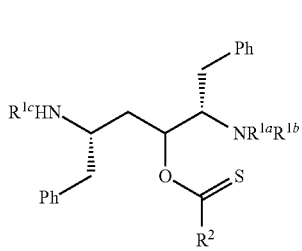

or a salt thereof, into the compound of formula I or the salt thereof, wherein $R^{1a}$ and $R^{1b}$ are each independently an amine protecting group, or $R^{1a}$ is an amine protecting group and $R^{1b}$ is H; $R^{1c}$ is —C(O)O($C_1$-$C_6$)alkyl wherein —C(O)O($C_1$-$C_6$)alkyl is optionally substituted with one or more halogen or ($C_1$-$C_6$)alkoxy; and $R^2$ is —SMe.

In another embodiment there is a method for preparing a compound of formula I:

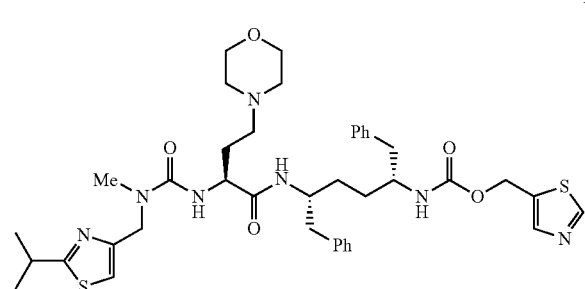

or a salt thereof, comprising converting a compound of formula 3a:

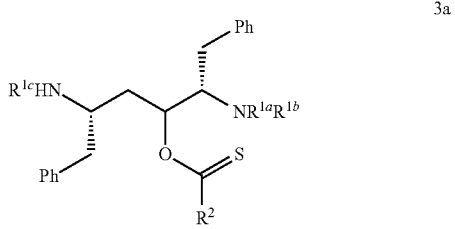

or a salt thereof, into the compound of formula I or the salt thereof, wherein $R^{1a}$ and $R^{1b}$ are each independently an amine protecting group, or $R^{1a}$ is an amine protecting group and $R^{1b}$ is H; $R^{1c}$ is —C(O)O($C_1$-$C_6$)alkyl wherein —C(O)O($C_1$-$C_6$)alkyl is optionally substituted with one or more halogen or ($C_1$-$C_6$)alkoxy; and $R^2$ is imidazol-1-yl.

In another embodiment there is a method for preparing a compound of formula I:

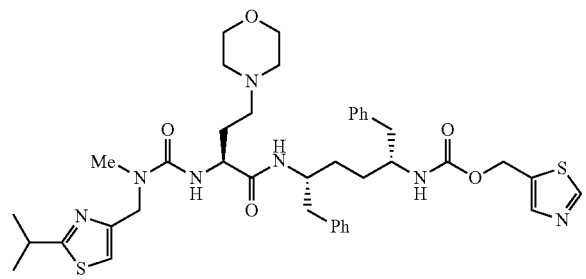

I or a salt thereof, comprising converting a compound of formula 4:

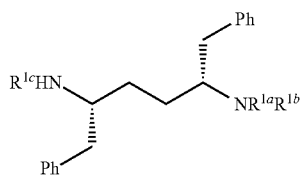

4 or a salt thereof into the compound of formula I or the salt thereof, wherein $R^{1a}$ and $R^{1b}$ are each independently an amine protecting group, or $R^{1a}$ is an amine protecting group and $R^{1b}$ is H; and $R^{1c}$ is —C(O)O($C_1$-$C_6$)alkyl wherein —C(O)O($C_1$-$C_6$)alkyl is optionally substituted with one or more halogen or ($C_1$-$C_6$)alkoxy; provided that $R^{1a}$ is not —C(=O)O($CH_3$)$_3$ when $R^{1c}$ is —C(=O)O($CH_3$)$_3$ and $R^{1b}$ is H.

In another embodiment there is a method for preparing a compound of formula I:

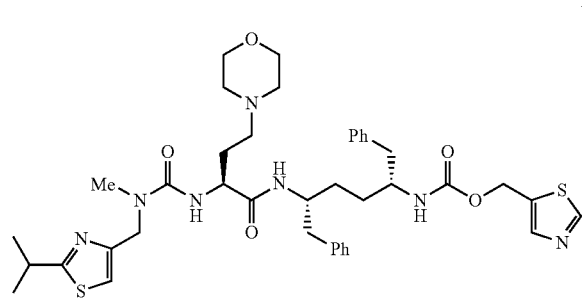

I or a salt thereof, comprising converting a compound of formula 5:

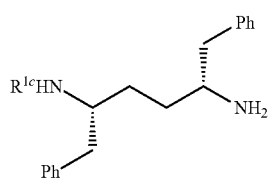

5 or a salt thereof into the compound of formula I or the salt thereof, wherein $R^{1c}$ is —C(O)O($C_1$-$C_6$)alkyl wherein —C(O)O($C_1$-$C_6$)alkyl is optionally substituted with one or more halogen or ($C_1$-$C_6$)alkoxy.

In another embodiment there is a method for preparing a compound of formula I:

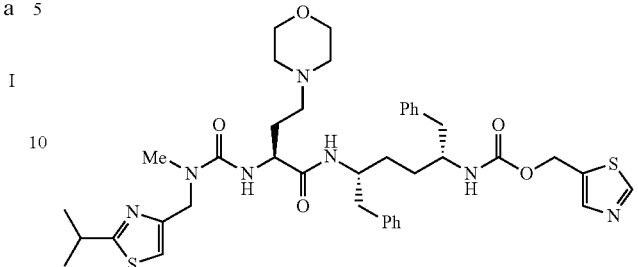

I or a salt thereof, comprising converting a compound of formula 6:

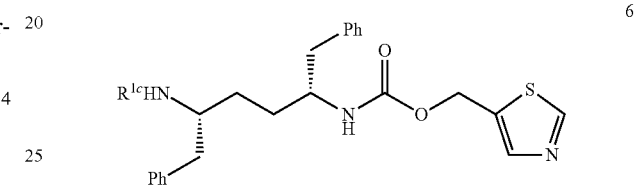

6 or a salt thereof, into the compound of formula I or the salt thereof, wherein $R^{1c}$ is —C(O)O($C_1$-$C_6$)alkyl wherein —C(O)O($C_1$-$C_6$)alkyl is optionally substituted with one or more halogen or ($C_1$-$C_6$)alkoxy.

In another embodiment there is a method for preparing a compound of formula I:

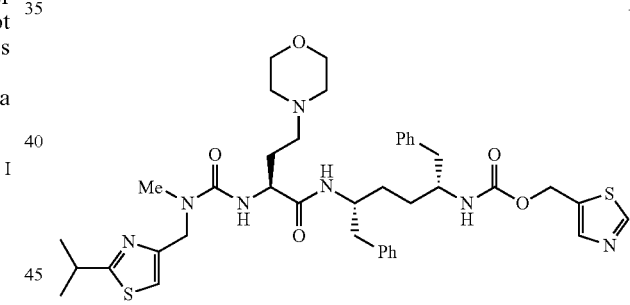

I or a salt thereof comprising converting a compound of formula 7a:

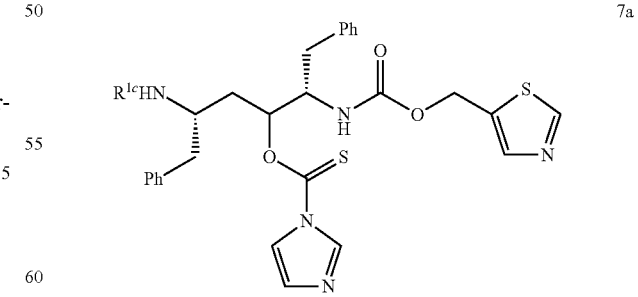

7a or a salt thereof into the compound of formula I or the salt thereof, wherein $R^{1c}$ is —C(O)O($C_1$-$C_6$)alkyl wherein —C(O)O($C_1$-$C_6$)alkyl is optionally substituted with one or more halogen or ($C_1$-$C_6$)alkoxy.

In another embodiment there is a method for preparing a compound of formula I:

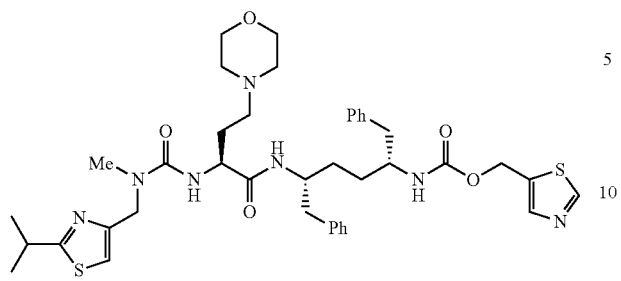

or a salt thereof, comprising converting a compound of formula 9a:

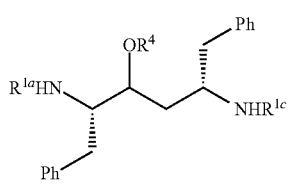

or a salt thereof, into the compound of formula I or the salt thereof, wherein $R^{1a}$ is —C(O)OCH$_2$Ph, wherein —C(O)OCH$_2$Ph is optionally substituted with one or more (C$_1$-C$_6$)alkyl or (C$_1$-C$_6$)alkoxy; $R^{1c}$ is —C(O)O(C$_1$-C$_6$)alkyl wherein —C(O)O(C$_1$-C$_6$)alkyl is optionally substituted with halogen or (C$_1$-C$_6$)alkoxy; and $R^4$ is —SO$_2$(C$_1$-C$_6$)alkyl or —SO$_2$aryl, wherein —SO$_2$(C$_1$-C$_6$)alkyl is optionally substituted with one or more halogen, and wherein —SO$_2$aryl is optionally substituted with one or more halogen, (C$_1$-C$_6$)alkyl or NO$_2$.

In another embodiment there is a method for preparing a compound of formula I:

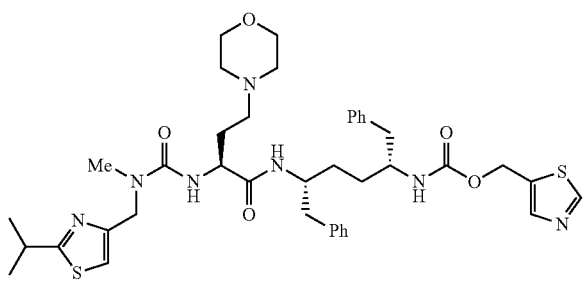

or a salt thereof, comprising converting a compound of formula 10a:

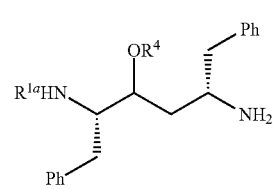

or a salt thereof, into the compound of formula I or the salt thereof, wherein $R^{1a}$ is —C(O)OCH$_2$Ph, wherein —C(O)OCH$_2$Ph is optionally substituted with one or more (C$_1$-C$_6$)alkyl or (C$_1$-C$_6$)alkoxy; and $R^4$ is —SO$_2$(C$_1$-C$_6$)alkyl or —SO$_2$aryl, wherein —SO$_2$(C$_1$-C$_6$)alkyl is optionally substituted with one or more halogen, and wherein —SO$_2$aryl is optionally substituted with one or more halogen, (C$_1$-C$_6$)alkyl or NO$_2$.

In another embodiment there is a method for preparing a compound of formula I:

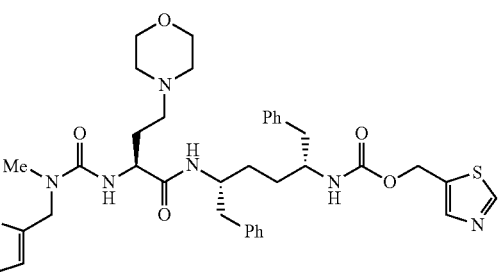

or a salt thereof, comprising converting a compound of formula 11a:

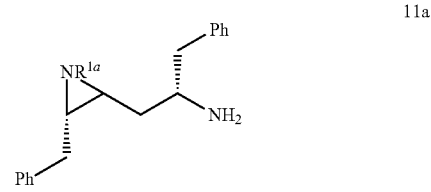

or a salt thereof, into the compound of formula I or the salt thereof, wherein $R^{1a}$ is —C(O)OCH$_2$Ph, wherein —C(O)OCH$_2$Ph is optionally substituted with one or more (C$_1$-C$_6$)alkyl or (C$_1$-C$_6$)alkoxy.

In another embodiment there is a method for preparing a compound of formula I:

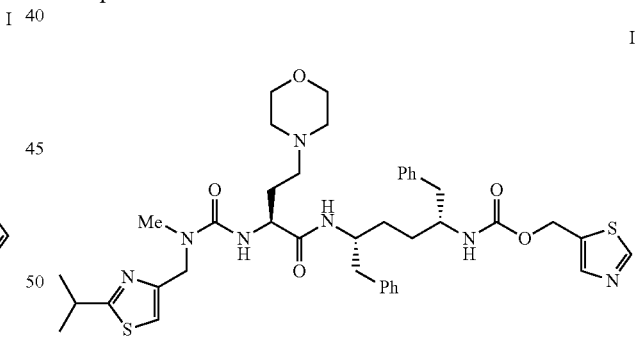

or a salt thereof, comprising converting a compound of formula Va:

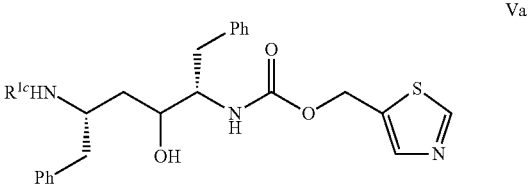

or a salt thereof, into the compound of formula I or the salt thereof, wherein $R^{1c}$ is —C(O)O(C$_1$-C$_6$)alkyl wherein —C(O)O($C_1$-$C_6$)alkyl is optionally substituted with one or more halogen or ($C_1$-$C_6$)alkoxy.

DETAILED DESCRIPTION

The following definitions are used, unless otherwise described:

The term "halo" or "halogen" or "halide" refers to fluoro, chloro, bromo, or iodo.

The terms "alkyl" and "alkoxy" denote both straight and branched groups, but reference to an individual radical such as propyl embraces the straight chain radical, a branched chain isomer such as isopropyl being specifically referred to. The term "($C_1$-$C_6$)alkyl" refers to an alkyl of 1-6 carbon atoms. The term "($C_1$-$C_6$)alkoxy" refers to a ($C_1$-$C_6$)alkyl-O— group.

The term "aryl" as used herein refers to a ring structure of from 6 to 14 carbon atoms in the ring. Aryl includes a single aromatic ring (e.g. phenyl). Aryl also includes multiple condensed rings (e.g. bicyclic or multicyclic rings such as naphthyl or anthryl) wherein the condensed rings may be aromatic, saturated or partially saturated, provided that at least one of the condensed rings is aromatic. Such multiple condensed rings may be optionally substituted with one or more (e.g. 1, 2 or 3) oxo groups on any non-aromatic portion (i.e. saturated or partially unsaturated) of the multiple condensed ring. It is to be understood that the point(s) of attachment of a bicyclic or multicyclic aryl can be at any position of the ring system including an aromatic or non-aromatic portion of the ring. Exemplary aryls include, but are not limited to phenyl, indanyl, naphthyl, 1,2-dihydronaphthyl and 1,2,3,4-tetrahydronaphthyl.

The term "leaving group" includes any group that can be displaced by a nucleophile (e.g. an amine or substituted amine, for example, to form a nitrogen-carbon bond). In one embodiment the leaving group is $OR^4$. In another embodiment the leaving group is —OS(O)$_2R^L$, wherein $R^L$ is ($C_1$-$C_6$)alkyl or aryl, wherein ($C_1$-$C_6$)alkyl is optionally substituted with one or more halogen, and wherein aryl is optionally substituted with one or more halogen, ($C_1$-$C_6$)alkyl or $NO_2$.

The term "Boc" is —C(=O)OC($CH_3$)$_3$.

A protecting group (PG) is a group of atoms introduced into a molecule to prevent it from undergoing undesired chemical reactions. Chemical protecting groups and strategies for protection/deprotection are well known in the art. See e.g., *Protective Groups in Organic Chemistry*, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. An amine protecting group is a protecting group that is particularly well-suited for protecting amine groups. Such amine protecting groups are well-known in the art and are described in *Protective Groups in Organic Chemistry*, Theodora W. Greene, John Wiley & Sons, Inc., New York, 1991. Amine protecting groups include but are not limited to carbamates (e.g. ($C_1$-$C_6$)alkyl and arylmethyl (e.g. benzyl) carbamates each optionally substituted with one or more ($C_1$-$C_6$)alkoxy, ($C_1$-$C_6$)alkyl and halo groups), trityl groups (e.g. C(aryl) or $CPh_3$ each optionally substituted with one or more ($C_1$-$C_6$)alkoxy, ($C_1$-$C_6$)alkyl and halo groups), arylalkyl groups (e.g. arylmethyl and benzyl groups optionally substituted with one or more ($C_1$-$C_6$)alkoxy, ($C_1$-$C_6$)alkyl and halo groups) and silyl groups (e.g. —$SiR_3$ groups wherein each $R^3$ is independently ($C_1$-$C_6$)alkyl or aryl, each optionally substituted with one or more ($C_1$-$C_6$)alkoxy, ($C_1$-$C_6$)alkyl and halo groups).

It will be appreciated by those skilled in the art that a compound having a chiral center may exist in and be isolated in optically active and racemic forms. Some compounds may exhibit polymorphism. It is to be understood that the following description can encompass processes for preparing racemic, diastereomeric, optically-active, polymorphic, tautomeric, or stereoisomeric form, or mixtures thereof, of a compound described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

It is also to be understood that compounds depicted herein may or may not be shown with absolute stereochemistry. If a compound is drawn with stereochemical bonds it is meant to be the specific stereoisomer shown (e.g diastereomer or enantiomer). Accordingly, wherein applicable, in one embodiment the stereoisomer of a compound depicted herein is about >99% enriched in that stereoisomer. In another embodiment the stereoisomer of a compound depicted herein is about >98% enriched in that stereoisomer. In another embodiment the stereoisomer of a compound depicted herein is about >95% enriched in that stereoisomer. In another embodiment the stereoisomer of a compound depicted herein is about >90% enriched in that stereoisomer. In another embodiment the stereoisomer of a compound depicted herein is about >80% enriched in that stereoisomer. In another embodiment the stereoisomer of a compound depicted herein is about >70% enriched in that stereoisomer. In another embodiment the stereoisomer of a compound depicted herein is about >60% enriched in that stereoisomer. In another embodiment the stereoisomer of a compound depicted herein is about >50% enriched in that stereoisomer.

Specific values listed below for radicals, substituents, and ranges, are for illustration only; they do not exclude other defined values or other values within defined ranges for the radicals and substituents.

Specifically, ($C_1$-$C_6$)alkyl can be methyl, ethyl, propyl, isopropyl, butyl, iso-butyl, sec-butyl, pentyl, 3-pentyl or hexyl; ($C_1$-$C_6$)alkoxy can be methoxy, ethoxy, propoxy, isopropoxy, butoxy, iso-butoxy, sec-butoxy, pentoxy or hexyloxy, heptyloxy.

A specific group of compounds includes compounds wherein $R^{1a}$ and $R^{1b}$ are each independently —C(O)O—$CH_2Ph$, —C(O)O($C_1$-$C_6$)alkyl or Ph-$CH_2$—; or $R^{1a}$ is —C(O)O—$CH_2Ph$, —C(O)O($C_1$-$C_6$)alkyl or Ph-$CH_2$— and $R^{1b}$ is H; wherein any C(O)O—$CH_2Ph$, —C(O)O($C_1$-$C_6$) alkyl or Ph-$CH_2$— of $R^{1a}$ and $R^{1b}$ is optionally substituted with one or more ($C_1$-$C_6$)alkyl or ($C_1$-$C_6$)alkoxy.

Another specific group of compounds includes wherein $R^{1a}$ is —C(O)O—$CH_2Ph$ and $R^{1b}$ is H, wherein —C(O)O—$CH_2Ph$ is optionally substituted with one or more ($C_1$-$C_6$) alkyl or ($C_1$-$C_6$)alkoxy.

Another specific group of compounds includes wherein $R^{1a}$ is —C(O)O—$CH_2Ph$ and $R^{1b}$ is H.

A specific value for $R^{1a}$ is —C(O)O—$CH_2Ph$ wherein —C(O)O—$CH_2Ph$ is optionally substituted with one or more ($C_1$-$C_6$)alkyl or ($C_1$-$C_6$)alkoxy.

Another specific value for $R^{1a}$ is —C(O)O—$CH_2Ph$.

A specific value for $R^{1b}$ is H.

A specific value for $R^{1c}$ is —C(O)OC($CH_3$)$_3$.

A specific value for $R^4$ is p-toluenesulfonyl.

In one embodiment there is a compound which is:

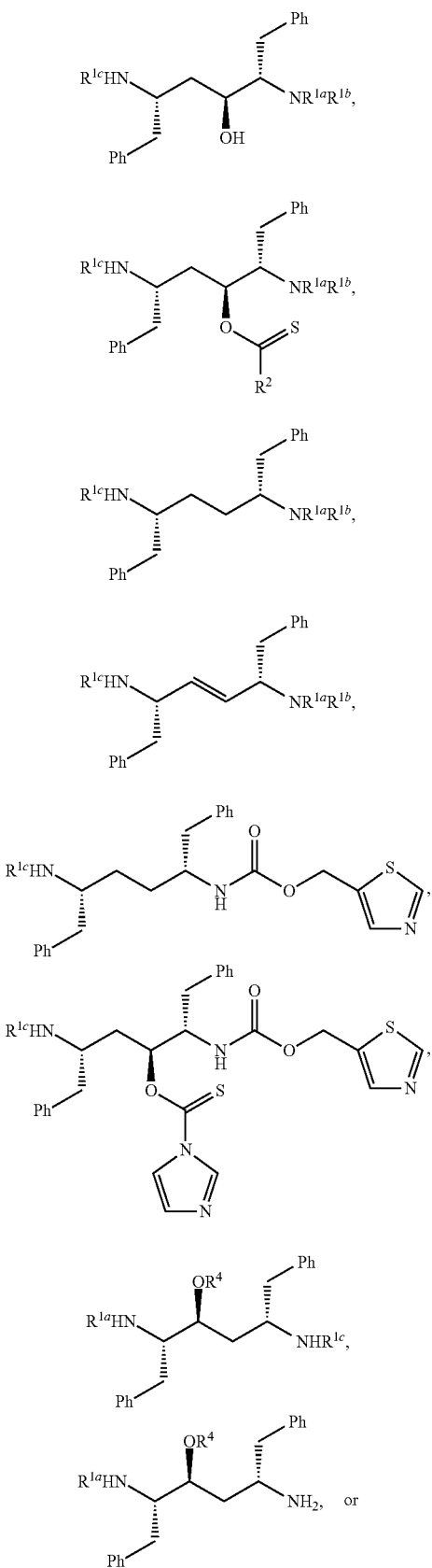

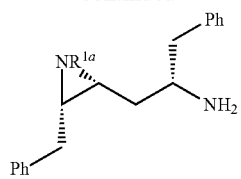

wherein:

$R^{1a}$ and $R^{1b}$ are each independently an amine protecting group; or $R^{1a}$ is an amine protecting group and $R^{1b}$ is H;

$R^{1c}$ is —C(O)O($C_1$-$C_6$)alkyl wherein —C(O)O($C_1$-$C_6$)alkyl is optionally substituted with halogen or ($C_1$-$C_6$)alkoxy $R^2$ is SMe or imidazol-1-yl; and $R^4$ is —$SO_2$($C_1$-$C_6$)alkyl or —$SO_2$aryl, wherein —$SO_2$($C_1$-$C_6$)alkyl is optionally substituted with one or more halogen, and wherein —$SO_2$aryl is optionally substituted with one or more halogen, ($C_1$-$C_6$)alkyl or $NO_2$;

or a salt thereof;

provided the compound is not:

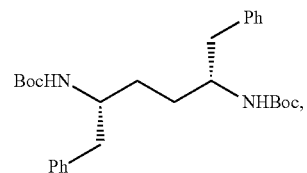

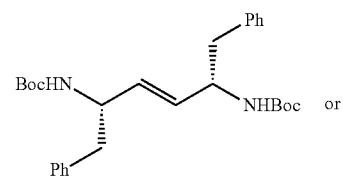

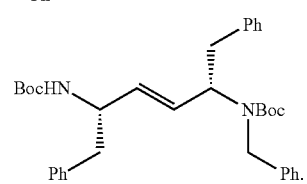

In another embodiment there is a compound which is:

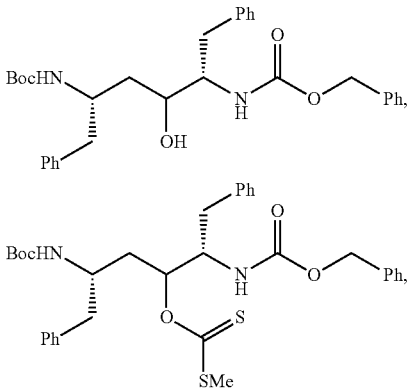

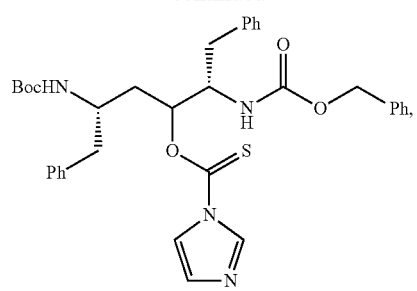
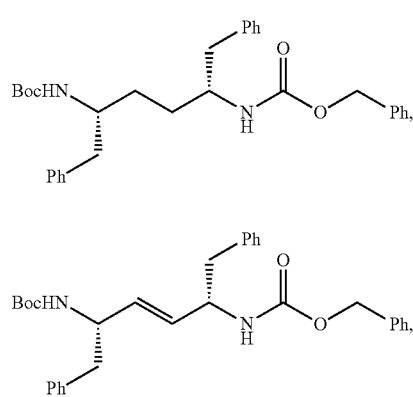
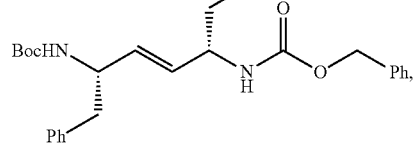
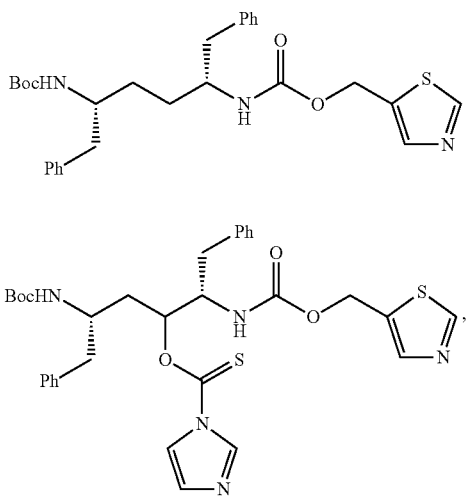
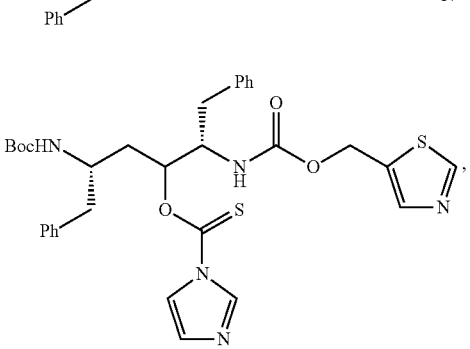
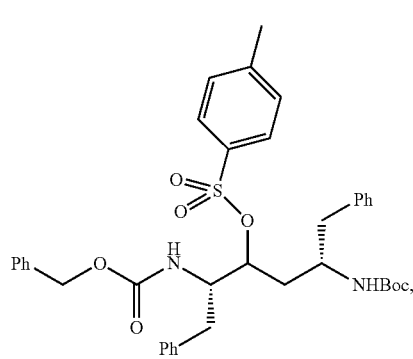
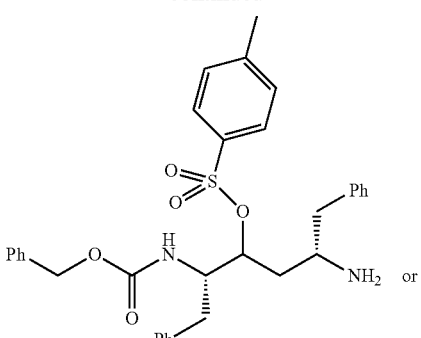
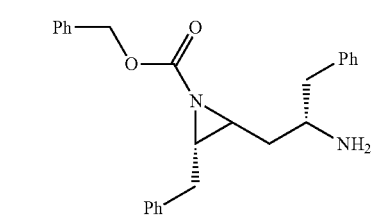
or a salt thereof.
In another embodiment there is a compound which is:
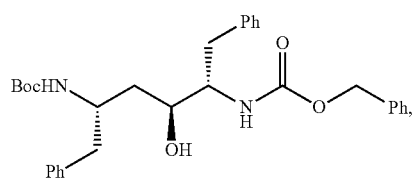
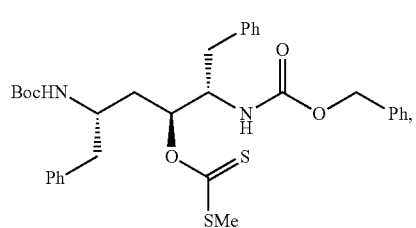
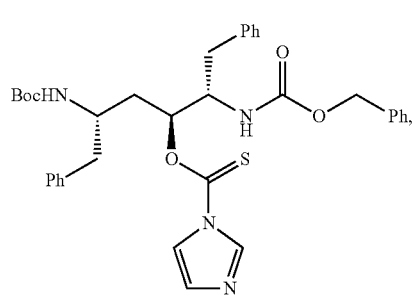
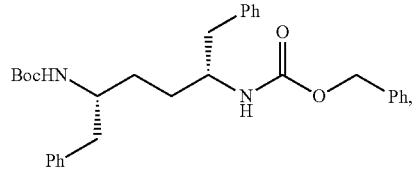

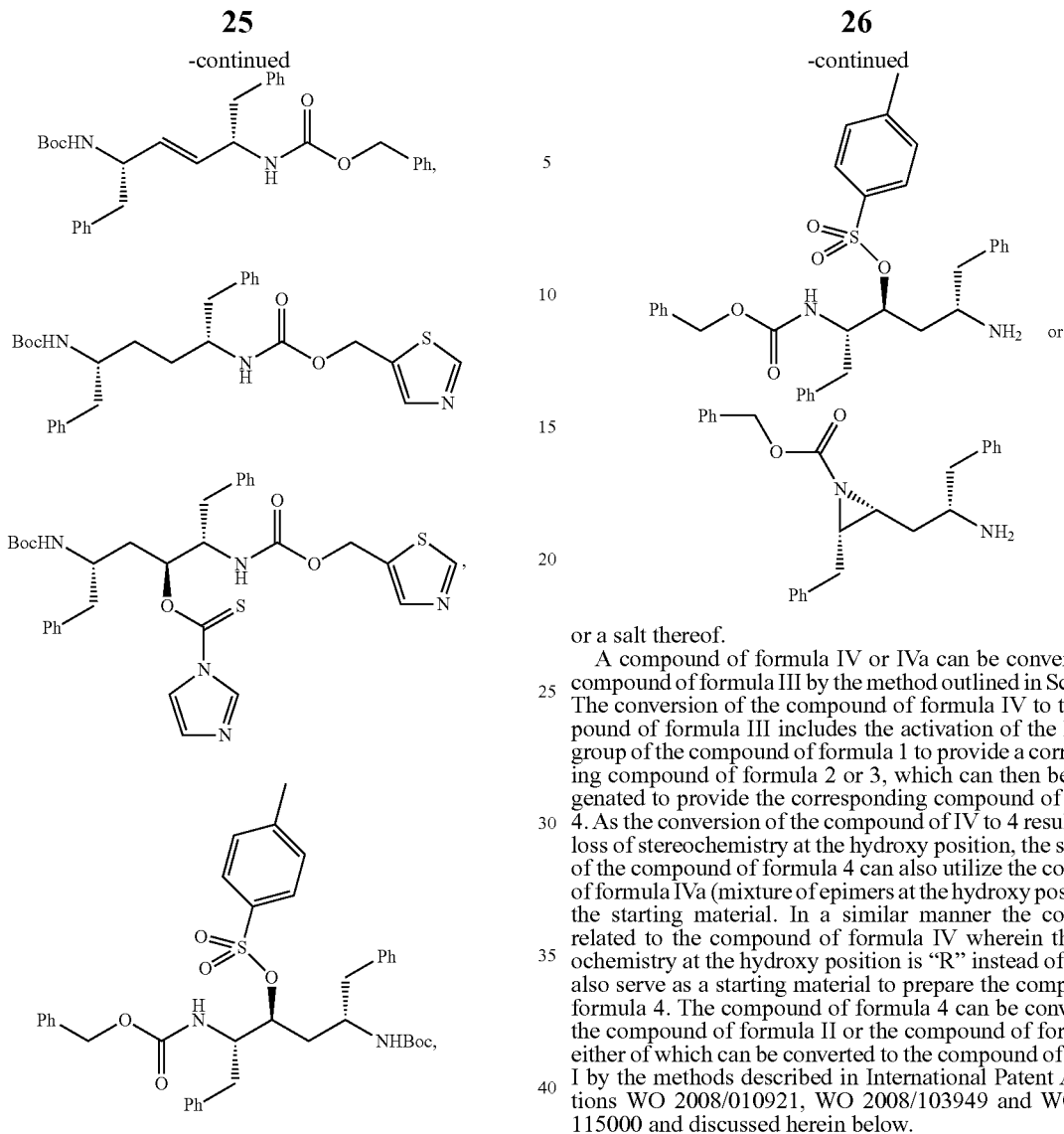

or a salt thereof.

A compound of formula IV or IVa can be converted to a compound of formula III by the method outlined in Scheme 1. The conversion of the compound of formula IV to the compound of formula III includes the activation of the hydroxy group of the compound of formula 1 to provide a corresponding compound of formula 2 or 3, which can then be deoxygenated to provide the corresponding compound of formula 4. As the conversion of the compound of IV to 4 results in the loss of stereochemistry at the hydroxy position, the synthesis of the compound of formula 4 can also utilize the compound of formula IVa (mixture of epimers at the hydroxy position) as the starting material. In a similar manner the compound related to the compound of formula IV wherein the stereochemistry at the hydroxy position is "R" instead of "S" can also serve as a starting material to prepare the compound of formula 4. The compound of formula 4 can be converted to the compound of formula II or the compound of formula III either of which can be converted to the compound of formula I by the methods described in International Patent Applications WO 2008/010921, WO 2008/103949 and WO 2010/115000 and discussed herein below.

Scheme 1

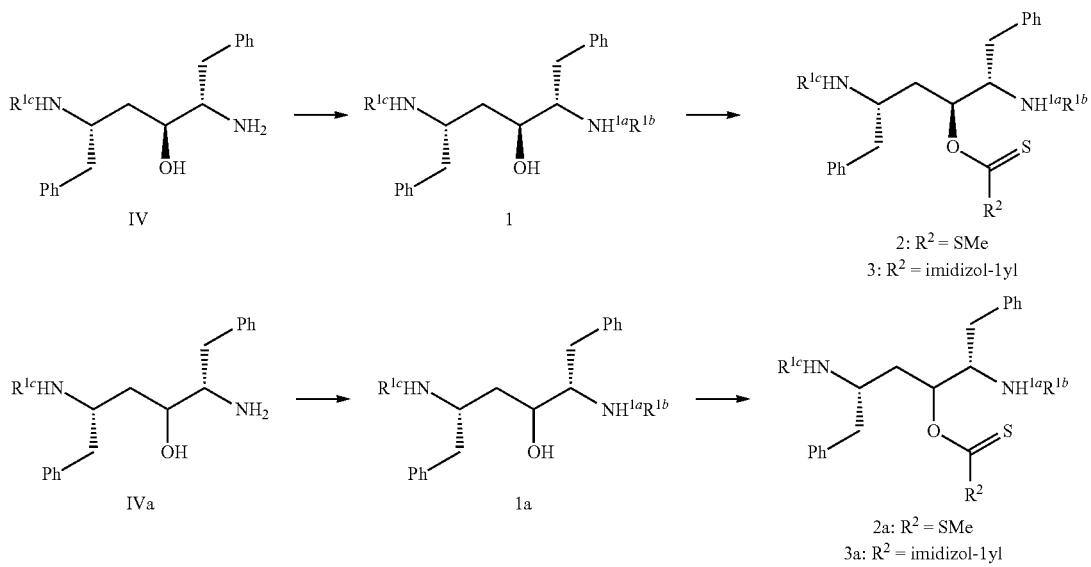

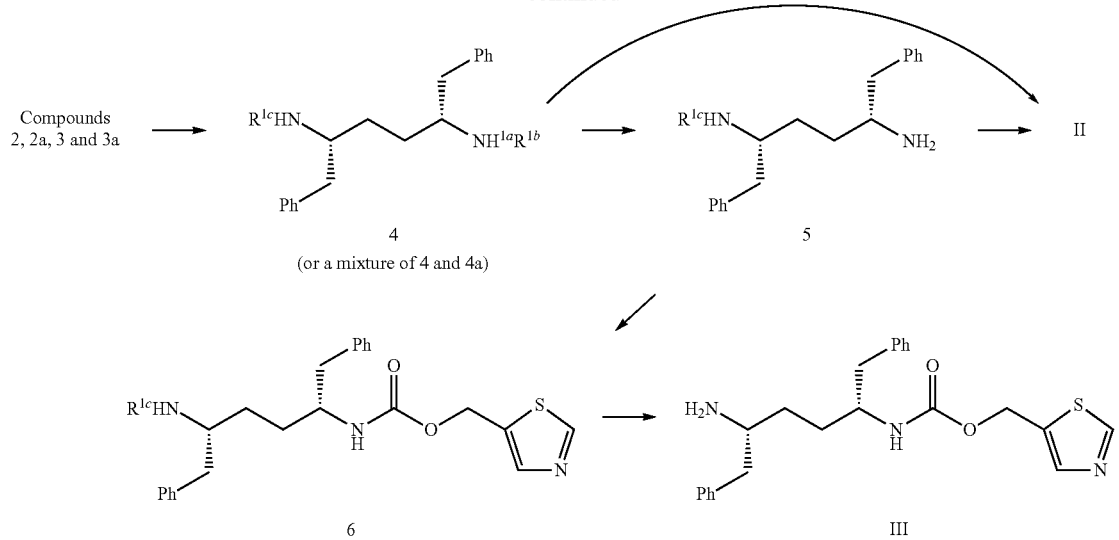

(or a mixture of 4 and 4a)

Preparation of a Compound of Formula 1 or 1a:

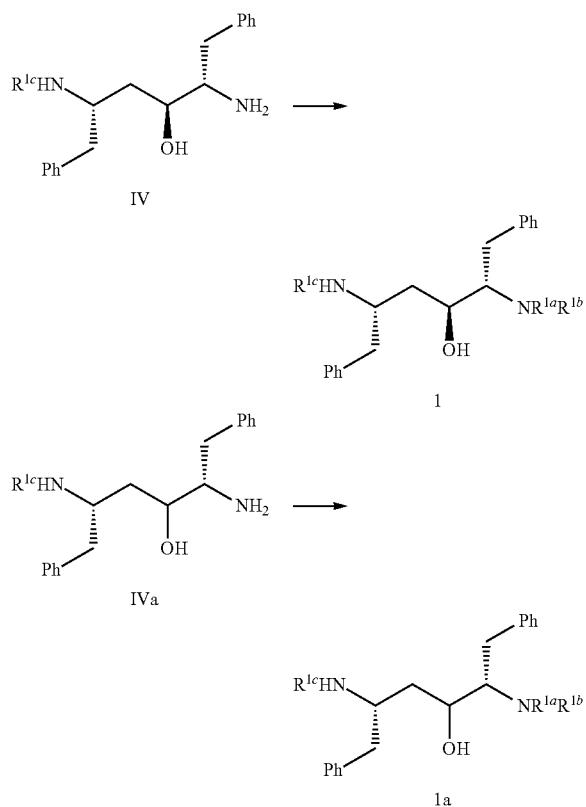

In one embodiment there is a method of protecting a compound of formula IV (or IVa) or a salt thereof to provide a corresponding compound of formula 1 (or 1a) or a salt thereof, wherein $R^{1a}$ and $R^{1b}$ are each independently an amine protecting group, or $R^{1a}$ is an amine protecting group and $R^{1b}$ is H; and $R^{1c}$ is —C(O)O($C_1$-$C_6$)alkyl wherein —C(O)O($C_1$-$C_6$)alkyl is optionally substituted with one or more halogen or ($C_1$-$C_6$)alkoxy.

A specific value for $R^{1c}$ is —C(O)OC($CH_3$)$_3$. A specific group of compounds of formula I or Ia are compounds wherein $R^{1a}$ or $R^{1b}$ are each independently —C(O)O—$CH_2$Ph, —C(O)O($C_1$-$C_6$)alkyl or Ph-$CH_2$—, wherein any C(O)O—$CH_2$Ph, —C(O)O($C_1$-$C_6$)alkyl or Ph-$CH_2$— of $R^{1a}$ and $R^{1b}$ is optionally substituted with one or more ($C_1$-$C_6$)alkyl or ($C_1$-$C_6$)alkoxy. Another specific group of compounds of formula I or Ia are compounds wherein $R^{1a}$ is —C(O)O—$CH_2$Ph, —C(O)O($C_1$-$C_6$)alkyl or Ph-$CH_2$— and $R^{1b}$ is H, wherein any —C(O)O—$CH_2$Ph, —C(O)O($C_1$-$C_6$)alkyl or Ph-$CH_2$— of $R^{1a}$ is optionally substituted with one or more ($C_1$-$C_6$)alkyl or ($C_1$-$C_6$)alkoxy. Another specific group of compounds of formula I or Ia are compounds wherein $R^{1a}$ is —C(O)O—$CH_2$Ph and $R^{1b}$ is H, wherein any —C(O)O—$CH_2$Ph, of $R^{1a}$ is optionally substituted with one or more ($C_1$-$C_6$)alkyl or ($C_1$-$C_6$)alkoxy. Another specific group of compounds of formula I or Ia are compounds wherein $R^{1a}$ is —C(O)O—$CH_2$Ph and $R^{1b}$ is H. These specific values are also specific values for the embodiments described herein below for the chemistry of Scheme 1.

The compound of formula IV or IVa, or salts thereof can be protected by any suitable amine protecting group (or groups) under standard conditions to provide the corresponding compound of formula 1 or 1a, respectively, or salts thereof. The amine can be protected with one group wherein $R^{1a}$ is an amine protecting group and $R^{1b}$ is H or the amine can be protected with two groups wherein $R^{1a}$ and $R^{1b}$ are both amine protecting groups wherein the two groups can be the same or different. A variety of suitable reagents are readily available to protect the amine of the compound of formula IV or IVa to provide the corresponding compound of formula 1 or 1a. For example, a carbamate group (e.g. a Cbz group) can be introduced by means of a Cbz-halide reagent and a benzyl group can be introduced by a benzyl halide reagent. The reaction can be carried out in a variety of suitable solvents or mixtures thereof. Additional reagents may be suitable for a particular protection step such as the inclusion of a suitable base (e.g. an inorganic base such as a metal hydroxide or a metal carbonate or an organic base such as a trialkylamine). The reaction can conveniently be carried out at a temperature from about 0° C. to 25° C.

In another embodiment there is a method for the conversion of a compound of formula 1 or a salt thereof or a compound of formula Ia or a salt thereof to a compound of formula I or a salt thereof comprising:

a) converting the compound of formula 1 or the compound of formula 1a or salts thereof; to the compound of formula II or the compound of formula III or salts thereof by the steps outlined in Scheme 1 and described herein below; and b) converting the compound of formula II or the compound of formula III or salts thereof to the compound of formula I or the salt thereof by any of the steps outlined in Schemes 4-12 and described herein below.

Preparation of a Compound of Formula 2 or 2a:

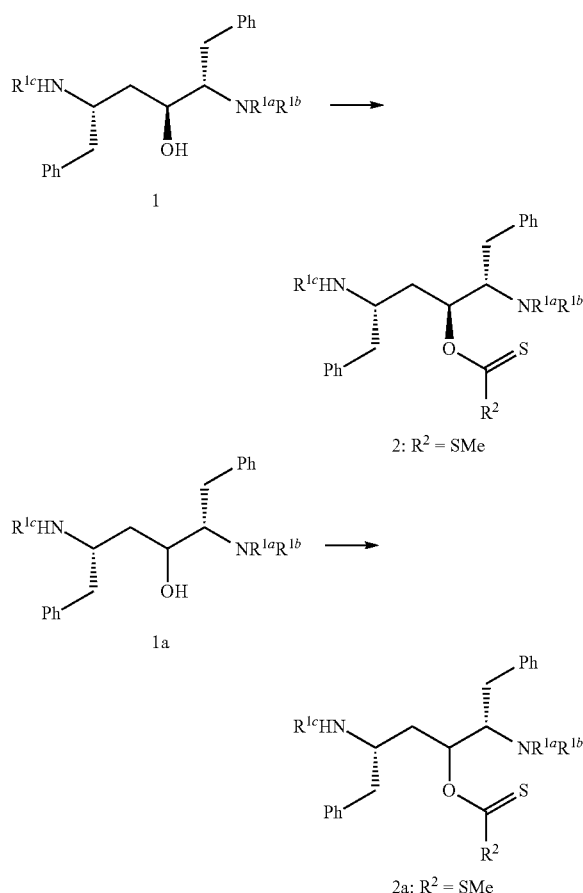

In another embodiment there is a method for the conversion of a compound of formula 2 or a salt thereof or a compound of formula 2a or a salt thereof to a compound of formula I or a salt thereof comprising:

a) converting the compound of formula 2 or the compound of formula 2a or salts thereof, to the compound of formula II or the compound of formula III or salts thereof by the steps outlined in Scheme 1 and described herein below; and b) converting the compound of formula II or the compound of formula III or salts thereof to the compound of formula I or the salt thereof by any of the steps outlined in Schemes 4-12 and described herein below.

Preparation of a Compound of Formula 3 or 3a:

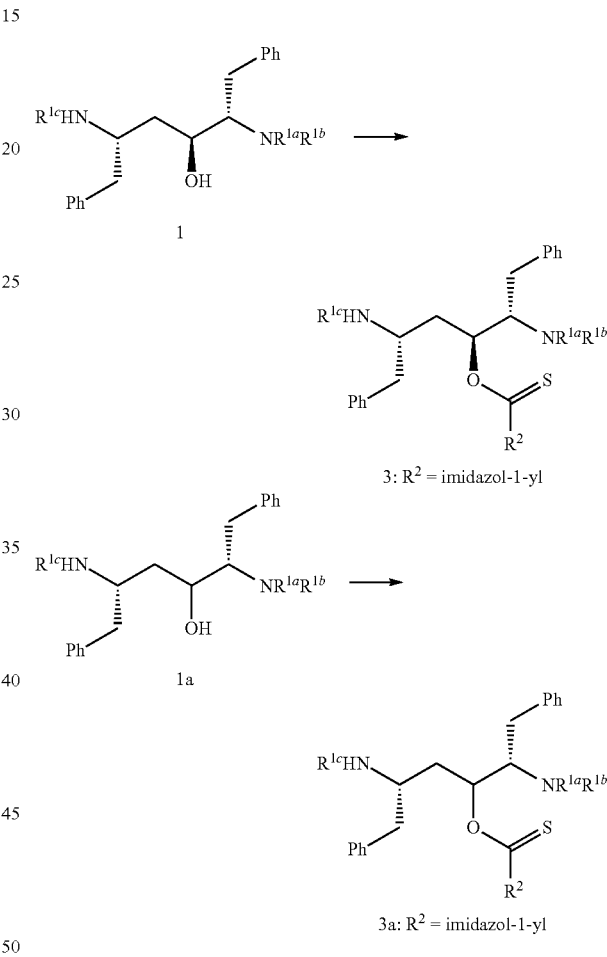

In one embodiment there is a method for activating a compound of formula 1 (or 1a) or a salt thereof to provide a corresponding compound of formula 2 (or 2a) or a salt thereof, wherein $R^{1a}$ and $R^{1b}$ are each independently an amine protecting group, or $R^{1a}$ is an amine protecting group and $R^{1b}$ is H; $R^{1c}$ is —C(O)O($C_1$-$C_6$)alkyl wherein —C(O)O($C_1$-$C_6$)alkyl is optionally substituted with one or more halogen or ($C_1$-$C_6$)alkoxy; and $R^2$ is —SMe.

The compound of formula 1 or 1a or salts thereof can be activated to provide the corresponding compound of formula 2 or 2a or salts thereof, wherein $R^2$ is —SMe, by the treatment of the compound of formula 1 or 1a with a base (e.g. a metal hydride such as NaH), carbon disulfide (i.e. $CS_2$) and a methylating reagent (e.g. a methylhalide or methylsulfonate). Suitable solvents include organic solvents such as polar aprotic solvents (e.g. THF). The reaction can conveniently be carried out at a temperature from about 0° C. to 25° C.

In one embodiment there is a method for activating a compound of formula 1 (or 1a) or a salt thereof to provide a corresponding compound of formula 3 (or 3a) or a salt thereof, wherein $R^{1a}$ and $R^{1b}$ are each independently an amine protecting group, or $R^{1a}$ is an amine protecting group and $R^{1b}$ is H; $R^{1c}$ is —C(O)O($C_1$-$C_6$)alkyl wherein —C(O)O($C_1$-$C_6$)alkyl is optionally substituted with one or more halogen or ($C_1$-$C_6$)alkoxy; and $R^2$ is imidazol-1-yl.

The compound of formula 1 or 1a or salts thereof can be activated to provide the compound of formula 3 or 3a or salts thereof; wherein $R^2$ is imidazol-1-yl, by the treatment of the compound of formula 1 or 1a with thiocarbonyldiimidazole and imidazole. Suitable solvents include organic solvents such as polar aprotic solvents (e.g. THF). The reaction can conveniently be carried out at a temperature from about 0° C. to 25° C.

In another embodiment there is a method for the conversion of a compound of formula 3 or a salt thereof or a compound of formula 3a or a salt thereof to a compound of formula I or a salt thereof comprising:

a) converting the compound of formula 3 or the compound of formula 3a or salts thereof; to the compound of formula II or the compound of formula III or salts thereof by the steps outlined in Scheme 1 and described herein below; and b) converting the compound of formula II or the compound of formula III or salts thereof to the compound of formula I or the salt thereof by any of the steps outlined in Schemes 4-12 and described herein below.

Preparation of a Compound of Formula 4:

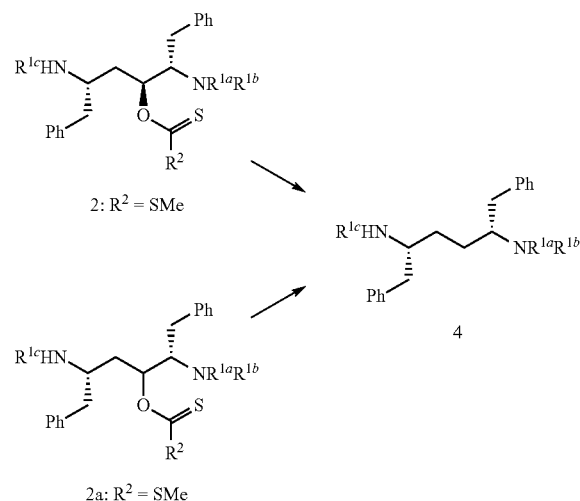

In one embodiment there is a method for deoxygenating a compound of formula 2 (or 2a) or a salt thereof to provide a corresponding compound of formula 4 or a salt thereof; wherein $R^{1a}$ and $R^{1b}$ are each independently an amine protecting group, or $R^{1a}$ is an amine protecting group and $R^{1b}$ is H; $R^{1c}$ is —C(O)O(C$_1$-C$_6$)alkyl wherein —C(O)O(C$_1$-C$_6$)alkyl is optionally substituted with one or more halogen or (C$_1$-C$_6$)alkoxy; and $R^2$ is —SMe.

A compound of formula 2 or 2a wherein $R^2$ is —SMe or a salt thereof, can be deoxygenated to provide a corresponding compound of formula 4 wherein $R^2$ is —SMe, by the treatment of the compound of formula 2 or 2a with a hydrogen bond donor (e.g. 1-ethylpiperidine hypophosphate, diethyl phosphite, tributylboron/water) and a radical initiator (e.g. benzoyl peroxide, air). Suitable solvents include organic solvents such as polar and non-polar aprotic solvents (e.g. dioxane, toluene). The reaction can conveniently be carried out at a temperature from about 95° C. to 105° C.

The conversion of 2 or 2a to 4 as described above can also result in the formation of the corresponding unsaturated compound of formula 4a, depending on the nature of the protecting groups on the nitrogen and the reagents/conditions used in the deoxygenation step.

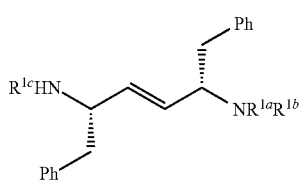

The olefin can be separated from the compound of formula 4 and reduced to provide the saturated compound (i.e. the compound of formula 4) by a variety of well-known hydrogenation procedures. During the reduction step one or more protecting groups may also be removed. The reduction of the compound of formula 4a can also be carried out without separating the compound of formula 4a from the compound of formula 4 (i.e. reducing the mixture of the compound of formula 4a and the compound of formula 4 to provide the compound of formula 4 or a compound wherein the olefin has been reduced and one or more protecting groups have been removed).

In another embodiment there is a method for the conversion of a compound of formula 4 or a salt thereof to a compound of formula I or a salt thereof comprising:

a) converting the compound of formula 4 or a salt thereof, to the compound of formula II or the compound of formula III or salts thereof by the steps outlined in Scheme 1 and described herein below; and b) converting the compound of formula II or the compound of formula III or salts thereof to the compound of formula I or the salt thereof by any of the steps outlined in Schemes 4-12 and described herein below.

Preparation of a Compound of Formula 4:

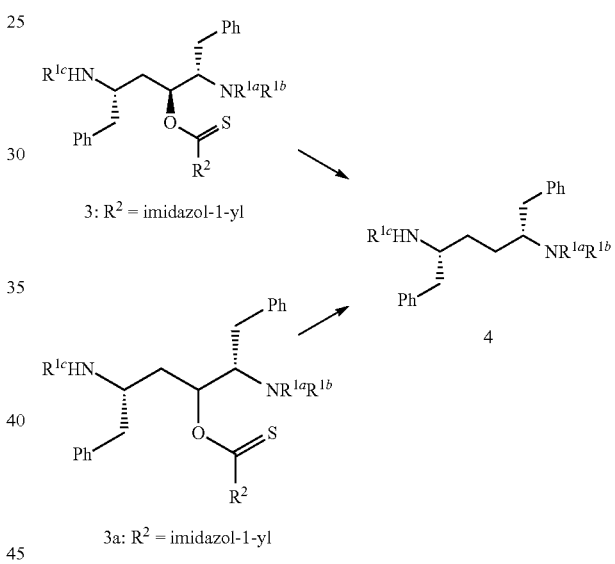

In one embodiment there is a method for deoxygenating a compound of formula 3 (or 3a) or a salt thereof to provide a corresponding compound of formula 4 or a salt thereof wherein $R^{1a}$ and $R^{1b}$ are each independently an amine protecting group, or $R^{1a}$ is an amine protecting group and $R^{1b}$ is H; $R^{1c}$ is —C(O)O(C$_1$-C$_6$)alkyl wherein —C(O)O(C$_1$-C$_6$)alkyl is optionally substituted with one or more halogen or (C$_1$-C$_6$)alkoxy; and $R^2$ is imidazol-1-yl.

A compound of formula 3 or 3a wherein $R^2$ is imidazol-1-yl, or a salt thereof, can be deoxygenated to provide a corresponding compound of formula 4, by the treatment of the compound of formula 3 or 3a with a suitable radical source and a suitable radical initiator. Suitable radical sources include trialkyltin hydrides (e.g. tri-n-butyltin hydride), trialkylsilanes (e.g. triethyl silane), dialkyl phosphites (e.g. dimethyl phosphite, diethyl phosphite, di-t-butyl phosphite, di-isopropyl phosphite and ethylene glycol phosphite), trialkylborons (e.g. tributylboron) with water, and amine salts of hypophosphorus (e.g. diisopropylethylammonium salt of hypophosphorus acid). Suitable radical initiators include AIBN, benzoyl peroxide and air. The reaction can be conveniently carried out in a variety or organic solvents including polar and non-polar aprotic solvents (e.g. dioxane, n-butyl acetate, di-n-butyl ether, diethyl carbonate, diethoxy ethane, toluene, methylcyclohexane and heptanes). The reaction can conveniently be carried out at a temperature from about 95° C. to 105° C.

The conversion of 3 or 3a to 4 as described above can also result in the formation of the corresponding unsaturated compound of formula 4a (as described for the conversion of 2 to 4 above) depending on the nature of the protecting groups on the nitrogen and the reagents/conditions used in the deoxygenation step. The compound 4a or the mixture of the compound of formula 4 and formula 4a can be treated in the same manner as described for the conversion or 2 to 4.

In another embodiment there is a method for the conversion of a compound of formula 4 or a salt thereof to a compound of formula I or a salt thereof comprising:

a) converting the compound of formula 4 or a salt thereof, to the compound of formula II or the compound of formula III or salts thereof by the steps outlined in Scheme 1 and described herein below; and b) converting the compound of formula II or the compound of formula III or salts thereof to the compound of formula I or the salt thereof by any of the steps outlined in Schemes 4-12 and described herein below.

Preparation of a Compound of Formula 5:

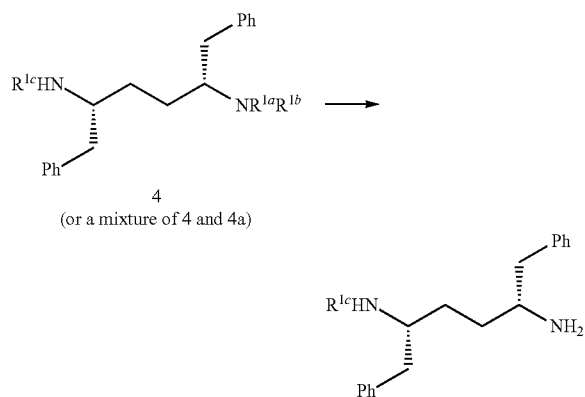

4
(or a mixture of 4 and 4a)

5

In one embodiment there is a method for deprotecting a compound of formula 4 or a salt thereof to provide a corresponding compound of formula 5 or a salt thereof, wherein $R^{1a}$ and $R^{1b}$ are each independently an amine protecting group, or $R^{1a}$ is an amine protecting group and $R^{1b}$ is H; and $R^{1c}$ is —C(O)O(C$_1$-C$_6$)alkyl wherein —C(O)O(C$_1$-C$_6$)alkyl is optionally substituted with one or more halogen or (C$_1$-C$_6$)alkoxy.

The compound of formula 4 or a salt thereof can be deprotected to provide the corresponding compound of formula 5 or a salt thereof, by the treatment of the compound of formula 4 with an appropriate deprotection reagent. For example, when $R^{1a}$ is a benzyl carbamate amine protecting group the deprotection can be carried out under hydrogenation conditions. Suitable catalysts include palladium on carbon. Suitable solvents include organic solvents such as polar protic solvents (e.g. ethanol). The reaction can conveniently be carried out at a temperature from about 0° C. to 60° C.

In another embodiment there is a method for the conversion of a compound of formula 5 or a salt thereof to a compound of formula I or a salt thereof comprising:

a) converting the compound of formula 5 or the or the salts thereof, to the compound of formula II or the compound of formula III or salts thereof by the steps outlined in Scheme 1 and described herein below; and b) converting the compound of formula II or the compound of formula III or salts thereof to the compound of formula I or the salt thereof by any of the steps outlined in Schemes 4-12 and described herein below.

Preparation of a Compound of Formula II:

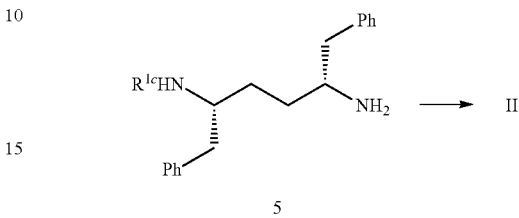

5

In one embodiment there is a method for deprotecting a compound of formula 5 or a salt thereof to provide the compound of formula II or a salt thereof, wherein $R^{1c}$ is —C(O)O(C$_1$-C$_6$)alkyl wherein —C(O)O(C$_1$-C$_6$)alkyl is optionally substituted with one or more halogen or (C$_1$-C$_6$)alkoxy.

The compound of formula 5 or a salt thereof can be deprotected to provide the compound of formula II or a salt thereof, by the treatment of the compound of formula 5 with an appropriate deprotection reagent. For example, when $R^{1c}$ is —OC(=O)O(CH)$_3$ the deprotection can be carried by treatment of the compound of formula 5 with an acid. Suitable acids include mineral acids (e.g. hydrochloric acid) and organic acids (e.g. TFA). Suitable solvents include organic solvents such as polar protic solvents (e.g. ethanol) and aprotic solvents (e.g. methylene chloride). The reaction can conveniently be carried out at a temperature from about 0° C. to 22° C.

In another embodiment, (subsequent to the conversion of 5 to II), there is a method for the conversion of a compound of formula II or a salt thereof to a compound of formula I or a salt thereof comprising converting the compound of formula II or the salt thereof to the compound of formula I or the salt thereof by any of the steps outlined in Schemes 4-12 and described herein below.

Preparation of a Compound of Formula 6:

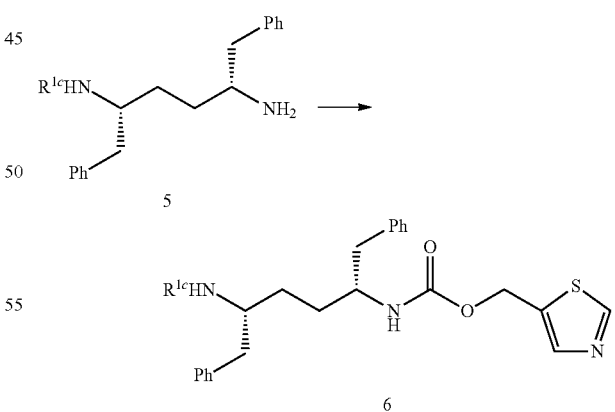

In one embodiment there is a method for acylating a compound of formula 5 or a salt thereof to provide a corresponding compound of formula 6 or a salt thereof; wherein $R^{1c}$ is —C(O)O(C$_1$-C$_6$)alkyl wherein —C(O)O(C$_1$-C$_6$)alkyl is optionally substituted with halogen or (C$_1$-C$_6$)alkoxy.

The compound of formula 5 or a salt thereof can be acylated to provide the corresponding compound of formula 6 or a salt thereof, by the treatment of the compound of formula 5 with a compound of formula VIII, or a salt thereof (as described herein below) in the presence of a suitable base in a suitable solvent. Suitable bases include carbonate bases (e.g. potassium carbonate) and trialkylamines (e.g. diisopropylethylamine, or N-methyl morpholine). Suitable solvents include solvents such as dichloromethane, tetrahydrofuran, 1,2-dichloroethane, isopropylacetate, and diethylether, and mixtures thereof. The reaction can conveniently be carried out at a temperature from about 0° C. to 22° C.

In another embodiment there is a method for the conversion of a compound of formula 6 or a salt thereof to a compound of formula I or a salt thereof comprising:

a) deprotecting the compound of formula 6 or the salt thereof, to the compound of formula III or the salt thereof by the steps outlined in Scheme 1 and Scheme 2 and described herein below; and b) converting the compound of formula III or the salt thereof to the compound of formula I or the salt thereof by any of the steps outlined in Schemes 5-12 and described herein below.

A compound of formula V or Va can be converted to a compound of formula 6 by the method outlined in Scheme 2. The conversion of the compound of formula V to the compound of formula 6 includes the activation of the hydroxy group of the compound of formula V to provide a compound of formula 7 that can then be deoxygenated to provide the compound of formula 6. As the conversion of the compound of formula V to 6 results in the loss of stereochemistry at the hydroxy position, the synthesis of the compound of formula 6 can also utilize the compound of formula Va (mixture of epimers at the hydroxy position) as the starting material. In a similar manner the compound related to the compound of formula V wherein the stereochemistry at the hydroxy position is "R" instead of "S" can also serve as a starting material to prepare the compound of formula 6. The compound of formula 6 can be converted to the compound of formula III. The compound of formula III can be converted to the compound of formula I by the methods described in International Patent Applications WO 2008/010921, WO 2008/103949 and WO 2010/115000 and discussed herein below.

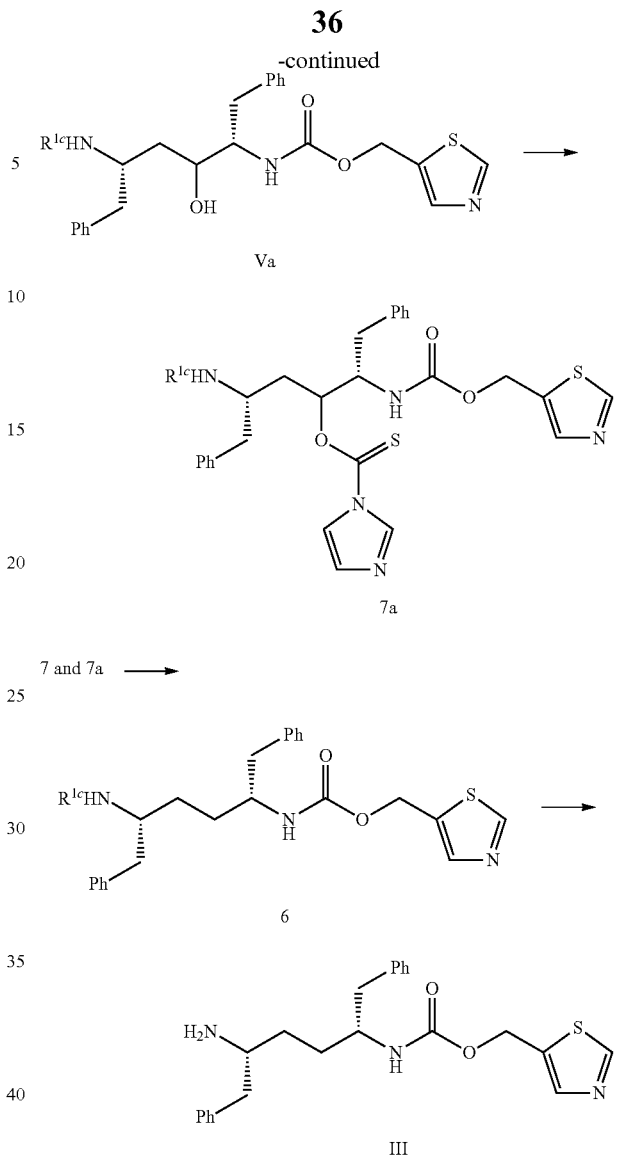

Preparation of a Compound of Formula 7 or 7a:

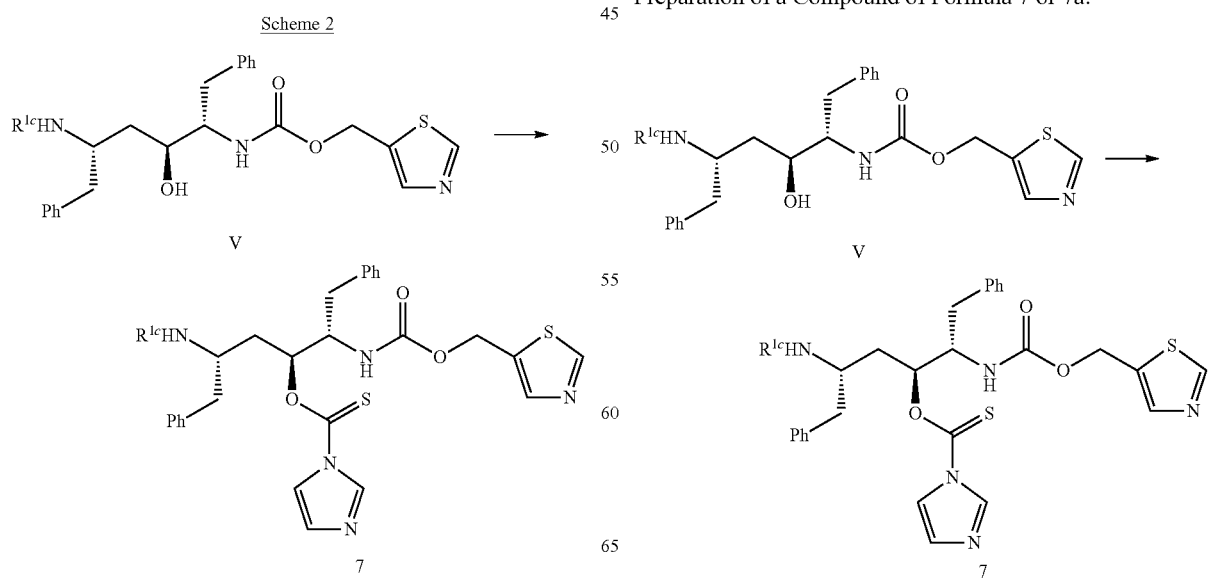

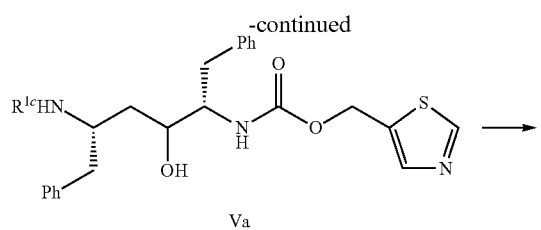

Va

[structure 7a]

In one embodiment there is a method for activating a compound of formula V (or Va) or a salt thereof to provide a corresponding compound of formula 7 (or 7a) or a salt thereof, wherein $R^{1c}$ is —C(O)O($C_1$-$C_6$)alkyl wherein —C(O)O($C_1$-$C_6$)alkyl is optionally substituted with one or more halogen or ($C_1$-$C_6$)alkoxy.

A specific value for $R^{1c}$ is —C(O)OC(CH$_3$)$_3$. This specific value is also a specific value for the embodiments described herein below for the chemistry of Scheme 2.

The compound of formula V or Va or salts thereof can be activated to provide the compound of formula 7 or 7a, or salts thereof, by the treatment of the compound of formula V or Va with thiocarbonyldiimidazole and imidazole. Suitable solvents include organic solvents such as polar aprotic solvents (e.g. THF). The reaction can conveniently be carried out at a temperature from about 0° C. to 25° C.

In another embodiment there is a method for the conversion of a compound of formula 7 or a salt thereof or a compound of formula 7a or a salt thereof to a compound of formula 1 or a salt thereof comprising:

a) converting the compound of formula 7 or the compound of formula 7a or the salts thereof, to the compound of formula III or the salt thereof by the steps outlined in Scheme 2 and described herein below; and b) converting the compound of formula III or the salt thereof to the compound of formula I or the salt thereof by any of the steps outlined in Schemes 5-12 and described herein below.

Preparation of a Compound of Formula 6:

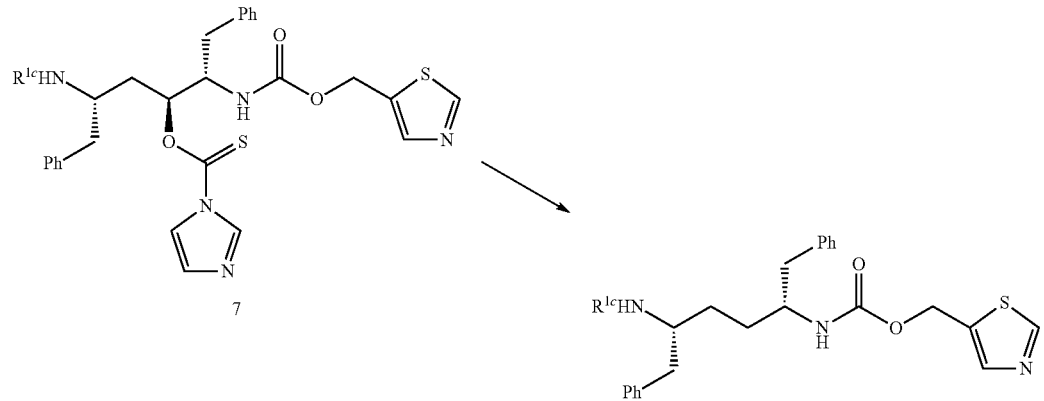

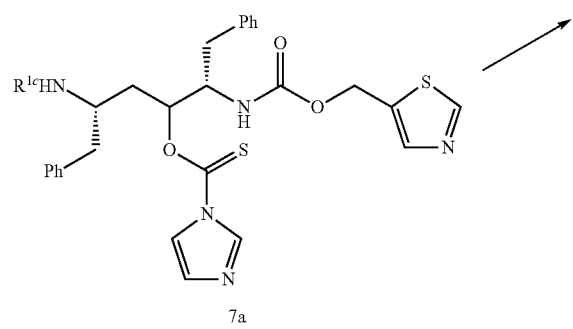

In one embodiment there is a method for deoxygenating a compound of formula 7 (or 7a) or a salt thereof to provide a corresponding compound of formula 6 or a salt thereof, wherein $R^{1c}$ is —C(O)O($C_1$-$C_6$)alkyl wherein —C(O)O($C_1$-$C_6$)alkyl is optionally substituted with one or more halogen or ($C_1$-$C_6$)alkoxy.

A compound of formula 7 or 7a, or a salt thereof, can be deoxygenated to provide a corresponding compound of formula 6, by the treatment of the compound of formula 7 or 7a with a suitable radical source and a suitable radical initiator. Suitable radical sources include trialkyltin hydrides (e.g. tri-n-butyltin hydride), trialkylsilanes (e.g. triethyl silane), dialkyl phosphites (e.g. dimethyl phosphite, diethyl phosphite, di-t-butly phosphite, di-isopropyl phosphite and ethylene glycol phosphite), trialkylborons (e.g. tributylboron) with water, and amine salts of hypophosphorus e.g. diisopropylethylammonium salt of hypophosphorus acid). Suitable radical initiators include AIBN, benzoyl peroxide and air. Suitable solvents include organic solvents such as polar and non-polar aprotic solvents (e.g. dioxane, n-butyl acetate, di-n-butyl ether, diethyl carbonate, diethoxy ethane, toluene, methylcyclohexane and heptanes). The reaction can conveniently be carried out at a temperature from about 75° C. to 100° C.

In another embodiment there is a method for the conversion of a compound of formula 6 or a salt thereof to a compound of formula I or a salt thereof comprising:

a) converting the compound of formula 6 or the salt thereof, to the compound of formula III or the salt thereof by the step outlined in Scheme 2 and described herein below; and b) converting the compound of formula III or the salt thereof to the compound of formula I or the salt thereof by any of the steps outlined in Schemes 5-12 and described herein below.

Preparation of a Compound of Formula III:

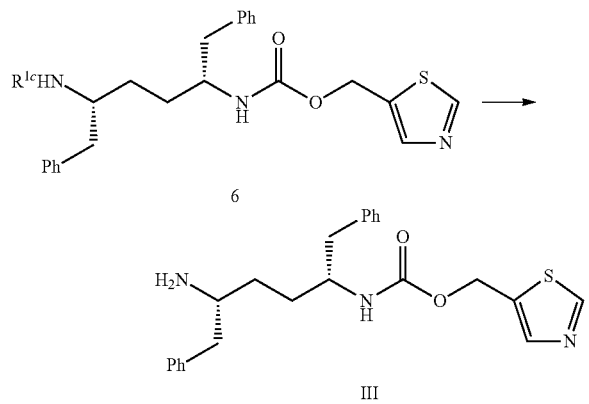

In one embodiment there is a method for deprotecting a compound of formula 6 or a salt thereof to provide a compound of formula 1 or a salt thereof wherein $R^{1c}$ is —C(O)O($C_1$-$C_6$)alkyl wherein —C(O)O($C_1$-$C_6$)alkyl is optionally substituted with halogen or ($C_1$-$C_6$)alkoxy.

A compound of formula 6, or a salt thereof, can be deprotected to provide a compound of formula III, by the treatment of the compound of formula 6 with an appropriate reagent to remove the amine protecting group. For example, a compound of formula 6 wherein $R^{1c}$ is —C(O)OC($CH_3$)$_3$ can be deprotected by treatment of 6 with an acid (e.g. trifluoroacetic acid, hydrochloric acid) either in the presence or absence of a suitable solvent. Suitable solvents include organic solvents such as (e.g. dioxane, methylene chloride). The reaction can conveniently be carried out at a temperature from about 0° C. to 22° C.

In another embodiment, (subsequent to the conversion of 6 to III), there is a method for the conversion of a compound of formula III or a salt thereof to a compound of formula I or a salt thereof comprising converting the compound of formula III or the salt thereof to the compound of formula I or the salt thereof by any of the steps outlined in Schemes 5-12 and described herein below.

A compound of formula IV or IVa can be converted to a compound of formula 6 by the method outlined in Scheme 3. The conversion of the compound of formula IV to the compound of formula 6 includes the conversion of the hydroxy group of the compound of formula IV to a leaving group (e.g. a corresponding compound of formula 9) wherein the leaving group is internally displaced to provide the corresponding aziridine compound of formula 11. The compound of formula 11 can be ring-opened to provide the compound of formula II. As the conversion of compound of IV to II results in the loss of stereochemistry at the hydroxy position, the synthesis of the compound of formula II can also utilize the compound of formula IVa (mixture of epimers at the hydroxy position) as the starting material. In a similar manner the corresponding compound of formula IV wherein the stereochemistry at the hydroxy position is "R" instead of "S" can also serve as a starting material to prepare the compound of formula 12. The compound of formula II can be converted to the compound of formula I by the methods described in International Patent Applications WO 2008/010921, WO 2008/103949 and WO 2010/115000 and discussed herein below.

Scheme 3

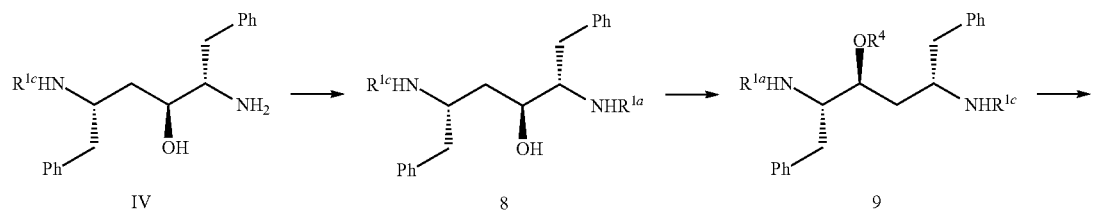

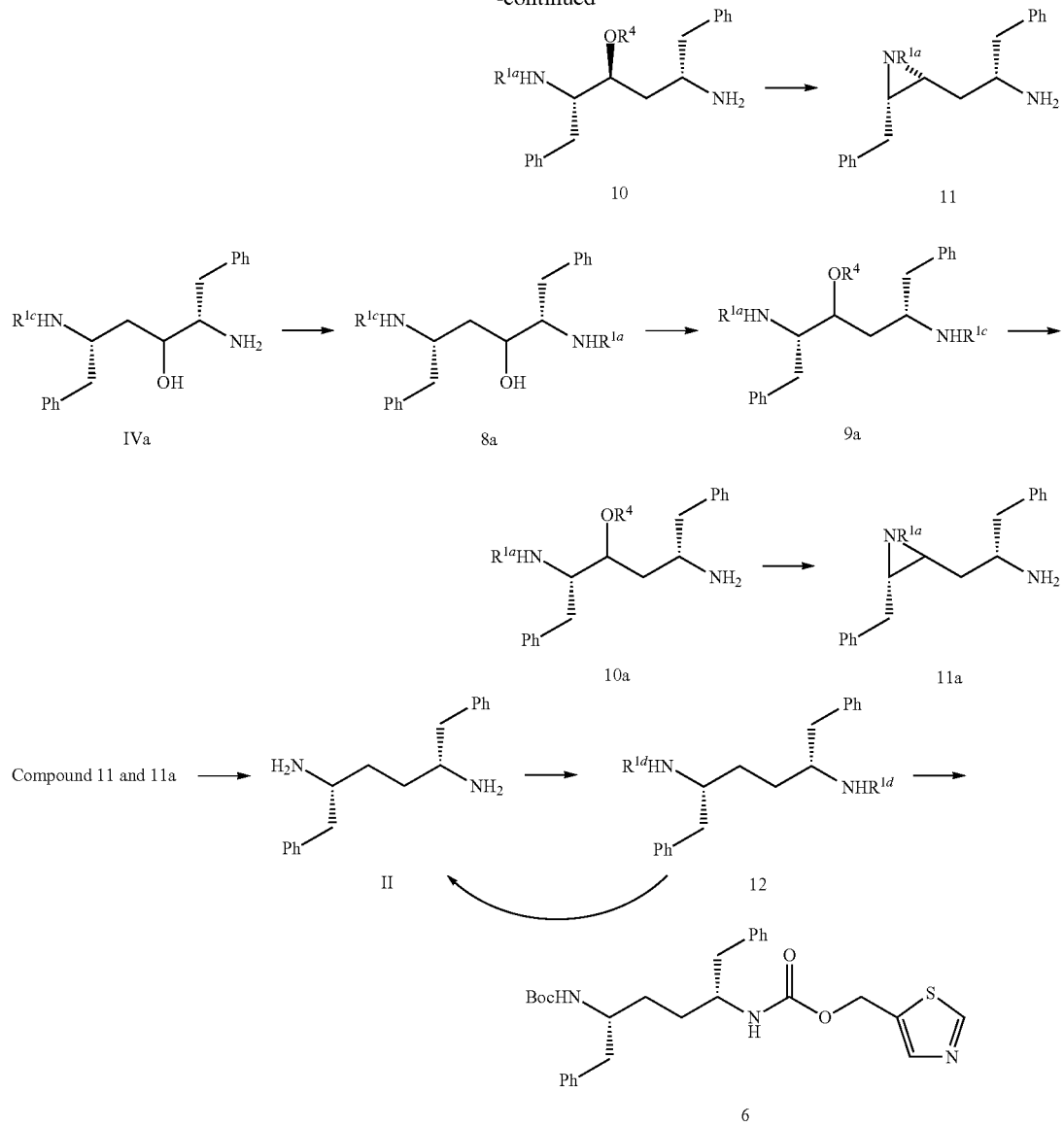
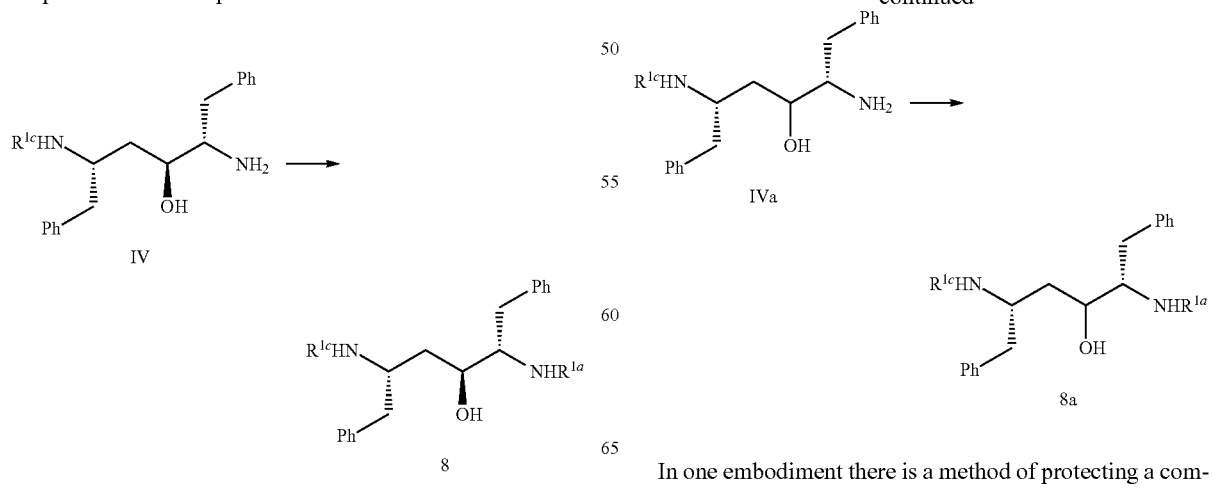
Preparation of a Compound of Formula 8 or 8a:
In one embodiment there is a method of protecting a compound of formula IV (or IVa) or a salt thereof to provide a corresponding compound of formula 8 (or 8a) or a salt thereof, wherein $R^{1a}$ is —C(O)OCH$_2$Ph, wherein —C(O)OCH$_2$Ph is optionally substituted with one or more (C$_1$-C$_6$)alkyl or (C$_1$-C$_6$)alkoxy; and $R^{1c}$ is —C(O)O(C$_1$-C$_6$)alkyl wherein —C(O)O(C$_1$-C$_6$)alkyl is optionally substituted with one or more halogen or (C$_1$-C$_6$)alkoxy.

A specific value for $R^{1c}$ is —C(O)OC(CH$_3$)$_3$. A specific value for $R^{1a}$ is —C(O)O—CH$_2$Ph These specific values are also specific values for the embodiments described herein below for the chemistry of Scheme 3.

The compound of formula IV or IVa, or salts thereof can be protected by any benzyl carbamate protecting group under standard conditions to provide the compound of formula 8 or 8a, or salts thereof. A variety of suitable reagents are available to convert the amine of IV or IVa to the protected amine of compound 8 or 8a. For example, a benzyl carbamate protecting group (e.g. a Cbz group) can be introduced by means of an appropriate haloformate reagent (e.g. benzyl chloroformate). Additional reagents may be required for a particular protection step such as the inclusion of a suitable base. Suitable bases include organic bases (e.g. amine bases including alkylamines such as diisopropylethylamine, triethylamine, N-methyl morpholine), metal hydrides (e.g. potassium hydride), alkoxides (e.g. sodium tert-butoxide), and carbonate bases (e.g. potassium carbonate or cesium carbonate). Suitable solvents include aprotic organic solvents (e.g. pyridine) or mixtures thereof. The reaction can conveniently be carried out at a temperature from about 0° C. to 25° C.

In another embodiment there is a method for the conversion of a compound of formula 8 or a salt thereof or a compound of formula 8a or a salt thereof to a compound of formula 1 or a salt thereof comprising:

a) converting the compound of formula 8 or the compound of formula 8a or the salts thereof, to the compound of formula II or the salt thereof by the steps outlined in Scheme 3 and described herein below; and b) converting the compound of formula II or the salt thereof to the compound of formula I or the salt thereof by any of the steps outlined in Schemes 4-12 and described herein below.

Preparation of a Compound of Formula 9 or 9a:

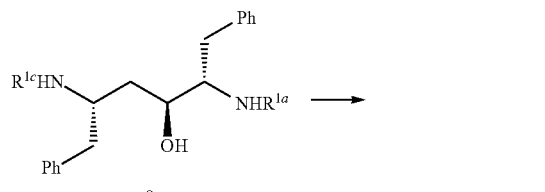

8

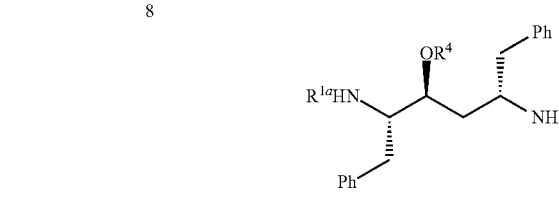

8a

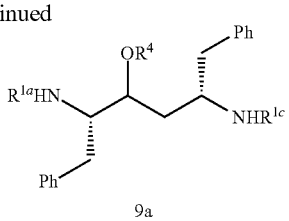

9a

In one embodiment there is a method of activating a compound of formula 8 (or 8a) or a salt thereof to provide a corresponding compound of formula 9 (or 9a) wherein $R^{1a}$ is —C(O)OCH$_2$Ph, wherein —C(O)OCH$_2$Ph is optionally substituted with one or more (C$_1$-C$_6$)alkyl or (C$_1$-C$_6$)alkoxy; $R^{1c}$ is —C(O)O(C$_1$-C$_6$)alkyl wherein —C(O)O(C$_1$-C$_6$)alkyl is optionally substituted with one or more halogen or (C$_1$-C$_6$)alkoxy; and $R^4$ is —SO$_2$(C$_1$-C$_6$)alkyl or —SO$_2$aryl, wherein —SO$_2$(C$_1$-C$_6$)alkyl is optionally substituted with one or more halogen, and wherein —SO$_2$aryl is optionally substituted with one or more halogen, (C$_1$-C$_6$)alkyl or NO$_2$.

A specific value for $R^4$ is p-toluenesulfonyl. This specific value is also a specific value for the embodiments described herein below for the chemistry of Scheme 3.

The compound of formula 8 or 8a, or salts thereof, can be converted to the corresponding compound of formula 9 or 9a by a variety of suitable reagents available to convert a hydroxy group to a leaving group. For example, a sulfonate leaving group (e.g. tosylate, mesylate, trifluoromethansulfonate) can be prepared utilizing a variety of sulfonating reagents such as a sulfonyl halide (e.g. a sulfonyl chloride such as p-toluenesulfonyl chloride) or a sulfonic anhydride and a base including amine bases (e.g. alkylamines such as diisopropylethylamine, triethylamine, N-methyl morpholine), metal hydrides (e.g. potassium hydride), tetramethylpiperidides, alkoxides (e.g. sodium tert-butoxide), hexamethyldisilazides and carbonate bases (e.g. potassium carbonate or cesium carbonate). Suitable solvents include organic solvents such as aprotic organic solvents (e.g. pyridine, tetrahydrorfuran and 2-methyltetrahydrorfuran) or mixtures thereof. The reaction can conveniently be carried out at a temperature from about 0° C. to 25° C.

In another embodiment there is a method for the conversion of a compound of formula 9 or a salt thereof or a compound of formula 9a or a salt thereof to a compound of formula I or a salt thereof comprising:

a) converting the compound of formula 9 or the compound of formula 9a or the salts thereof, to the compound of formula II or the salt thereof by the steps outlined in Scheme 3 and described herein below; and b) converting the compound of formula II or the salt thereof to the compound of formula I or the salt thereof by any of the steps outlined in Schemes 4-12 and described herein below.

Preparation of a Compound of Formula 10 or 10a:

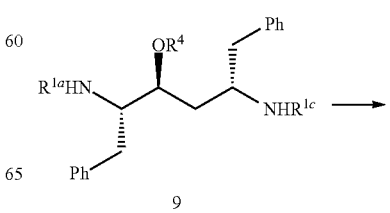

9

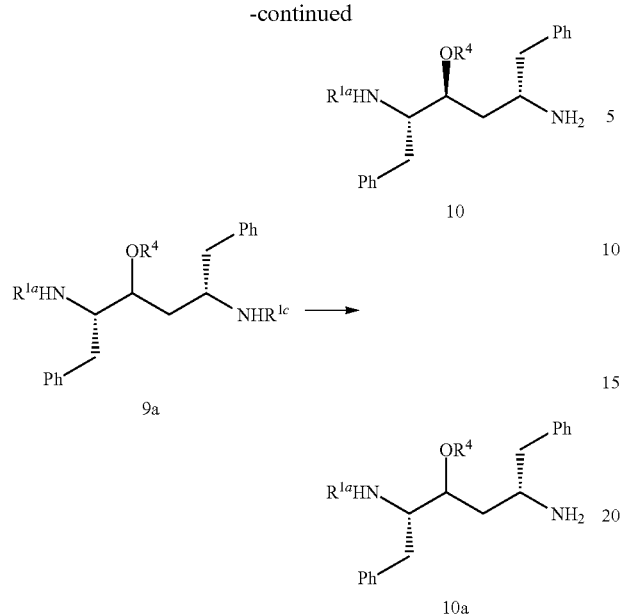

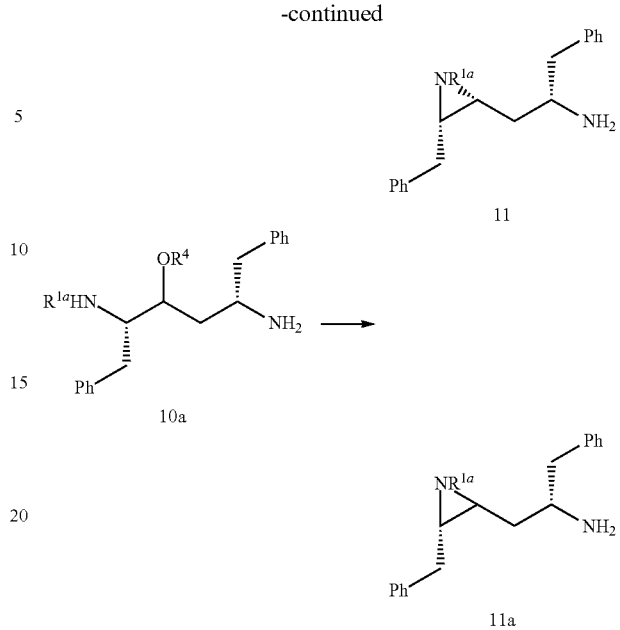

In one embodiment there is a method of deprotecting a compound of formula 9 (or 9a) or a salt thereof to provide a corresponding compound of formula 10 (or 10a) or a salt thereof, wherein $R^{1a}$ is —C(O)OCH$_2$Ph, wherein —C(O)OCH$_2$Ph is optionally substituted with one or more (C$_1$-C$_6$)alkyl or (C$_1$-C$_6$)alkoxy; $R^{1c}$ is —C(O)O(C$_1$-C$_6$)alkyl wherein —C(O)O(C$_1$-C$_6$)alkyl is optionally substituted with one or more halogen or (C$_1$-C$_6$)alkoxy; and $R^4$ is —SO$_2$(C$_1$-C$_6$)alkyl or —SO$_2$aryl, wherein —SO$_2$(C$_1$-C$_6$)alkyl is optionally substituted with one or more halogen, and wherein —SO$_2$aryl is optionally substituted with one or more halogen, (C$_1$-C$_6$)alkyl or NO$_2$.

The compound of formula 9 or 9a, or salts thereof, can be deprotected under standard conditions to provide the corresponding compound of formula 10 or 10a or salts thereof. For example, the deprotection can be carried out with an acid such as an organic acid (e.g. trifluoroacetic acid) or a mineral acid (e.g. hydrochloric acid). Suitable solvents include organic solvents such methylene chloride and trifluoroacetic acid or mixtures thereof. The reaction can be conveniently carried out at a temperature from about 0° C. to 25° C.

In another embodiment there is a method for the conversion of a compound of formula 10 or a salt thereof or a compound of formula 10a or a salt thereof to a compound of formula 1 or a salt thereof comprising:

a) converting the compound of formula 10 or the compound of formula 10a or the salts thereof, to the compound of formula II or the salt thereof by the steps outlined in Scheme 3 and described herein below; and b) converting the compound of formula II or the salt thereof to the compound of formula I or the salt thereof by any of the steps outlined in Schemes 4-12 and described herein below.

Preparation of a Compound of Formula 11 or 11a:

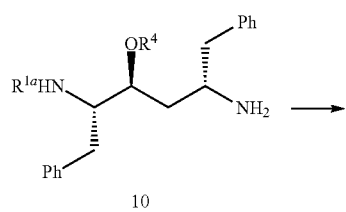

In one embodiment there is a method of cyclizing a compound of formula 10 (or 10a) or a salt thereof to provide a corresponding compound of formula 11 (or 11a) or a salt thereof, wherein $R^{1a}$ is —C(O)OCH$_2$Ph, wherein —C(O)OCH$_2$Ph is optionally substituted with one or more (C$_1$-C$_6$)alkyl or (C$_1$-C$_6$)alkoxy; and $R^4$ is —SO$_2$(C$_1$-C$_6$)alkyl or —SO$_2$aryl, wherein —SO$_2$(C$_1$-C$_6$)alkyl is optionally substituted with one or more halogen, and wherein —SO$_2$aryl is optionally substituted with one or more halogen, (C$_1$-C$_6$)alkyl or NO$_2$.

The compound of formula 10 or 10a, or salts thereof, can be cyclized to provide the corresponding aziridine of formula 11 or 11a, or salts thereof. The cyclization can be carried out by treatment of the compound of formula 10 or 10a with a base such as a metal hydride (e.g. sodium hydride, potassium hydride, calcium hydride), metal alkoxide (e.g. potassium tert-butoxide, sodium, tert-butoxide, lithium tert-butoxide), alkylamide (e.g. lithium diisopropylamide), hexamethyldisilazides (e.g. lithium hexamethyldisilazide) or carbonate base (e.g. potassium carbonate or cesium carbonate). Suitable solvents include organic solvents such as aprotic organic solvents (e.g. tetrahydrofuan, 2-methyltetrahydrorfuran). The reaction can be conveniently carried out at a temperature from about −20° C. to 40° C.

In another embodiment there is a method for the conversion of a compound of formula 11 or a salt thereof or a compound of formula 11a or a salt thereof to a compound of formula I or a salt thereof comprising:

a) converting the compound of formula 11 or the compound of formula 11a or the salts thereof, to the compound of formula II or the salt thereof by the steps outlined in Scheme 3 and described herein below; and b) converting the compound of formula II or the salt thereof to the compound of formula I or the salt thereof by any of the steps outlined in Schemes 4-12 and described herein below.

Preparation of a Compound of Formula II or IIa:

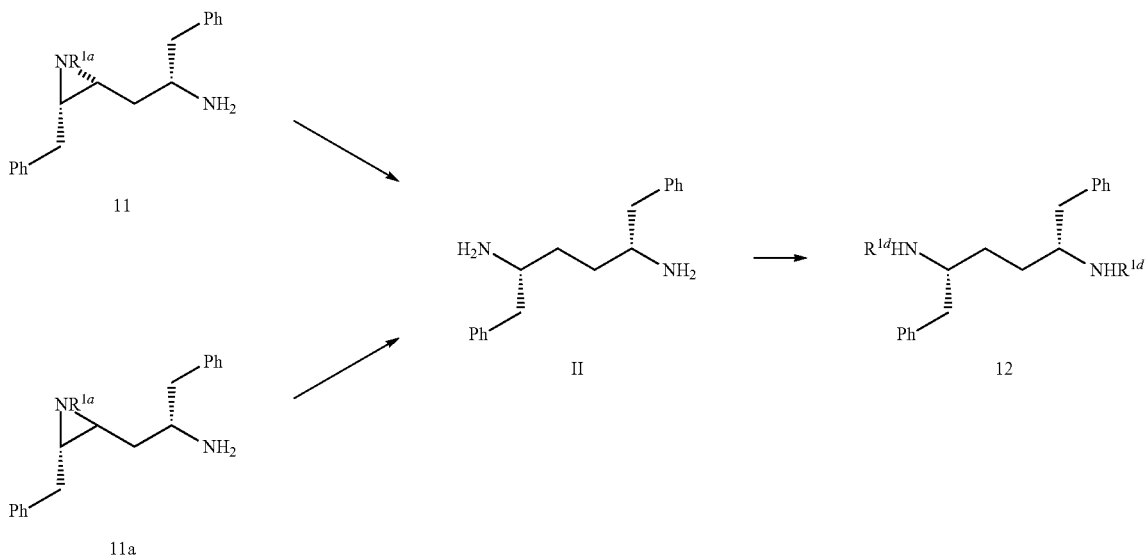

In one embodiment there is a method of ring-opening a compound of formula 11 (or 11a) or a salt thereof to provide a corresponding compound of formula II or a salt thereof, wherein $R^{1a}$ is —C(O)OCH$_2$Ph, wherein —C(O)OCH$_2$Ph is optionally substituted with one or more (C$_1$-C$_6$)alkyl or (C$_1$-C$_6$)alkoxy.

The compound of formula 11 or 11a, or salts thereof, can be ring-opened to provide the compound of formula II, or a salt thereof. The ring-opening of the compound of formula 11 or 11a can be carried out under hydrogenation conditions such as those utilizing a hydrogenation catalyst and hydrogen gas. Suitable hydrogenation catalysts include palladium on carbon (e.g. 10% palladium on carbon), Raney nickel, and Wilkinson's catalyst. Suitable solvents include protic organic solvents such as methanol, ethanol or isopropanol. The reaction can be conveniently carried out at a temperature from about 25° C. to 40° C.

The compound of formula II can be optionally converted to an amine-protected version of compound II such as a compound of formula 12 or a salt thereof, wherein each $R^{1d}$ is independently an amine protecting group. Suitable amine protecting groups include, for example (C$_1$-C$_6$)alkyl alkyl carbamates and arylmethyl carbamates (e.g. t-butyl carbamate, benzyl carbamate) wherein the carbamates can be optionally substituted with one or more or more (C$_1$-C$_6$)alkyl or (C$_1$-C$_6$)alkoxy groups. Such protection of the diamine may enhance isolation or purification. The protection step can be carried out with a suitable reagent to introduce a protecting group such as a carbamate anhydride (e.g. di-t-butyl dicarbonate) and a suitable base such as amine bases (e.g. alkylamines such as diisopropylethylamine, triethylamine, N-methyl morpholine) or an inorganic base such as a carbonate bases (e.g. potassium carbonate or cesium carbonate). Suitable solvents include aprotic organic solvents such as tetrahydrofuran or methylene chloride. The reaction can be conveniently carried out at a temperature from about 0° C. to 25° C. Such a step can facilitate purification and or isolation. The compound of formula 12 or a salt thereof can be conveniently converted back to the compound of formula II or a salt thereof or the compound of formula 6 or a salt thereof by procedures described herein.

In another embodiment, (subsequent to the conversion of 11 or 11a to II), there is a method for the conversion of a compound of formula II or a salt thereof to a compound of formula I or a salt thereof comprising converting the compound of formula II or the salt thereof to the compound of formula I or the salt thereof by any of the steps outlined in Schemes 4-12 and described herein below.

Alternative Preparation of the Compound of Formula 4:

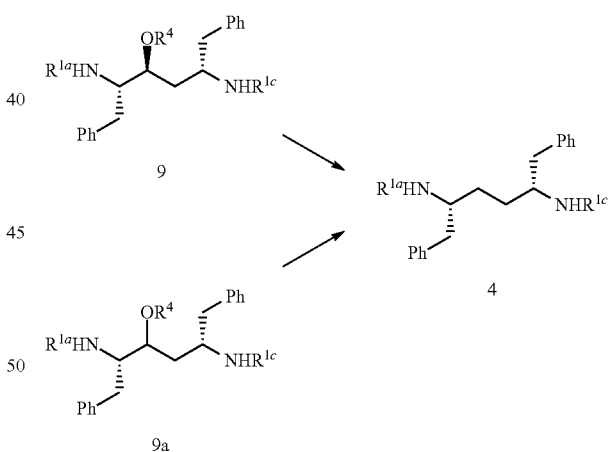

In one embodiment there is a method of reducing a compound of formula 9 (or 9a) or a salt thereof to provide a corresponding compound of formula 4 or a salt thereof wherein $R^{1a}$ is —C(O)OCH$_2$Ph, wherein —C(O)OCH$_2$Ph is optionally substituted with one or more (C$_1$-C$_6$)alkyl or (C$_1$-C$_6$)alkoxy; $R^{1c}$ is —C(O)O(C$_1$-C$_6$)alkyl wherein —C(O)O (C$_1$-C$_6$)alkyl is optionally substituted with one or more halogen or (C$_1$-C$_6$)alkoxy; and $R^4$ is —SO$_2$(C$_1$-C$_6$)alkyl or —SO$_2$aryl, wherein —SO$_2$(C$_1$-C$_6$)alkyl is optionally substituted with one or more halogen, and wherein —SO$_2$aryl is optionally substituted with one or more halogen, (C$_1$-C$_6$) alkyl or NO$_2$.

The compound of formula 9 or 9a, or salts thereof, can be reduced to provide the corresponding compound of formula 4, or a salt thereof. The reduction can be carried out by treating 9 or 9a with reducing agent such as a hydride reducing agent. Suitable hydride reducing agents include sodium hydride, potassium hydride, and sodium borohydride. Suitable solvents include ethereal solvents such as tetrahydrofuran, 2-methyltetrahydrofuran, 1,4-dioxane, and ethyl ether. The reaction can be conveniently carried out at a temperature from about 0° C. to 60° C.

In another embodiment there is a method for the conversion of a compound of formula 4 or a salt thereof to a compound of formula I or a salt thereof comprising:

a) converting the compound of formula 4 or a salt thereof, to the compound of formula II or the compound of formula III or salts thereof by the steps outlined in Scheme 1 and described herein above; and b) converting the compound of formula II or the compound of formula III or salts thereof to the compound of formula I or the salt thereof by any of the steps outlined in Schemes 4-12 and described herein below.

Preparation of the Compound of Formula I:

The compounds of formula II and III can be converted to the compound of formula I following procedures described in International Patent Application WO2010/115000 (pages 26-32). Schemes 4, 5, 6 and 7 outline these procedures.

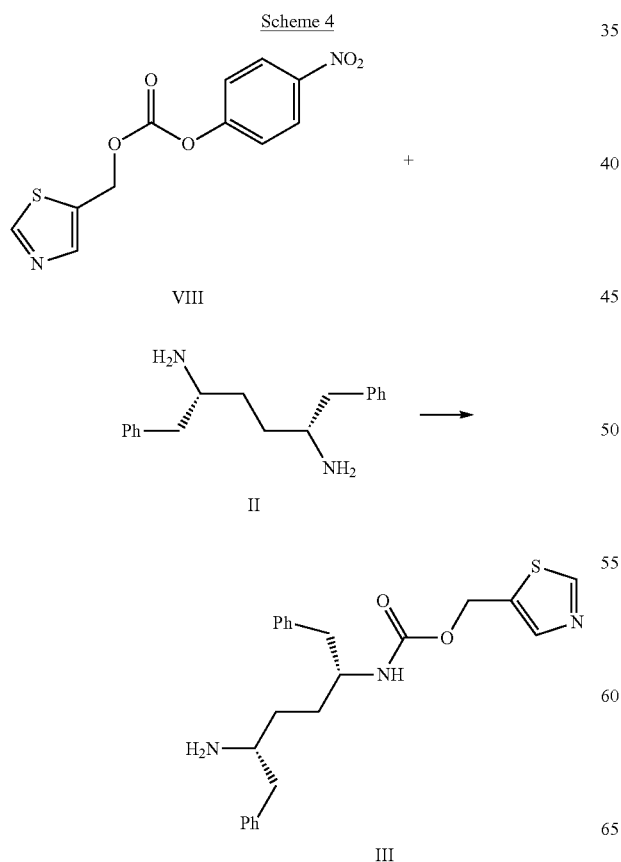

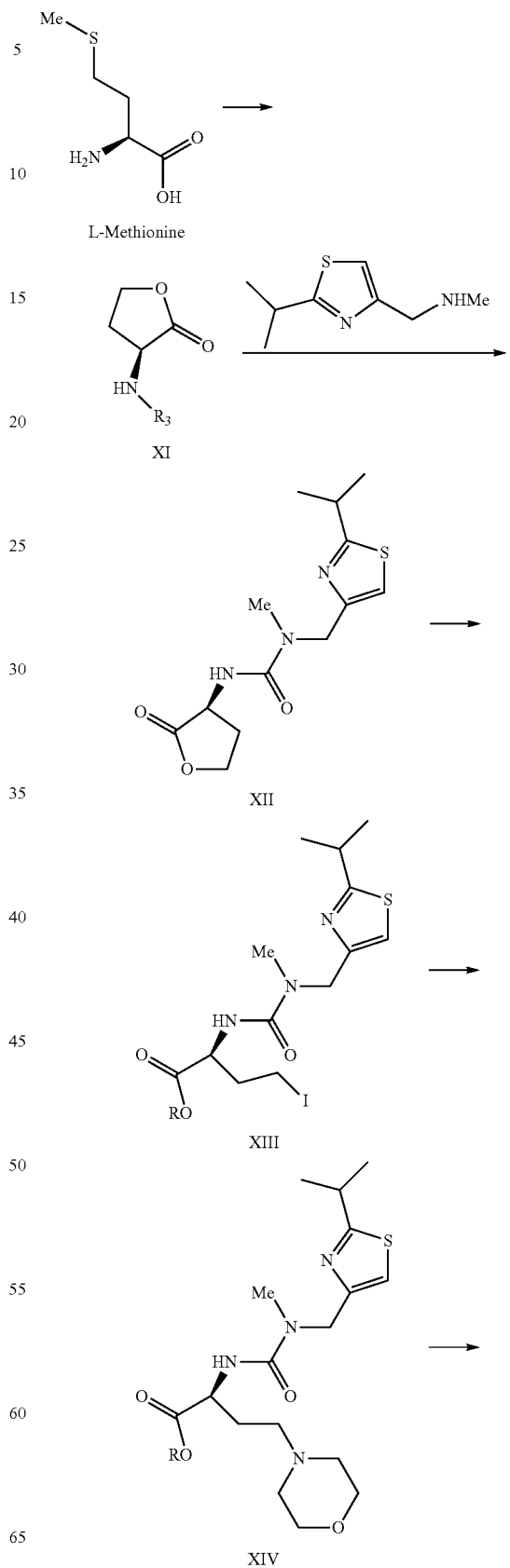

51

-continued

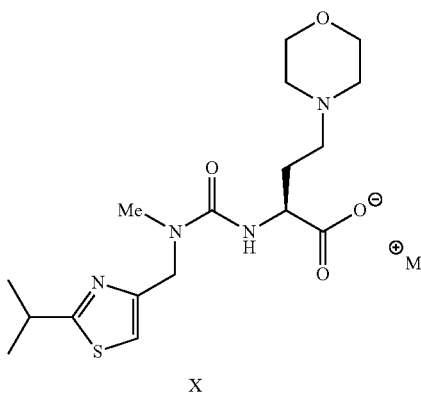

Scheme 6

III + X →

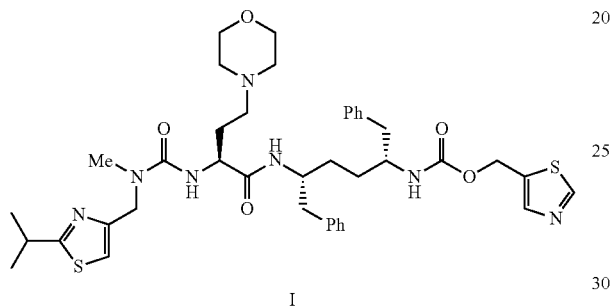

I

Preparation of a Compound of Formula VIII:

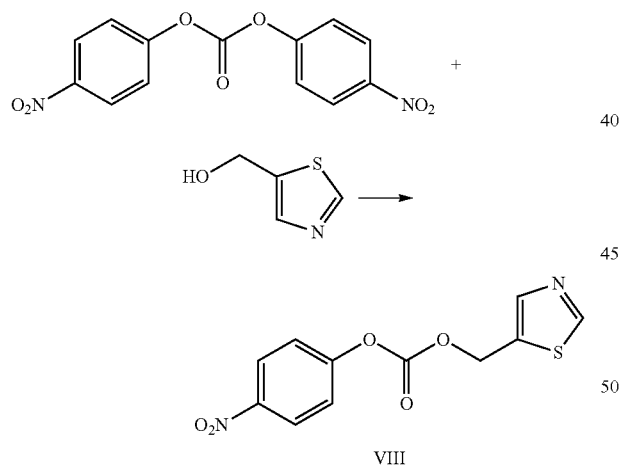

VIII

The mixed carbonate of formula VIII can be prepared by treating 5-hydroxymethylthiazole with a suitable carbonate or carbonate equivalent having a leaving group adjacent to the carbonyl carbon, such as phosgene in the presence of a base. For example, suitable carbonates include bis-(4-nitrophenyl) carbonate and disuccinimidyl carbonate. The reaction can conveniently be carried out in a suitable aprotic organic solvent, such as dichloromethane, tetrahydrofuran, 1,2-dichloroethane, or diethylether, or a mixture thereof. Suitable bases include trialkylamine bases, such as diisopropylethylamine, N-methyl morpholine, and triethylamine.

52

Preparation of a Compound of Formula III or a Salt Thereof

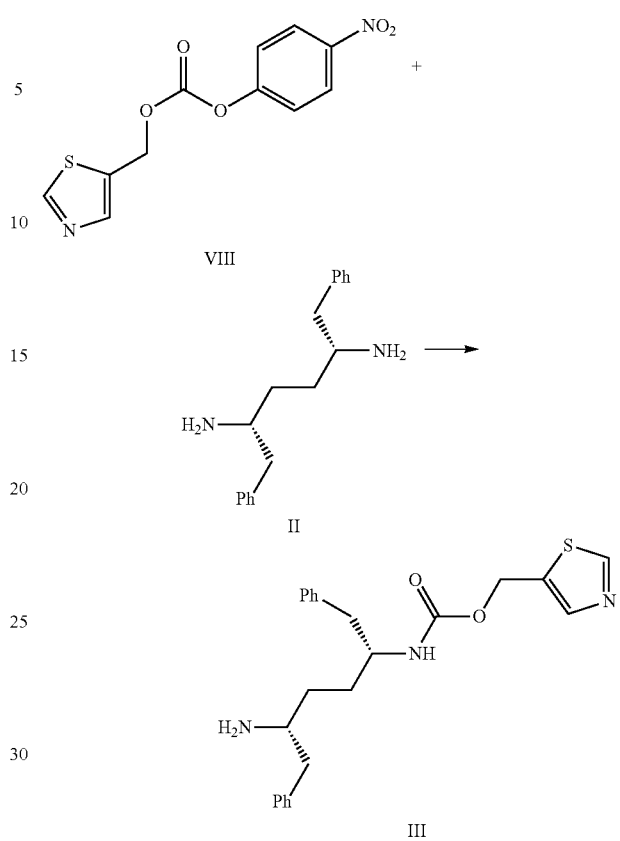

A compound of formula III or a salt thereof can be prepared from a compound of formula II or a salt thereof by treatment with a carbonate of formula VIII or a salt thereof in the presence of a suitable base in a suitable solvent. Suitable bases include carbonate bases (e.g. potassium carbonate) and trialkylamines (e.g. diisopropylethylamine, or N-methyl morpholine). Suitable solvents include solvents such as dichloromethane, tetrahydrofuran, 1,2-dichloroethane, isopropylacetate, and diethylether, and mixtures thereof.

Preparation of a Compound of Formula XI:

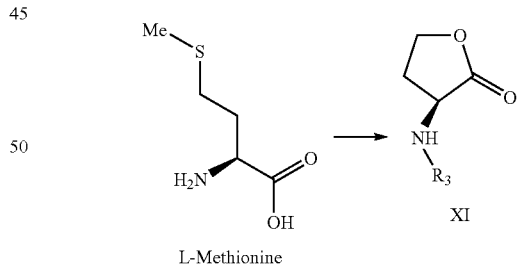

L-Methionine

A compound of formula XI wherein $R_3$ is H or a salt thereof can be prepared by treating L-methionine with an alkylating agent in the presence of water and acetic acid. Suitable alkylating agents include alkyl bromides (bromoacetic acid), alkyl iodides, alkyl chlorides, and dimethyl sulfate. The reaction can conveniently be carried out in a solvent that comprises an alcohol (e.g. isopropanol), water, and acetic acid. The reaction can be carried out at a temperature from about 22° C. to about 90° C. A compound of formula XI wherein $R_3$ is a protecting group (e.g. a carbamate, amide, or benzyl protecting group) or a salt thereof can be prepared by protecting a corresponding compound of formula XI wherein $R_3$ is hydrogen to provide the compound of formula XI wherein $R_3$ is a protecting group or the salt thereof.

Preparation of a Compound of Formula XII:

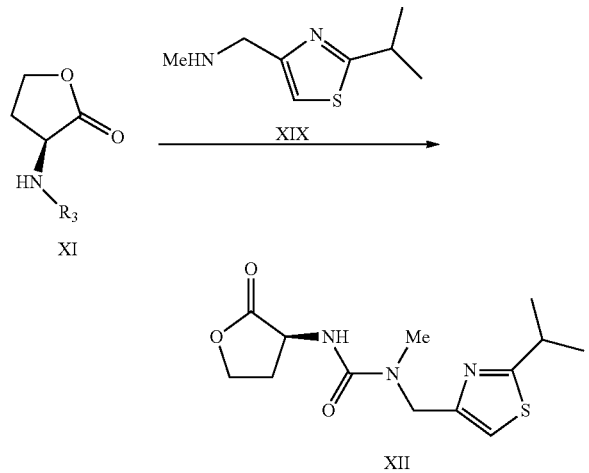

A compound of formula XII can be prepared by treating a compound of formula XI wherein $R_3$ is H or a protecting group (e.g. a carbamate, amide, or benzyl protecting group), or a salt thereof with a compound of formula XIX or a salt thereof, in an aprotic solvent at a temperature from about 0° C. to about 30° C. in the presence of a suitable base and a carbonyl source, such as CDI. When $R_3$ is a protecting group it can subsequently be removed to provide the compound of formula XII or the salt thereof. Suitable bases include metal hydrides (e.g. sodium hydride), and trialkylamines (e.g. diisopropylethylamine, triethylamine, N-methyl morpholine or DBU). Suitable aprotic solvents include tetrahydrofuran, 2-methyltetrahydrofuran, and dichloromethane, and mixtures thereof.

Preparation of a Compound of Formula XIII:

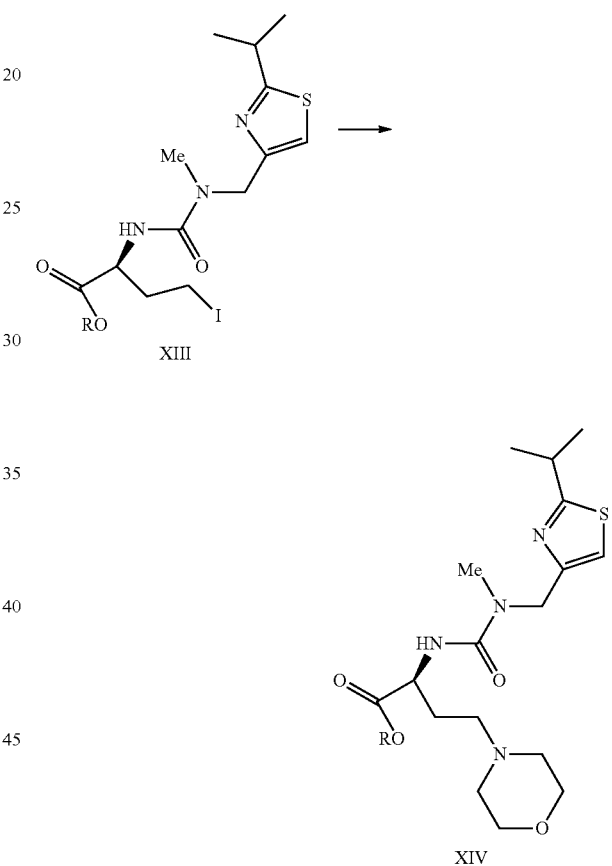

A compound of formula XIII can be prepared by treating a compound of formula XII or a salt thereof with a suitable iodide source (e.g. trimethylsilyl iodide, hydrogen iodide, or sodium iodide and trimethylsilyl chloride) in an aprotic solvent in the presence of an alcohol ROH to provide the compound of formula XIII wherein R is $(C_1-C_8)$alkyl. Suitable aprotic solvents include tetrahydrofuran, 2-methyltetrahydrofuran, dichloromethane, and acetonitrile, and mixtures thereof. The reaction can typically be carried out at a temperature from about 0° C. to about 22° C.

Preparation of a Compound of Formula XIV or a Salt Thereof:

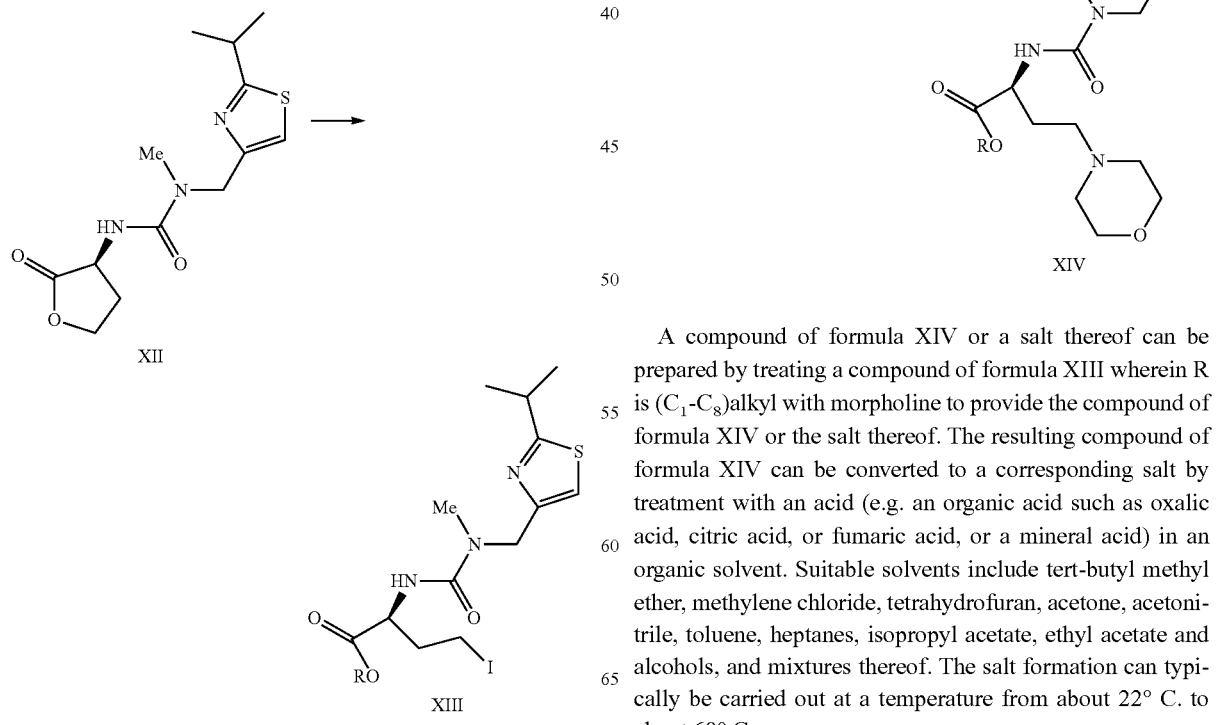

A compound of formula XIV or a salt thereof can be prepared by treating a compound of formula XIII wherein R is $(C_1-C_8)$alkyl with morpholine to provide the compound of formula XIV or the salt thereof. The resulting compound of formula XIV can be converted to a corresponding salt by treatment with an acid (e.g. an organic acid such as oxalic acid, citric acid, or fumaric acid, or a mineral acid) in an organic solvent. Suitable solvents include tert-butyl methyl ether, methylene chloride, tetrahydrofuran, acetone, acetonitrile, toluene, heptanes, isopropyl acetate, ethyl acetate and alcohols, and mixtures thereof. The salt formation can typically be carried out at a temperature from about 22° C. to about 60° C.

Preparation of a Compound of Formula X:

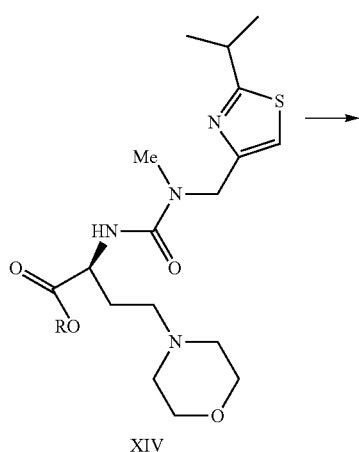

XIV

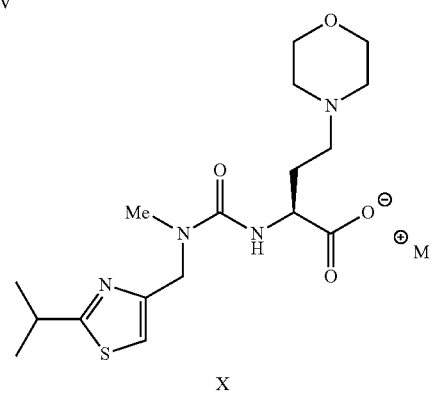

X

A compound of formula X wherein M⁺ is a counterion, or a salt thereof, can be prepared by hydrolyzing an ester of formula XIV wherein R is $(C_1-C_8)$alkyl or a salt thereof under standard conditions. For example, the hydrolysis can be carried out in an aqueous solvent (e.g. water and dichloromethane) in the presence of a base (e.g. potassium hydroxide or lithium hydroxide) at a temperature from about −10° C. to about 28° C.

Preparation of a Compound of Formula I:

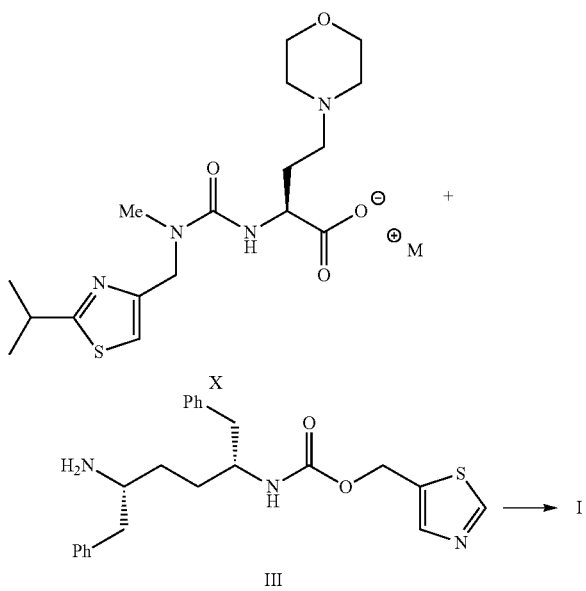

A compound of formula I or a salt thereof can be prepared by coupling an acid salt of formula X wherein M⁺ is a counterion with an amine of formula III to form the corresponding amide. This amide forming reaction can be carried out under standard conditions. For example, it can be carried out in a suitable organic solvent (e.g. dichloromethane) in the presence of a suitable coupling agent (e.g. EDC•HCl and HOBt). Other suitable amide coupling reagents and conditions are known in the field. The reaction can typically be carried out at a temperature from about −30° C. to about 20° C.

The resulting compound of formula I can be isolated using standard techniques. The compound of formula I as described here or throughout the application can be isolated employing a solid support material as described in International Patent Application Publication Number WO 2009/135179

Alternative Preparation of the Compound of Formula I:

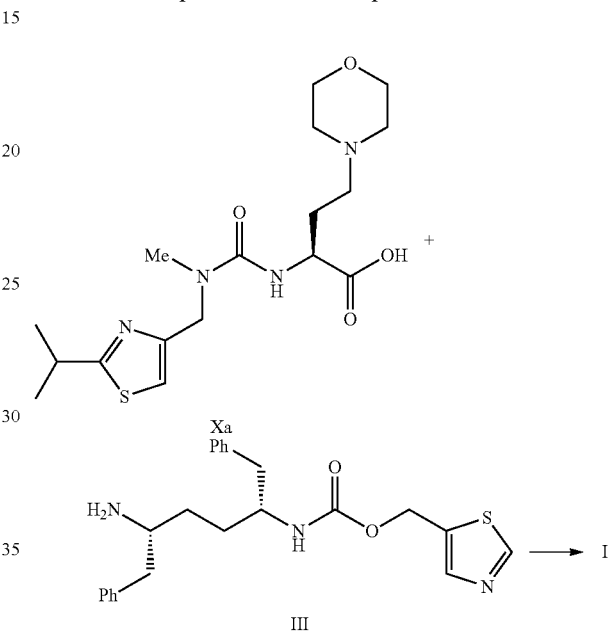

A compound of formula I or a salt thereof can be prepared by coupling an acid of formula Xa or a salt thereof with an amine of formula III or a salt thereof to form the corresponding amide. This amide forming reaction can be carried out under standard conditions. For example, it can be carried out in a suitable organic solvent (e.g. dichloromethane) in the presence of a suitable coupling agent (e.g. EDC®HCl and HOBt). Other suitable amide coupling reagents and conditions are known in the field. The reaction can typically be carried out at a temperature from about −30° C. to about 20° C.

Alternative Preparation of a Compound of Formula XII:

The compound of formula XII shown in Scheme 5 above can also be prepared as illustrated in Scheme 7.

Scheme 7

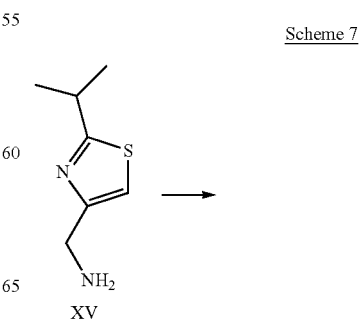

XV

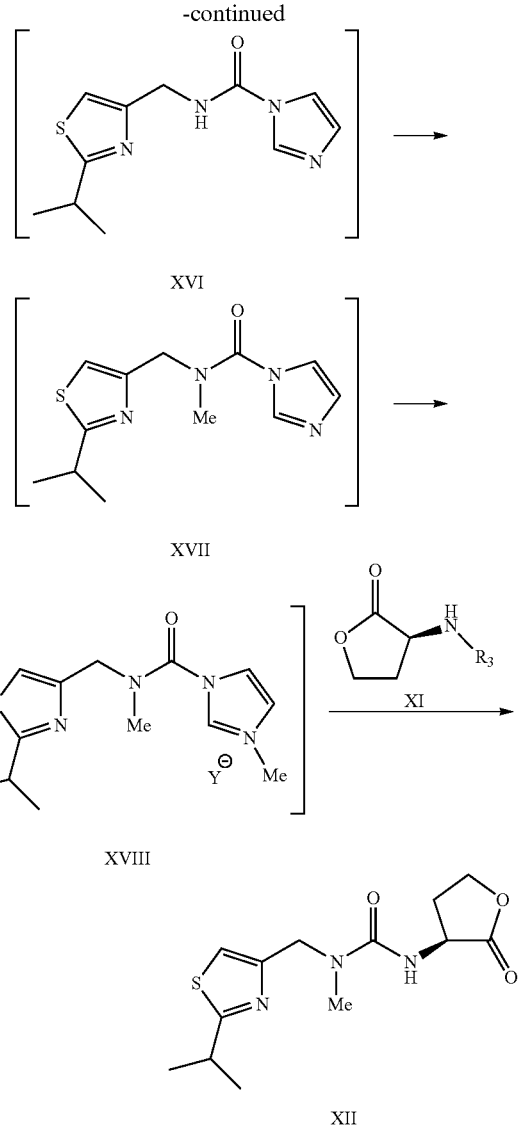

Preparation of a Compound of Formula XII

The amine of formula XV or a salt thereof can be treated with carbonyldiimidazole, in the presence of a suitable base (e.g. a trialkylamine, such as triethylamine, N-methyl morpholine, diisopropylethylamine, or DBU; a hydride base, such as sodium hydride; or an amide base, such as LiHMDS) in an aprotic solvent (e.g. tetrahydrofuran, or 2-methyltetrahydrofuran) to provide the urea of formula XVI. Alkylation of the urea of formula XVI with a suitable methylating agent (e.g. methyl iodide) in the presence of a base in an aprotic solvent provides a compound of formula XVII. Further alkylation with a suitable methylating agent (e.g. methyl iodide) provides a salt of formula XVIII. Treatment of the salt of formula XVIII with an N-unprotected amino γ-lactone of formula XI or with a corresponding N-protected amino γ-lactone (e.g. a carbamate, amide or benzylamine) in a suitable aprotic solvent (e.g. tetrahydrofuran, or 2-methyltetrahydrofuran) in the presence of a suitable base (e.g. a trialkylamine, such as triethylamine, N-methyl morpholine, diisopropylethylamine, or DBU) provides the compound of formula XII. If an N-protected amino γ-lactone is utilized in the previously described step (i.e. Compound XI where $R_3$ is a protecting group), the resulting protected product can be deprotected to provide the compound of formula XII.

Alternative Methods for the Preparation of the Compound of Formula I:

The compounds of formula II and III can also be converted to the compound of formula I following procedures described in International Patent Application Publication Number WO 2008/010921 (pages 212-221) and International Patent Application Publication Number WO 2008/103949 (pages 248-259). Methods I-IV (including Schemes 8-12) and the subsequent experimental write-ups depicted below describe these procedures.

Method I:

Scheme 8

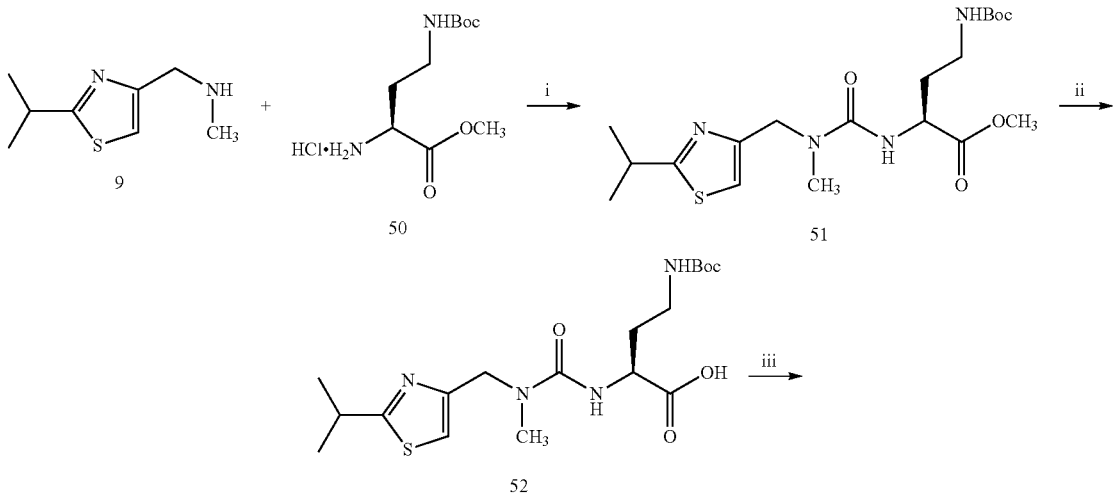

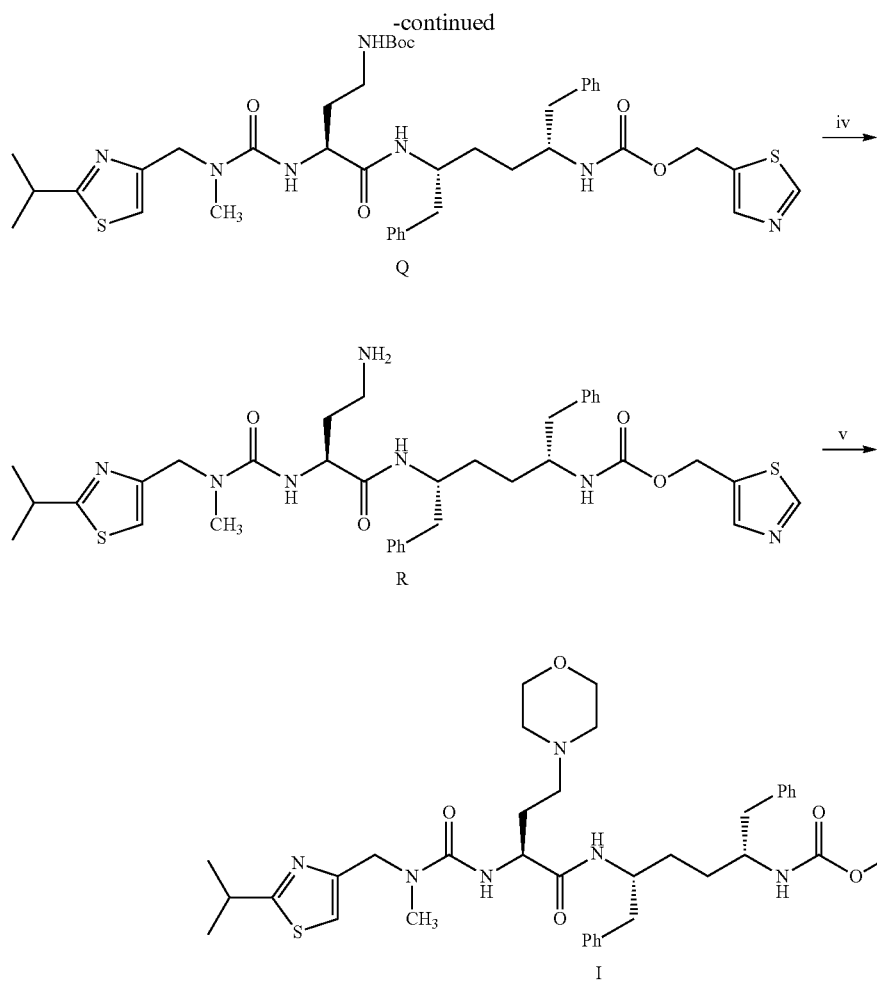

i) CDI, DIPEA, CH₂Cl₂; ii) LiOH, THF/H₂O; iii) Cmpd of formula III, DIPEA, EDC, HOBt, THF;
iv) a. HCl/dioxane; b. Na₂CO₃; v) (BrCH₂CH₂)₂O, NaHCO₃, DMF Compound 50

Compound 50 is commercially available from Chem Impex International, and was used without further purification.

Compound 51

Compound 50 (7.0 g, 26.0 mmol) was dissolved in CH₂Cl₂ (330 mL) and 1,1-carbonyldiimidazole (4.22 g, 26.0 mmol) was added, followed by i-Pr₂NEt (19 mL, 104 mmol). The solution was stirred at 25° C. for 12 hours. Compound 9 (4.44 g, 26.0 mmol) was dissolved in 20 mL of CH₂Cl₂ and added to the reaction mixture. The solution was stirred at 25° C. for 7 hours. The solvent was removed in vacuo and the residue was diluted with ethyl acetate and washed with water and brine. The organic layers were dried (Na₂SO₄), filtered, and evaporated. Purification by Combiflash® (stationary phase: silica gel; eluent: 66-100% EtOAc/Hexane gradient) gave Compound 51 (7.34 g). m/z: 429.0 (M+H)⁺.

Compound 52

Compound 51 (7.34 g, 17.13 mmol) was dissolved in THF (90 mL) and 1M aqueous LiOH (35 mL) was added. The mixture was stirred at 25° C. for 0.5 hour. The reaction was quenched with 1M HCl (51 mL) and the mixture was adjusted to pH 2. The mixture was extracted with ethyl acetate. The organic layers were dried over Na₂SO₄, filtered, and evaporated to provide Compound 52 (7.00 g). The recovered Compound 52 was used in the next step without further purification. m/z: 415.0 (M+H)⁺.

Compound Q

Compound 52 (2.57 g, 6.21 mmol) was dissolved in THF (67 mL). compound of formula III (2.10 g, 5.13 mmol) was added, followed by HOBt (1.04 g, 7.70 mmol), i-Pr₂NEt (3.67 mL, 20.52 mmol), and EDC (1.82 mL, 10.26 mmol). The mixture was stirred at 25° C. for 12 hours. The solvent was removed under reduced pressure. The residue was diluted with ethyl acetate and washed sequentially with saturated aqueous Na₂CO₃, water, and brine. The organic phase was dried over Na₂SO₄, filtered, and evaporated. Purification by flash column chromatography (stationary phase: silica gel; eluent: 5% iPrOH/CH₂Cl₂) gave Compound Q (3.02 g). m/z: 806.2 (M+H)⁺.

Compound R

Compound Q (3.02 g, 3.74 mmol) was suspended in 4.0 N HCl/dioxane solution (30 mL) and stirred at 25° C. for 3 hours. Solvent was removed under reduced pressure and Et₂O was poured into the reaction mixture. The resulting suspension was stirred vigorously for 1.5 hours. The solid was allowed to settle and the ether layer was decanted. Washing of the precipitate with Et₂O was repeated two more times. The product was dried in vacuo to afford a white solid (3.18 g, quantitative yield). Saturated aqueous Na₂CO₃ solution was added to above solid (3.18 g) with stirring until solid disappeared. The aqueous solution was extracted with ethyl acetate. The organic phases were dried over Na₂SO₄, filtered, and evaporated to afford Example R as a yellow foam (2.44 g, 81%). The recovered Compound R was used without further purification in the next step. m/z: 706.1 (M+H)⁺.

Compound of Formula I

Compound R (1.00 g, 1.42 mmol) was dissolved in DMF (20 mL) and bromoethyl ether (196 μL, 1.56 mmol) was added dropwise, followed by NaHCO₃ (0.239 g, 2.84 mmol). The reaction mixture was stirred at 25° C. for 2 hours. The solution was heated to 65° C. and stirred for 12 hours. The solvent was removed under reduced pressure. The residue was diluted with EtOAc and washed sequentially with water and brine. The organic phase was dried over Na₂SO₄ filtered, and evaporated. Purification by reverse-phase HPLC (Phenomenex Synergi® Comb-HTS column, eluent: 5-95% CH₃CN/water) gave the compound of formula I (580 mg, 53%). ¹H NMR (CDCl₃) δ 8.98 (s, 1H); 7.90 (s, 1H); 7.75 (m, 1H); 7.40-7.00 (m, 11H), 6.55 (br s, 1H); 5.58 (m, 1H); 5.28, 5.19 (d$_{AB}$, J=14 Hz, 2H); 4.70-4.37 (m, 3H); 3.99 (m, 5H); 3.76 (br s, 1H); 3.65-3.30 (m, 3H); 2.97 (m, 5H); 2.90-2.60 (m, 6H); 2.28 (br s, 1H); 1.91 (br s, 1H); 1.60-1.30 (m, 10H). m/z: 776.2 (M+H)⁺

Method II:

Scheme 9

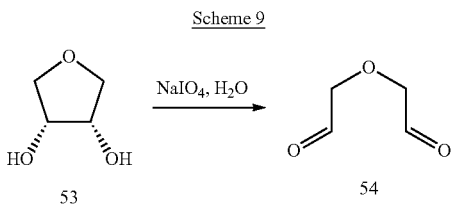 [SMILES: O[C@@H]1COC[C@@H]1O ; O=CCOCC=O]

Compound 54

Compound 54 was prepared following the procedure described in *J. Med. Chem.* 1993, 36, 1384 (herein incorporated by reference in its entirety for all purposes).

To solution of Compound 53 (0.550 g, 5.28 mmol) (Sigma-Aldrich) in H₂O (8.8 mL) at 0° C. was added NaIO₄ (1.016 g, 4.75 mmol). The mixture was allowed to slowly warm to 25° C. and stirred for 12 hours. Solid NaHCO₃ was added to the reaction mixture until pH 7. CHCl₃ (16 mL) was added and the mixture was allowed to stir for 5 minutes. The mixture was filtered and the solid was washed with CHCl₃ (6 mL). The combined H₂O/CHCl₃ solution was used directly in the next step without further purification.

Scheme 10

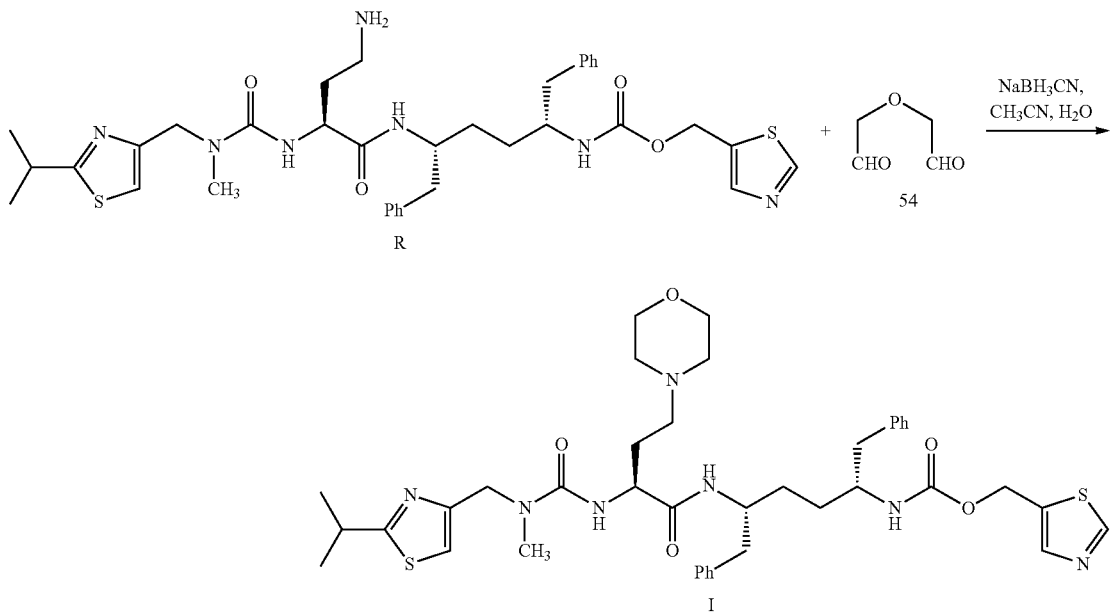

Compound of Formula I

To a solution of Compound R (70 mg, 0.1 mmol) in CH₃CN (5 mL) was added sodium cyanoborohydride (50 mg) in water (5 mL). To the above mixture was added a solution of dialdehyde compound 54 (0.6 mmol) in CHCl₃/H₂O) (4 mL/1 mL). The mixture was stirred for 12 hours, and basified with saturated Na₂CO₃ solution. The mixture was extracted with EtOAc, and organic phase was washed with water and brine, and dried over Na₂SO₄. Purification by reverse-phase HPLC (Phenomenex Synergi® Comb-HTS column) gave the compound of formula I (57 mg).

Method III

Scheme 11

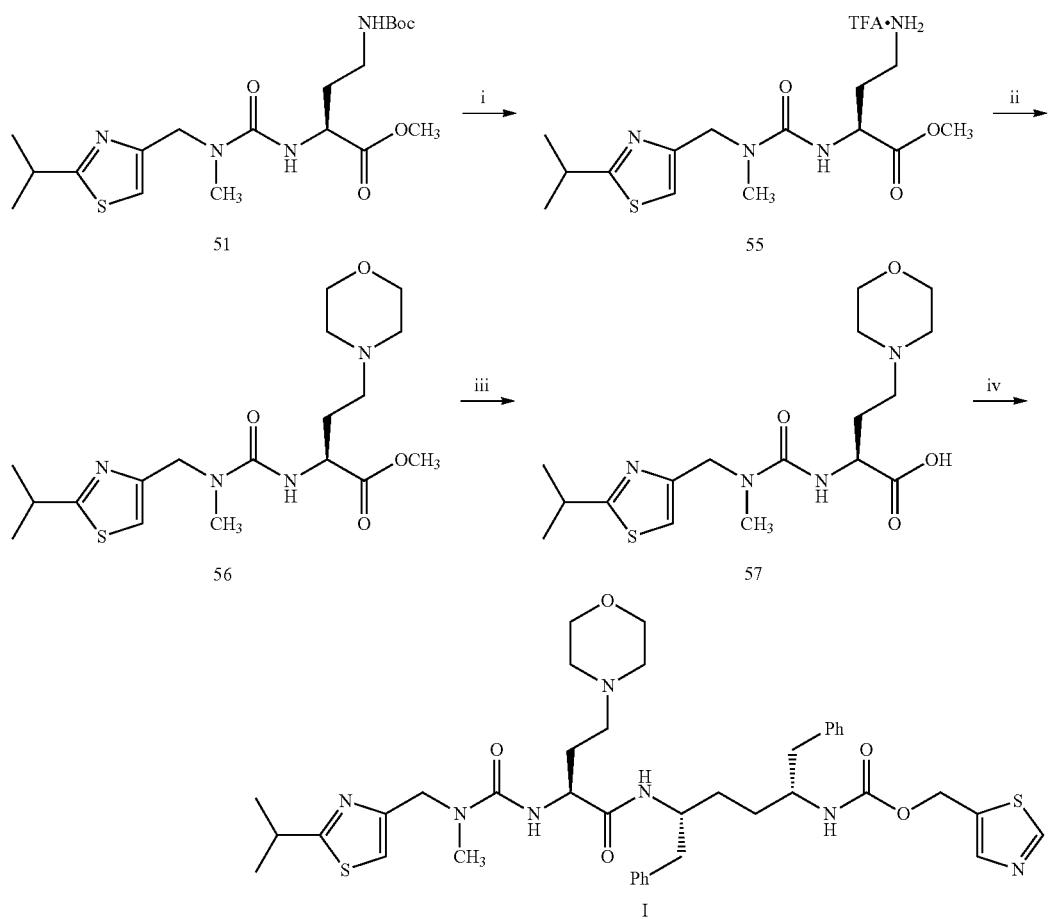

i) TFA, CH₂Cl₂; ii) Cmpd 54, NaBH₃CN, H₂O/CH₃CN; iii) LiOH, THF/H₂O;
iv) cmpd of formula III, DIPEA, EDC, HOBt, THF Compound 55

Compound 51 (0.28 g, 0.66 mmol) was dissolved in $CH_2Cl_2$ (4 mL) and TFA (mL) was added dropwise. The reaction was allowed to stir at 25° C. for 1 hour. The solvent was removed under reduced pressure to afford compound 55 (0.39 g). m/z: 329.0 $(M+H)^+$.

Compound 56

To a solution of compound 55 (0.39 g, 0.89 mmol) in $CH_3CN$ (45 mL) was added $NaBH_3CN$ (0.45 g, 7.12 mmol) and $H_2O$ (45 mL). A solution of compound 54 (0.55 g, 5.34 mmol) in $CHCl_3/H_2O$ (40 mL) was added. The mixture was stirred at 25° C. for 12 hours. The reaction mixture was made basic with saturated aqueous $Na_2CO_3$ and extracted sequentially with ethyl acetate and dichloromethane. The combined organic layers were washed sequentially with $H_2O$ and brine, dried over $Na_2SO_4$, filtered, and evaporated. Purification by Combiflash® (stationary phase: silica gel; eluent: 0-10% MeOH/$CH_2Cl_2$ gradient) gave compound 56 (0.17 g). m/z: 399.1 $(M+H)^+$.

Compound 57

Compound 56 (377 mg, 0.95 mmol) was dissolved in THF (4 mL) and 1M aqueous LiOH (1.90 mL) was added. The mixture was stirred at 25° C. for 1 hour. The reaction was neutralized with 1M HCl. THF was removed under reduced pressure and the aqueous solution was lyophilized to afford compound 57 (365 mg). The material was used directly in the next step without further purification. m/z: 385.1 $(M+H)^+$.

Compound of Formula I

The compound of formula I (185 mg, 57%) was prepared following the same procedure as for compound Q (method 1), except that compound 57 (160 mg, 0.42 mmol) was used instead of compound 52. mass m/z: 776.2 $(M+H)^+$.

Method IV

Scheme 12

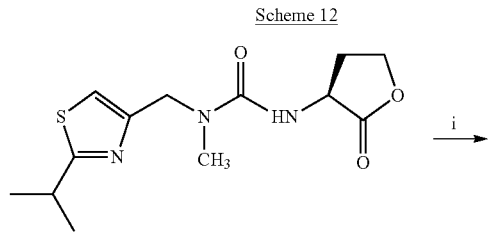

122

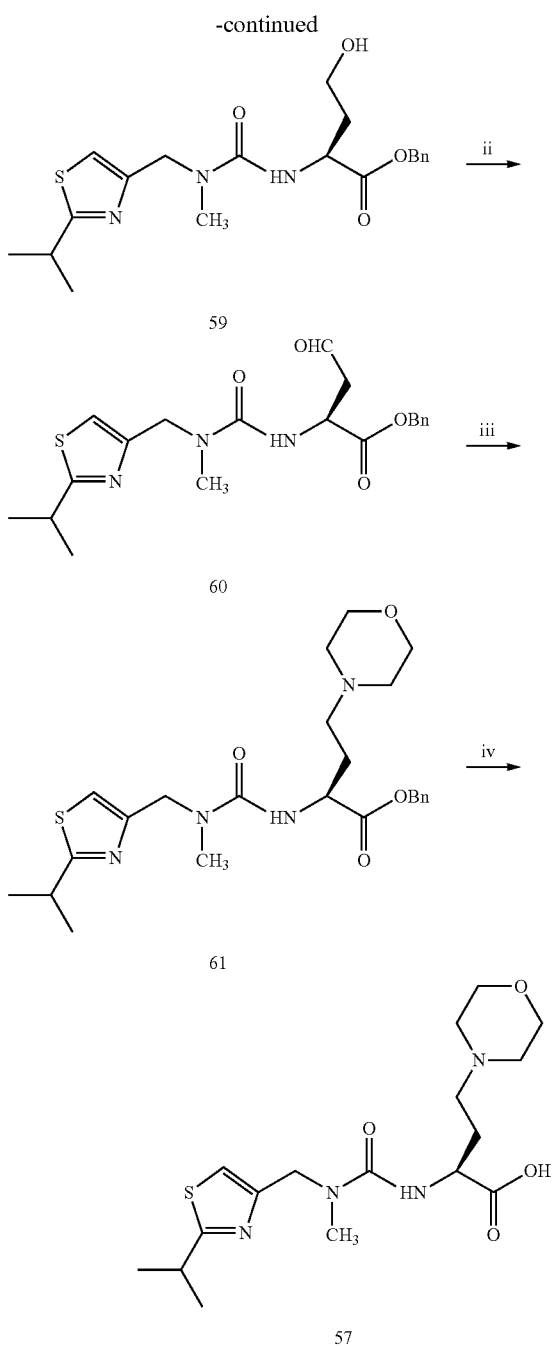

i) a. NaOH/H₂O; b. BrBr; ii) SO₃/pyridine; iii) morpholine/NaBH(OAc)₃; iv) a. NaOH; b. HCl Compound 59

To a solution of compound 122 (33 g, 112 mmol) (prepared by the method of WO2008/010921) in ethanol (366 mL) at 0° C. was added a solution of sodium hydroxide (4.7 g, 117 mmol) in water (62 mL). The mixture was stirred for one hour at 25° C., and solvents were removed under reduced pressure. The mixture was co-evaporated with ethanol (3×400 mL), and dried at 60° C. for two hours under high vacuum to give a white solid. To the solution of above solid in DMF (180 mL) was added benzyl bromide (16.2 mL, 136 mmol). The mixture was stirred for 16 hours under darkness, and was quenched with water (300 mL). The mixture was extracted with EtOAc (4×300 mL). The combined organic phase was washed with water (5×) and brine, and dried over Na₂SO₄. Concentration gave compound 59 (48 g), which was used in the next step without further purification.

Compound 60

A mixture of compound 59 (33 g, 74 mmol) in DMSO (225 mL) and Et₃N (36 mL) was stirred for 30 minutes. The mixture was cooled to 0-10° C., SO₃-pyridine (45 g) was added, and the stirring was continued for 60 minutes. Ice (300 g) was added, and the mixture was stirred for 30 minutes. EtOAc (300 mL) was added and sat. Na₂CO₃ was added until pH was 9~10. The organic phase was separated from the aqueous phase, and the aqueous phase was extracted with EtOAc (2×300 ml). The combined organic phases were washed with sat Na₂CO₃ (2×), water (3×), and brine. The mixture was dried over Na₂SO₄ and concentrated to give compound 60 (32 g), which was used directly in next step without further purification.

Compound 61

To a solution of compound 60 (32 g) in CH₃CN (325 mL) was added morpholine (12.9 mL, 148 mmol), with a water bath around the reaction vessel, followed by HOAc (8.9 mL, 148 mmol), and NaBH(OAc)₃ (47 g, 222 mmol). The mixture was stirred for 12 hours. CH₃CN was removed under reduced pressure, and the mixture was diluted with EtOAc (300 mL). Sat. Na₂CO₃ was added until the pH was 9~10. The organic phase was separated from the aqueous phase, and the aqueous phase was extracted with EtOAc (2×300 mL). The combined organic phases were washed with sat Na₂CO₃ (2×), water (1×), and brine (1×). The mixture was dried over Na₂SO₄. The resulting residue was concentrated and purified by silica gel column chromatography (EtOAc to DCM/iPrOH=10/1) to give compound 61 (30 g).

Compound 57

To a solution of compound 61 (26.5 g, 56 mmol) in ethanol (160 mL) at 0° C. was added a solution of sodium hydroxide (2.5 g, 62 mmol) in water (30 mL). The mixture was stirred for one hour at 25° C., and solvents were removed under reduced pressure. The mixture was diluted with water (200 mL), and was washed with CH₂Cl₂ (6×100 mL). The water phase was acidified with 12 N HCl (5.2 mL), and was dried under reduced pressure to give compound 57 (22 g).

Compound of Formula I

Compound 57 was converted to the compound of formula I using the procedure described in Method II, above.

The following illustrate non-limiting examples.

Example 1

Preparation of compound 1b (1,6-diphenyl-5S-tert-butoxycarbonylamino-3S-hydroxy-2S-phenyl-methoxy-carbonylaminohexane)

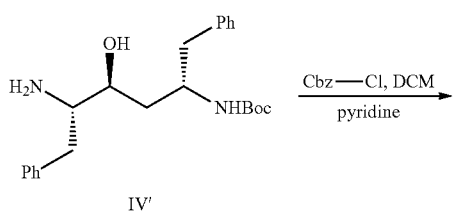

-continued

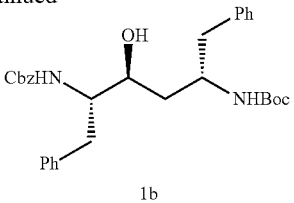

1b

Benzyl chloroformate (5.1 mL, 36 mmol) was added by addition funnel over approximately 10 minutes to a mechanically stirred mixture of aminoalcohol IV' (11.54 g, 30 mmol) and pyridine (2.94 mL, 36 mmol) in dichloromethane (200 mL) at 0° C. The cooling bath was removed and the reaction was allowed to warm to room temperature and stirred overnight. At the end of this period, HPLC analysis showed the presence of <3 A % of the starting alcohol IV'. The reaction mixture was filtered and the white residue (amino alcohol IV') was washed with dichloromethane (100 mL). The filtrate was transferred to a separatory funnel. The organic layer was washed twice with cold (0° C.) 5% sodium bisulfate solution (2×75 mL), twice with saturated sodium bicarbonate solution (2×100 mL), brine (100 mL) and dried over anhydrous sodium sulfate. Removal of the solvent in vacuo afforded a white solid which was triturated with hexane and filtered. The carbamate 1b was obtained as white solid weighing 13.22 g (85%). Thin layer chromatography (Tlc) assay showed $R_f$=0.19 on SiO$_2$ using 25% ethyl acetate/hexane as the eluent or an $R_f$=0.75 on SiO$_2$ using 50% ethyl acetate/hexane as the eluent. $^1$H NMR (300 MHz, CDCl$_3$): δ 7.4-7.05 (m, 15H), 5.09 (m, 1H), 5.05 (s, 2H), 4.5 (br s, 1H), 3.88-3.74 (m, 2H), 3.63 (br s, 1H), 2.87-2.85 (d, 2H, J=7.8 Hz), 2.72-2.70 (d, 2H, J=6.3 Hz), 1.63-1.60 (m, 2H), 1.38 (s, 9H).

Example 2

Preparation of compound 2b (3S-dithiocarbonic acid 1,6-diphenyl-5S-tert-butoxycarbonylamino-2S-phenylmethoxyarbonylaminohexane, methyl ester)

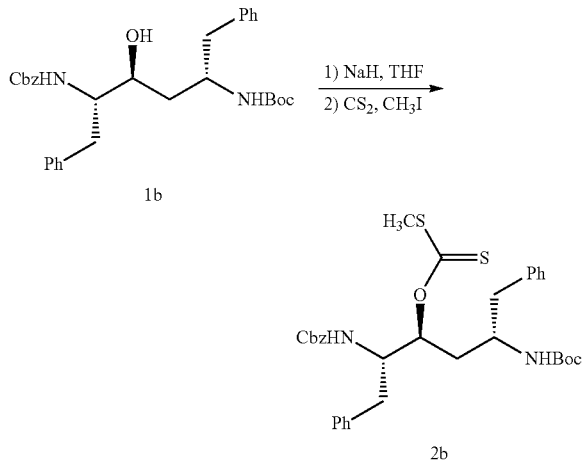

Sodium hydride (160 mg, 4 mmol, 60% oil dispersion) was added to a magnetically stirred solution of the carbamate 1b (2.07 g, 4 mmol) in THF (30 mL) at room temperature. A vigorous gas evolution occurred. The reaction was stirred at room temperature for 30 minutes and then carbon disulfide (724 µL, 12 mmol) was added in one portion. The reaction was stirred for 1 hour to afford a yellow solution. Methyl iodide (274 µL, 4.4 mmol) was then added and the reaction and allowed to stir overnight. At the end of this period, the reaction was judged complete and the mixture was transferred to a round-bottom flask and the solvent was removed in vacuo. The residue was transferred to a separatory funnel with ethyl acetate (300 mL) and pH 6 phosphate buffer (100 mL). After mixing, the layers were separated. The aqueous layer was re-extracted with ethyl acetate (100 mL). The combined organic extracts were washed with brine and dried over anhydrous sodium sulfate. Removal of the solvent in vacuo afforded a thick residue. The residue was adsorbed onto 20 mL of silica gel with MTBE. The residue was chromatographed on 80 mL of flash silica gel using a hexane to 30% ethyl acetate/hexane gradient to afford 1.79 g (74%) of the desired xanthate 2b. Tlc assay showed $R_f$=0.64 on SiO$_2$ using 25% ethyl acetate/hexane as the eluent. $^1$H NMR (300 MHz, CDCl$_3$): δ 7.4-7.0 (m, 151-1), 5.83-5.79 (t, 1H, J=63 Hz), 5.05-4.9 (q, 2H, J=12 Hz), 4.85-4.82 (m, 1H), 4.55-4.2 (m, 2H), 4.08-4.01 (br s, 1H), 2.84-2.6 (m, 4H), 2.56 (s, 3H), 1.8 (br s, 2H), 1.38 (s, 9H).

Example 3

Preparation of compound 3b (3S-imidazolecarbothioic acid 1,6-diphenyl-5S-tert-butoxycarbonylamino-2S-phenyl methoxycarbonylaminohexane, ester)

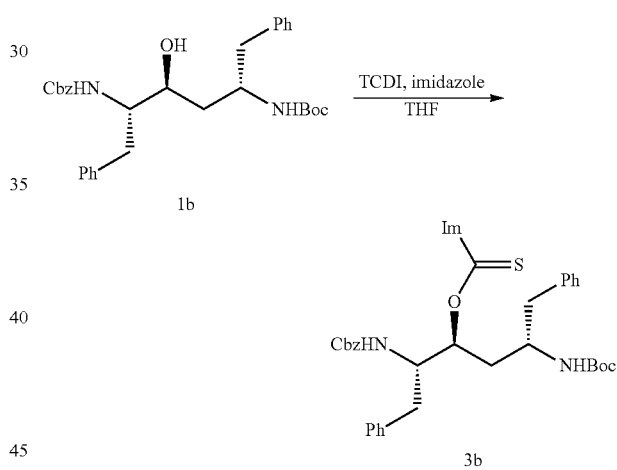

Thiocarbonyldiimidazole (TCDI) (2.14 g, 12 mmol) was added to a magnetically stirred solution of alcohol 1b (3.11 g, 6 mmol) and imidazole (408 mg, 6 mmol) in THF (30 mL) at room temperature. The reaction mixture was stirred for 48 hours and judged complete by HPLC analysis. The reaction mixture was transferred to a round-bottom flask and the solvent was removed in vacuo. The residue was dissolved in ethyl acetate (200 mL) and transferred to a separatory funnel. The organic layer was washed twice with cold (0° C.) 5% sodium bisulfate solution (2×100 mL), saturated sodium bicarbonate solution (100 mL), brine (100 mL) and dried over anhydrous sodium sulfate. Filtration and removal of the solvent in vacuo afforded 4.1 g crude semisolid. The crude solid was adsorbed onto 24 mL of flash silica gel and chromatographed on 82 mL of flash silica gel using a 20% ethyl acetate/hexane to 60% ethyl acetate/hexane gradient. The imidazolide 3b product (Im is imidazol-1-yl) was obtained in 3.5 g (93%) as a white solid foam. Tlc assay showed $R_f$=0.28 on SiO$_2$ using 25% ethyl acetate/hexane as the eluent or $R_f$=0.80 on SiO$_2$ using 50% ethyl acetate/hexane as the eluent.

Example 4

Preparation of compound 4b (1,6-diphenyl-5R-tert-butoxycarbonylamino-2R-phenylmethoxycarbonylamino-hexane)

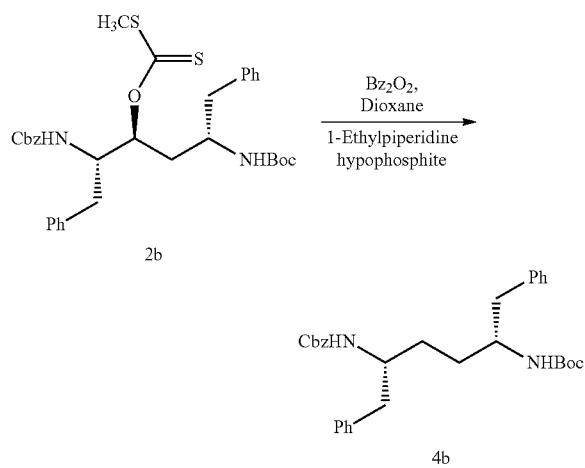

A solution of xanthate 2b (243 mg, 0.4 mmol) and benzoyl peroxide (97 mg, 0.4 mmol) in dioxane (4 mL) was added over two hours via a syringe pump to a magnetically stirred, deoxygenated mixture of dioxane (8 mL) and 1-ethylpiperidine hypophosphite (3.6 g, 20 mmol) at 105° C. After the addition was complete, the reaction mixture was heated at 105° C. for two additional hours. The reaction was cooled and judged to be complete by HPLC analysis. The reaction mixture was poured over saturated sodium bicarbonate solution (50 mL) and extracted twice with ethyl acetate (50 mL). The combined organic extracts were washed with brine and dried over anhydrous sodium sulfate. Removal of the solvent in vacuo afforded a thick oil. The oil was chromatographed on silica gel (20 mL) with a gradient of 100% hexane to 40% ethyl acetate/hexane to afford 200 mg (100%) of a white solid (94 A % pure). The white solid was recrystallized from hexane/MTBE (1:5, 15 mL). The product 4b was obtained in 160 mg (80% yield) in >99 A % purity. Tlc assay showed $R_f$=0.61 on $SiO_2$ using 25% ethyl acetate/hexane as the eluent. $^1H$ NMR (300 MHz, $CDCl_3$): δ 7.4-7.1 (m, 15H), 5.049 (s, 21), 4.48 (d, 1H, J=8.7 Hz), 4.21 (br d, 1H), 3.92-3.7 (br m, 2H), 2.8-2.6 (m, 4H), 1.6-1.4 (br s, 2H), 1.38 (s, 9H).

Example 5

Preparation of compound 4b (1,6-diphenyl-5R-tert-butoxycarbonylamino-2R-phenylmethoxycarbonylamino-hexane)

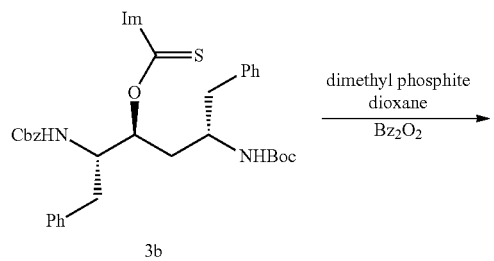

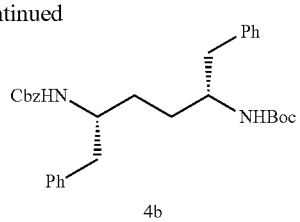

A magnetically stirred solution of the thionoimidazolide 3b (2.02 g, 3.2 mmol) and dimethyl phosphite (14.7 mL, 160 mmol) in dioxane (32 mL) was heated to 105° C. A solution of benzoyl peroxide (465 mg, 1.92 mmol) in dioxane (2.3 mL) was added to the heated solution over 6 hours via syringe pump. After the addition was complete, the reaction was heated at 105° C. for an additional two hours and then allowed to cool overnight. At the end of this period, the reaction was analyzed by HPLC and found to be complete. The reaction mixture was poured over cold (0° C.) saturated sodium bicarbonate solution. Some precipitate formed. The quenched reaction mixture was transferred to a separatory funnel and extracted twice with ethyl acetate (2×250 mL). The combined organic extracts were washed twice with water (2×200 mL), brine (200 mL) and dried over anhydrous sodium sulfate. The solvent was removed in vacuo to afforded 2.2 g crude semi-solid. The crude material was adsorbed onto flash silica gel (14 mL) and chromatographed on flash silica gel using a 100% hexane to 30% ethyl acetate/hexane gradient. Compound 4b was obtained as a white solid weighing 1.28 g (80%) at approximately 80% purity by HPLC. Recrystallization of the solid with MTBE/hexane (5:1, 65 mL) afforded 1.04 g (65%) of 4b in >99% purity. Tlc assay showed $R_f$=0.61 on $SiO_2$ using 25% ethyl acetate/hexane as the eluent. $^1H$ NMR (300 MHz, $CDCl_3$): δ 7.4-7.1 (m, 15H), 5.042 (s, 2H), 4.56 (br d, 1H, J=7.8 Hz), 4.28 (br d, 1H, J=9 Hz), 3.92-3.7 (br m, 2H), 2.8-2.6 (m, 4H), 1.6-1.4 (br s, 2H), 1.38 (s, 9H).

Example 6

Preparation of compound V' (1,6-diphenyl-5S-tert-butoxycarbonylamino-3S-hydroxy-2S-(5-thiazolemethoxy)carbonylaminohexane)

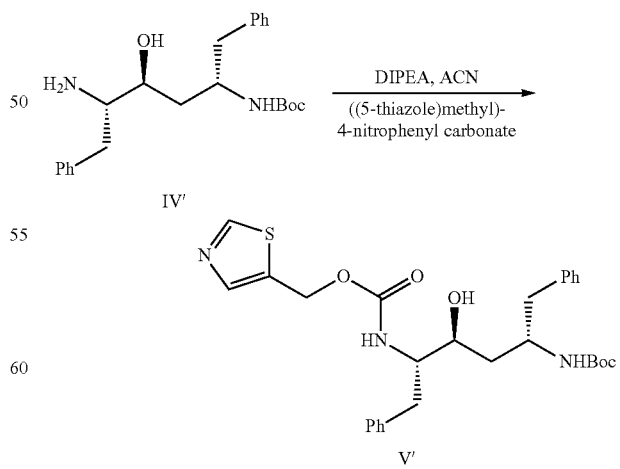

To a magnetically stirred mixture of amino alcohol IV' (3.84 g, 10 mmol) in acetonitrile (100 mL) at room temperature, was added ((5-thiazole)methyl)-4-nitrophenyl carbonate (3.08 g, 11 mmol). The reaction mixture was stirred for approximately 20 minutes and then was added diisopropylethylamine (2 mL, 11 mmol). The reaction was allowed to stir at room temperature for 48 hours. At this point, the reaction was analyzed by HPLC and judged to be complete. The reaction mixture was transferred to a round-bottom flask and the solvent was removed in vacuo. The residue was dissolved in ethyl acetate and transferred to a separatory funnel. The reaction mixture was washed twice with cold (0° C.) 5% sodium bisulfate solution (2×75 mL), twice with 1M sodium carbonate solution (2×100 mL), brine (100 mL) and dried over anhydrous sodium sulfate. The solvent was removed in vacuo to afford 6 g of crude material. The residue was chromatographed on silica gel (100 mL) using a 20% ethyl acetate/hexane to 60% ethyl acetate/hexane gradient to obtained 4.97 g (94%) of the desired carbamate V' as a white solid. Tlc assay showed $R_f$=0.32 on $SiO_2$ using 50% ethyl acetate/hexane as the eluent. $^1$H NMR (300 MHz, $CDCl_3$): δ 8.79 (s, 1H), 7.84 (s, 1H), 7.35-7.05 (m, 15H), 5.24 (s, 2H), 5.12 (d, 1H, J=9.3 Hz), 4.50 (br s, 1H), 3.9-3.7 (m, 2H), 3.64 (br s, 1H), 2.85 (d, 2H, J=7.5 Hz), 2.73 (d, 2H, J=6.6 Hz), 1.62 (br s, 2H), 1.39 (s, 9H).

Example 7

Preparation of compound 7b (3S-imidazolecarbothioic acid 1,6-diphenyl-5S-tert-butoxycarbonylamino-2S-(5-thiazolemethoxycarbonylaminohexane, ester)

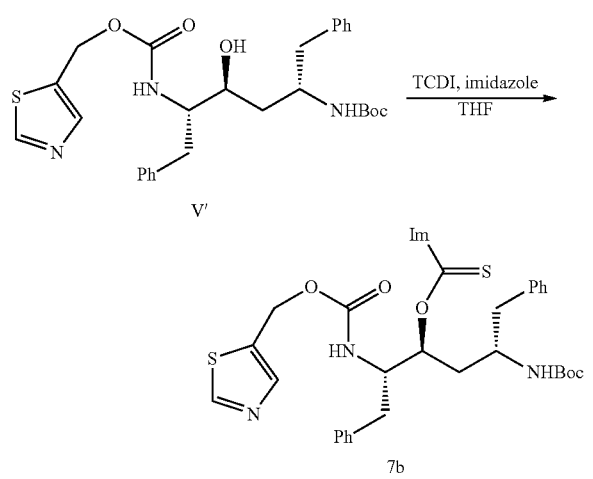

Thiocarbonyldiimidazole (TCDI) (1.07 g, 6 mmol) was added to a magnetically stirred solution of alcohol V' (1.58 g, 3 mmol) and imidazole (204 mg, 3 mmol) in THF (20 mL) at room temperature. The reaction mixture was stirred for 48 hours and then determined complete by HPLC. The reaction mixture was transferred to a round-bottom flask and the solvent was removed in vacuo. The residue was dissolved in ethyl acetate (200 mL) and transferred to a separatory funnel. The organic layer was washed twice with cold (0° C.) 5% sodium bisulfate solution (2×50 mL), saturated sodium bicarbonate solution (100 mL), brine (100 mL) and dried over anhydrous sodium sulfate. The solvent was removed in vacuo and the solids were filtered to afforded 2.2 g crude product. The crude solid was adsorbed onto 14 mL of flash silica gel and chromatographed on 40 mL of flash silica gel using a 20% ethyl acetate/hexane to 60% ethyl acetate/hexane gradient to afford 1.9 g (>99%) of imidazolide 7b (Im is imidazol-1-yl) as a white solid foam in 97 A % purity. Tlc assay showed $R_f$=0.32 on $SiO_2$ using 50% ethyl acetate/hexane as the eluent. $^1$H NMR (300 MHz, $CDCl_3$): δ 8.77 (s, 1H), 8.22 (s, 1H), 7.80 (s, 1H), 7.52 (s, 1H), 7.35-7.1 (m, 15H), 7.03 (s, 1H), 5.77 (m, 1H), 5.18 (q, 2H, J=9 Hz), 4.74 (m, 1H), 4.62 (br s, 1H), 4.45 (m, 1H), 4.2-4.1 (br s, 1H), 2.95-2.6 (m, 4H), 2.0-1.8 (br s, 2H), 1.38 (s, 9H).

Example 8

Preparation of compound 6 (1,6-diphenyl-5S-tert-butoxycarbonylamino-2S-(5-thiazolemethoxy)carbonylamino-hexane)

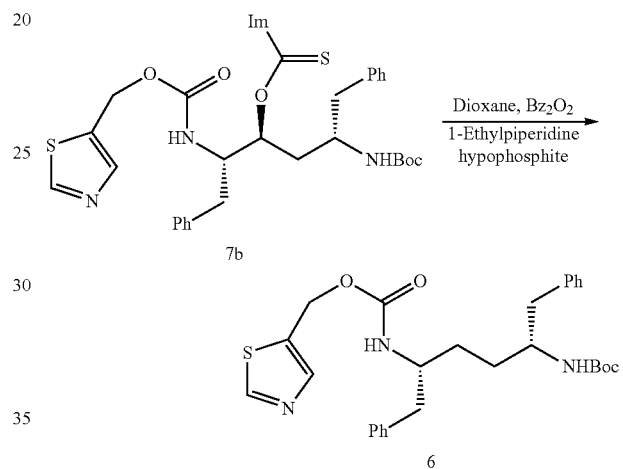

A solution of xanthate 7b (64 mg, 0.1 mmol) and benzoyl peroxide (18 mg, 0.075 mmol) in dioxane (1.5 mL) was added via a syringe pump to a magnetically stirred and deoxygenated mixture of dioxane (3 mL) and 1-ethylpiperidine hypophosphite (900 mg, 5 mmol) at 105° C. over two hours. After the addition was complete, the reaction mixture was heated at 105° C. for two additional hours. The reaction was cooled and judged complete by HPLC analysis. The isolated product mixture contained alcohol V' and compound 6 in a ratio 2:1.

Example 9

Preparation of compound 13 (2R-(2S-t-butoxycarbonylamino-3-phenylpropyl)-3S-benzylaziridine)

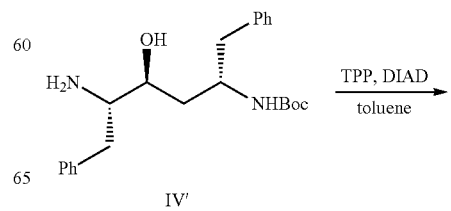

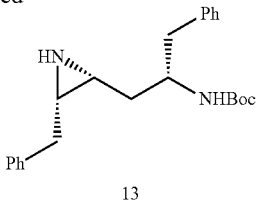

13

Diisopropyl diazodicarboxylate (17.3 mL, 88 mmol) was added to a mechanically stirred solution of triphenylphosphine (23.1 g, 88 mmol) in toluene (300 mL) at 5° C. The temperature was not allowed to rise above 10° C. during the addition. The solution was cooled back to 5° C. and then aminoalcohol IV' (30.76 g, 80 mmol) was added portionwise over approximately 10 minutes. The cooling bath was removed and the resulting suspension was allowed to stir for 48 hours. The reaction was filtered, washed with 150 mL of cold (0° C.) toluene, and dried afford 35 g of the white solid. The white solid was recrystallized from a mixture of 130 mL of methanol and 88 mL of water to afford 18.7 grams (63%) of 13. The recrystallization mother liquors and the filtrate were added together and concentrated in vacuo to afford 43 g of a yellow semi-solid. The residue was stirred with 400 mL of a 1:1 mixture of methanol and water overnight to form a white solid (37 g). This material was chromatographed on C-18 reverse-phase silica gel (1200 g) using a 50% methanol/water to 90% methanol/water gradient. The fractions containing the product were combined and the solvent was removed in vacuo to give 13 as a white solid (2.9 g, 10%). The combined total of the two crops of aziridine 13 was 21.6 g (73%). $^1$H NMR (300 MHz, CD$_3$OD): δ 7.35-7.15 (m, 10H), 4.0-3.85 (br s, 1H), 2.90-2.6 (m, 4H), 2.35-2.15 (m, 2H), 1.75-1.5 (m, 2H), 1.35 (s, 9H).

Example 10

Preparation of compound 9b (3S-toluene-4-sulfonic acid 1,6-Diphenyl-5S-tert-butoxycarbonylamino-2S-phenyl methoxycarbonylaminohexane, ester)

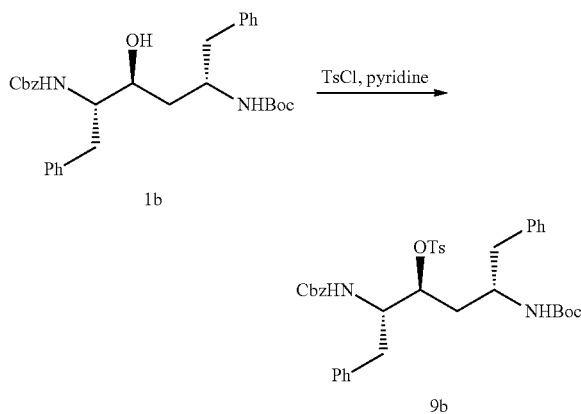

p-Toluenesulfonyl chloride (19.5 g, 102 mmol) was added in one portion to a solution of carbamate 1b (26.5 g, 51 mmol) dissolved in pyridine (80 mL) at room temperature. A slight exotherm (~5° C.) was noted. The reaction was stirred overnight at room temperature overnight. At the end of this period, the reaction was judged complete by tlc assay. The reaction mixture was poured into water (500 mL) and extracted with 20% ethyl acetate/hexane (1 L). The organic layer was washed with brine (50 mL), dried over anhydrous sodium sulfate, filtered and concentrated. The residue was azeotroped with toluene, but after the concentration was complete, the residue still contained some pyridine. The residue was adsorbed onto 200 mL of silica gel with ethyl acetate. After removal of the ethyl acetate, hexane was added to the silica gel. Removal of the hexane afforded free-flowing silica which was loaded on top of a silica gel pad (400 mL). The silica plug was rinsed with hexane (2 L), 10% ethyl acetate/hexane (4 L) and 20% ethyl acetate/hexane (4 L). The product eluted with 20% ethyl acetate/hexane. Combination of the product containing fractions and removal of the solvent in vacuo afforded 25.4 g (74% yield) of the desired tosylate 9b as a white solid. Tlc assay showed R$_f$=0.54 on SiO$_2$ using 25% ethyl acetate/hexane as the eluent. $^1$H NMR (300 MHz, CDCl$_3$): δ 7.77-7.74 (d, 2H), 7.4-7.0 (m, 19H), 5.0-4.8 (m, 2H), 4.74-4.66 (m, 1H), 4.63-4.60 (m, 1H), 4.42 (br s, 1H), 4.2-4.1 (m, 1H), 4.0 (br s, 1H), 2.65-2.35 (m, 4H), 2.42 (s, 3H), 1.66 (br s, 2H), 1.42 (s, 9H).

Example 11

Preparation of compound 10b (3S-toluene-4-sulfonic acid 1,6-Diphenyl-5S-amino-2S-phenylmethoxycarbonyl aminohexane, ester)

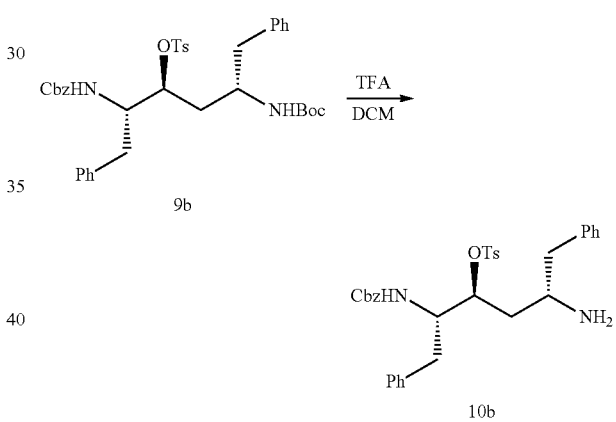

Dichloromethane (50 mL) was added to a 125 mL three-necked flask containing tosylate 9b (6.73 g, 10 mmol). The reaction mixture was cooled to –20° C. Trifluoroacetic acid (20 mL, 260 mmol) was added dropwise via addition funnel over 5 minutes and the resulting mixture was stirred at –20° C. for 10 minutes and then allowed to warm to room temperature and stir for 45 minutes. Analysis by HPLC at this point indicated that the reaction was complete.

A mixture of 1.2M (10%) solution of sodium bicarbonate (420 mL) and ice (100 g) was prepared. The reaction mixture was poured slowly (foaming) into the rapidly stirred mixture of ice and sodium bicarbonate solution. When all of the reaction mixture had been added, the pH of the mixture was approximately 8. The two-phase mixture was then poured into a separatory funnel. The layers were separated. The aqueous phase was washed twice with dichloromethane (2×100 mL). The combined organic phases were dried over anhydrous sodium sulfate. Removal of the solvent in vacuo afforded 5.8 g (100%) of tosylate 10b as a solid foam. Tlc assay showed R$_f$=0.32 on SiO$_2$ using 50% ethyl acetate/hexane as the eluent. $^1$H NMR (300 MHz, CDCl$_3$): δ 7.85-7.75 (m, 2H), 7.4-7.0 (m, 19H), 5.03-4.8 (m, 2H), 5.1-4.8 (br d, 1H), 3.2-2.8 (m, 2H), 2.8-2.5 (m, 2H), 2.42 (s, 3H).

Example 12

Preparation of compound 11b (2R-(2S-amino-3-phenylpropyl)-3S-benzylaziridine-1-carboxylic acid benzyl ester)

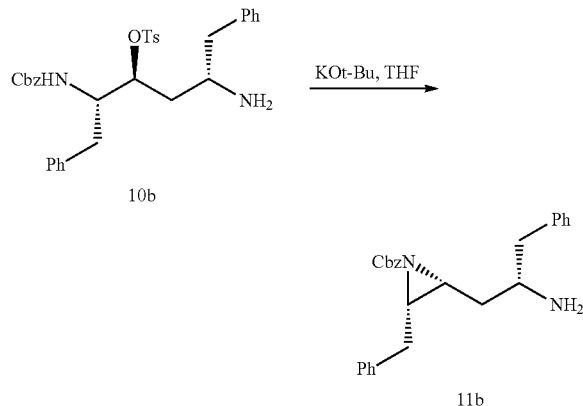

A 1M potassium t-butoxide solution in THF (7.4 mL, 7.4 mmol) was added to a solution of amino tosylate 10b (4.0 g, 7 mmol) in tetrahydrofuran (50 mL) at −20° C. During the addition, an exotherm of 2-3° C. was noted. After the addition was complete, the reaction mixture was allowed to warm to 0° C. TLC and HPLC indicated that the reaction was complete. The reaction mixture was poured into 200 mL of pH 6 phosphate buffer to quench the reaction. This mixture was then transferred to a separatory funnel and extracted with ethyl acetate (2×150 mL). The combined organic extracts were washed with brine (2×100 mL) and dried over anhydrous sodium sulfate. Filtration and removal of the solvent in vacuo afforded 2.91 g (>100%) of the desired material as a thick liquid. The crude material was chromatographed on silica gel using a 40% ethyl acetate/hexane to 100% ethyl acetate gradient. The aziridine 11b (2.58 g, 92% yield) was obtained as a sticky white solid. Tlc assay showed $R_f$=0.25 on $SiO_2$ using 50% ethyl acetate/hexane as the eluent. $^1$H NMR (300 MHz, $CDCl_3$): δ 7.4-7.1 (m, 15H), 5.15-5.0 (q, 2H, J=5.7 Hz), 3.4-3.25 (br s, 1H), 3.0-2.85 (m, 2H), 2.85-2.65 (m, 2H), 1.8-1.55 (m, 2H), 1.7-1.5 (br s, 2H).

Example 13

Preparation of compound 12 (1,6-diphenyl-2R-(t-butoxycarbonyl)amino-5R-carbamic acid, t-butyl ester) and compound 12a (1,6-diphenyl-2R-(t-butoxycarbonyl)amino-4S-carbamic acid, t-butyl ester)

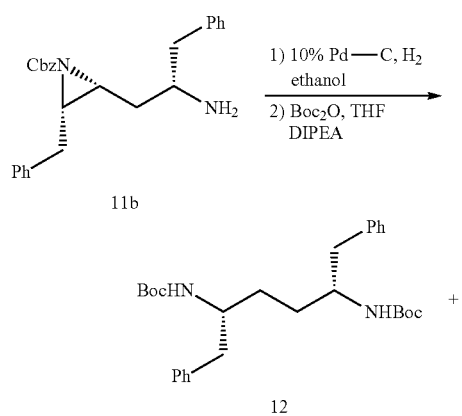

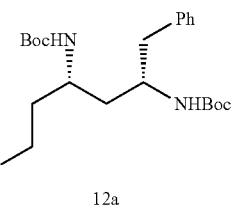

The aziridine 11b (400 mg, 1 mmol), 10% palladium on carbon (50% water wet) (200 mg) and absolute ethanol (20 mL) were added to a pressure vessel equipped with a stirring bar. The vessel was capped and three vacuum purges with nitrogen were performed. Then two vacuum purges with hydrogen were performed. The pressure of hydrogen was then regulated at 50 psi and the reaction was allowed to stir overnight. In the morning, the reaction was analyzed by HPLC. The starting material had been consumed and converted to two products. The reaction mixture was filtered through a pad of celite. The celite pad was washed thoroughly with ethanol. Removal of the solvent in vacuo afforded 268 mg (100%) of a clear oil.

The clear oil (268 mg, 1 mmol) was dissolved in THF (5 mL). Di-t-butyl dicarbonate (655 mg, 3 mmol) and diisopropylethylamine (523 μL, 3 mmol) were added to the reaction. The reaction was allowed to stir for 48 hours. HPLC of the reaction indicated that the reaction was complete. The solvent was removed and the residue was chromatographed on silica gel (40 mL) using a hexane to 30% ethyl acetate/hexane gradient. Two components were obtained. The first component was identified as 12a and weighed 99 mg (21% yield) (tlc assay showed $R_f$=0.30 on $SiO_2$, 10% ethyl acetate/hexane). $^1$H NMR (400 MHz, $CDCl_3$): δ 7.4-7.15 (m, 10H), 4.7-4.6 (br s, 1H), 4.6-4.5 (br s, 1H), 3.8-3.9 (br s, 1H), 3.6-3.75 (br s, 1H), 3.0-2.5 (m, 6H), 1.6-1.4 (br s, 2H), 1.42 (s, 9H), 1.37 (s, 9H). The second component was identified as 12 and weighed 255 mg (54% yield) (tlc assay showed $R_f$=0.24 on $SiO_2$, 10% ethyl acetate/hexane). $^1$H NMR (400 MHz, $CDCl_3$): δ 7.35-7.15 (m, 10H), 4.28 (d, 2H, J=8 Hz), 3.9-3.75 (br m, 2H), 2.8-2.6 (m, 4H), 1.6-1.4 (m, 2H), 1.41 (s, 18H).

Example 14

Preparation of compound IIa (1,6-diphenyl-2R,5R-diaminohexane dihydrochloride)

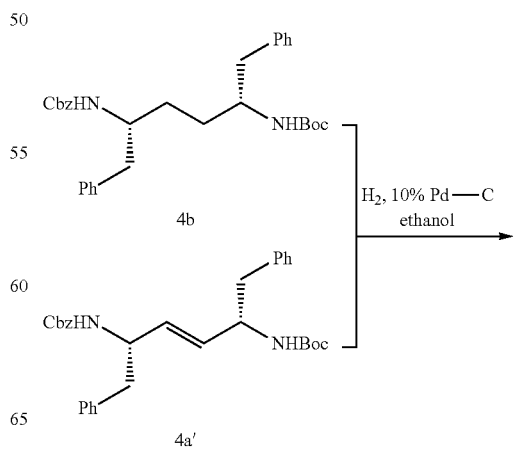

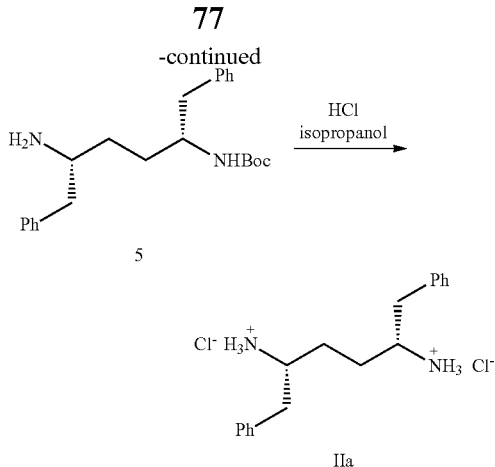

10% Palladium on carbon (50 mg) was added to a 40:60 mixture of 4a' and 4b (285 mg, 0.57 mmol) in ethanol (25 mL) in a thick-walled hydrogenation vessel equipped with a stirring bar. Three cycles of vacuum purges with nitrogen followed by three vacuum purges with hydrogen were performed. The internal hydrogen pressure was set at 50 psi and the reaction was allowed to stir at room temperature for 48 hours. At the end of this time, the reaction was analyzed by HPLC and found to be complete. The reaction was filtered through a pad of celite. The celite pad was thoroughly washed with ethanol (25 mL). The solvent was removed in vacuo to afford 223 mg (~100%) of a clear oil. The oil was chromatographed on silica gel to afford 150 mg (73% yield) of 5 as a thick oil which solidified on standing.

Compound 5 (100 mg, 0.27 mmol) was added to 5M HCl in isopropanol (3 mL). A solution formed after approximately 10 minutes and after 30 minutes, a fine, white precipitate started to come out of solution. The reaction was allowed to stir at room temperature overnight. At the end of this period, the reaction was judged complete by HPLC analysis. An aliquot (1 mL) was removed from the reaction and the solvent was removed with a nitrogen sparge. A white solid formed. Sodium hydroxide (3 mL of a 1N NaOH solution) was added to the solid. An organic liquid separated which was partitioned into MTBE. The MTBE solution was separated and blown down with a nitrogen sparge. Compound II (free base of IIa) (19 mg, 28% yield) was obtained as a clear thick oil after the solvent was removed.

The remainder of the isopropanol/HCl mixture was diluted with diethyl ether (10 mL). The resulting mixture was cooled to −78° C. in a dry-ice bath and filtered. The white solid was washed with diethyl ether (10 mL) and dried in a vacuum oven (no heat) at 25 mm Hg vacuum. Compound IIa (50 mg, 54% yield) was obtained as a white solid.

HPLC analysis of the 50 mg sample of IIa salt and 19 mg of II from the deprotection of 5 with HCl in isopropanol was performed. The diastereomeric excess of the IIa was >99%. The diastereomeric excess of II was 96.3%.

All publications, patents, and patent documents are incorporated by reference herein, as though individually incorporated by reference. Various embodiments and techniques have been described. However, it should be understood that many variations and modifications may be made while remaining within the spirit and scope of the disclosure.

What is claimed is:

1. A compound of structure:

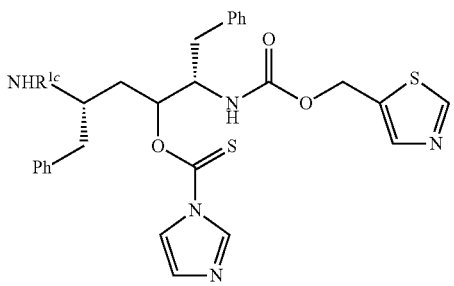

wherein:
$R^{1c}$ is —C(O)O($C_1$-$C_6$)alkyl wherein —C(O)O($C_1$-$C_6$)alkyl is optionally substituted with one or more halogen or ($C_1$-$C_6$)alkoxy;
or a salt thereof.

2. The compound of claim 1, which is:

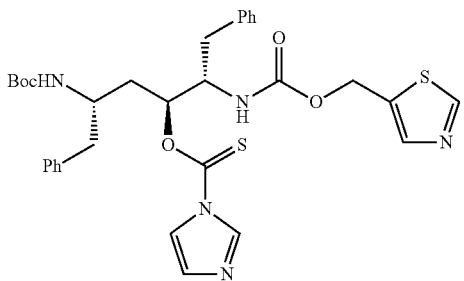 [SMILES: CC(C)(C)OC(=O)N[C@@H](Cc1ccccc1)C[C@H](OC(=S)n1ccnc1)[C@H](Cc1ccccc1)NC(=O)OCc1cncs1]

or a salt thereof.

* * * * *